United States Patent
Ferber

(10) Patent No.: US 10,179,151 B2
(45) Date of Patent: *Jan. 15, 2019

(54) METHODS OF TRANSDIFFERENTIATION AND METHODS OF USE THEREOF

(71) Applicants: ORGENESIS LTD., Tel Aviv (IL); TEL HASHOMER-MEDICAL RESEARCH, INFRASTRUCTURE AND SERVICES LTD., Ramat Gan (IL)

(72) Inventor: Sarah Ferber, Tel Aviv (IL)

(73) Assignees: ORGENESIS LTD., Tel Aviv (IL); TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,657

(22) Filed: Dec. 30, 2015

(65) Prior Publication Data

US 2016/0220616 A1 Aug. 4, 2016

Related U.S. Application Data

(60) Provisional application No. 62/098,050, filed on Dec. 30, 2014.

(51) Int. Cl.

| C12N 5/07 | (2010.01) |
|---|---|
| A61K 35/39 | (2015.01) |
| C12N 15/09 | (2006.01) |
| C12N 15/63 | (2006.01) |
| C07K 14/62 | (2006.01) |
| C12N 5/071 | (2010.01) |
| C12N 15/86 | (2006.01) |
| A61K 38/00 | (2006.01) |

(52) U.S. Cl.
CPC ............. *A61K 35/39* (2013.01); *C07K 14/62* (2013.01); *C12N 5/0676* (2013.01); *C12N 15/09* (2013.01); *C12N 15/63* (2013.01); *C12N 15/86* (2013.01); *A61K 38/00* (2013.01); *C12N 2501/60* (2013.01); *C12N 2506/14* (2013.01); *C12N 2510/00* (2013.01); *C12N 2710/10343* (2013.01)

(58) Field of Classification Search
None
See application file for complete search history.

(56) References Cited

U.S. PATENT DOCUMENTS

| 4,522,811 A | 6/1985 | Eppstein et al. |
|---|---|---|
| 4,737,323 A | 4/1988 | Martin et al. |
| 4,837,028 A | 6/1989 | Allen |
| 4,873,316 A | 10/1989 | Meade et al. |
| 4,980,286 A | 12/1990 | Morgan et al. |
| 4,992,417 A | 2/1991 | Katsoyannis et al. |
| 5,082,670 A | 1/1992 | Gage et al. |
| 5,328,470 A | 7/1994 | Nabel et al. |
| 5,424,286 A | 6/1995 | Eng |
| 5,427,940 A | 6/1995 | Newgard |
| 5,703,055 A | 12/1997 | Felgner et al. |
| 5,741,673 A | 4/1998 | Montminy |
| 5,849,989 A | 12/1998 | Edlund |
| 5,858,973 A | 1/1999 | Hebener et al. |
| 6,114,113 A | 9/2000 | McLaughlin-Taylor et al. |
| 6,242,666 B1 | 6/2001 | Sarvetnick et al. |
| 6,716,824 B1 | 4/2004 | Brunicardi |
| 6,774,120 B1 | 8/2004 | Ferber |
| 7,029,915 B2* | 4/2006 | Yang .................... C12N 5/0676 435/352 |
| 7,524,492 B2 | 4/2009 | Sharma |
| 8,119,405 B2* | 2/2012 | Ferber ................ A61K 38/1709 435/325 |
| 8,778,899 B2 | 7/2014 | Ferber |
| 2002/0081725 A1 | 6/2002 | Tsang et al. |
| 2003/0138948 A1 | 7/2003 | Fisk et al. |
| 2003/0219894 A1 | 11/2003 | Seino et al. |
| 2003/0223974 A1 | 12/2003 | Yang |
| 2004/0213769 A1 | 10/2004 | Ferber |
| 2005/0090465 A1 | 4/2005 | Ferber |
| 2006/0122104 A1 | 6/2006 | Presnell et al. |
| 2010/0226976 A1 | 9/2010 | Machluf et al. |
| 2011/0280842 A1 | 11/2011 | Melton et al. |
| 2015/0017727 A1 | 1/2015 | Ferber |
| 2015/0050247 A1 | 2/2015 | Machluf et al. |
| 2016/0130559 A1* | 5/2016 | Ferber ................ A61K 38/1709 424/93.7 |

FOREIGN PATENT DOCUMENTS

| EP | 0264166 A1 | 4/1988 |
|---|---|---|
| EP | 1354942 A1 | 10/2003 |
| JP | 2011-223993 A | 11/2011 |

(Continued)

OTHER PUBLICATIONS

Berneman et al. Hum Gene Ther 2010;21;640-1.*
Krause et al. Cell Transplant 2014;23:805-17.*
Gerbal-Chaloin et al. Mol Pharmacol 2014;86:624-34.*
Khaoustov et al. In Vitro Cell Dev Biol 1999;35:501-9.*
Muniappan et al. BMC Physiol 2007;7:11, pp. 1-9.*
Sakai et al. PlosOne 2013;8:e70970.*
Akbarpour et al. "Insulin B chain 9-23 gene transfer to hepatocytes protects from type 1 diabetes by inducing Ag-specific FoxP3+ Tregs", Sci Transl Med. May 27, 2015;7(289):289ra81.
Ambasudhan et al. "Direct reprogramming of adult human fibroblasts to functional neurons under defined conditions", Cell Stem Cell. Aug. 5, 2011;9(2):113-8.

(Continued)

*Primary Examiner* — Qian Janice Li
(74) *Attorney, Agent, or Firm* — Mark S. Cohen; Pearl Cohen Zedek Latzer Baratz LLP

(57) ABSTRACT

Disclosed herein is a method for manufacturing a population of human insulin producing cells from non-pancreatic β-cells, wherein the resulting insulin producing cells have increased insulin content, or increased glucose regulated secretion of insulin, or a combination of both.

26 Claims, 41 Drawing Sheets

Specification includes a Sequence Listing.

(56) References Cited

FOREIGN PATENT DOCUMENTS

| WO | WO 1994/008598 A1 | 4/1994 |
|---|---|---|
| WO | WO 1995/005463 | 2/1995 |
| WO | WO 1997/020075 A1 | 6/1997 |
| WO | WO 1997/049728 A1 | 12/1997 |
| WO | WO 2000/072885 A2 | 12/2000 |
| WO | WO 2003/033697 A1 | 4/2003 |
| WO | WO 2003/078636 A1 | 9/2003 |
| WO | WO 2004/098646 A1 | 11/2004 |
| WO | WO 2008/013737 A2 | 1/2008 |
| WO | WO 2009/126927 A2 | 10/2009 |
| WO | WO 2010/022395 A2 | 2/2010 |
| WO | WO 2011/159726 A2 | 12/2011 |
| WO | WO 2013/021389 A2 | 2/2013 |
| WO | WO/2014/207578 A2 | 12/2014 |

OTHER PUBLICATIONS

Aviv et al. "Exendin-4 promotes liver cell proliferation and enhances the PDX-1 induced liver to pancreas transdifferentiation process", J Biol Chem. Nov. 27, 2009;284(48):33509-20.
Banga et al. "In vivo reprogramming of Sox9+ cells in the liver to insulin-secreting ducts", PNAS Sep. 18, 2012, vol. 109, No. 38, pp. 15336-15341.
Ben Nasr et al. "Co-transplantation of autologous MSCs delays islet allograft rejection and generates a local immunoprivileged site", Acta Diabetol. Oct. 2015;52(5):917-27.
Ber et al. "Functional, persistent, and extended liver to pancreas transdifferentiation", J Biol Chem. Aug. 22, 2003;278(34):31950-7.
Bernardo et al. "Pancreatic transcription factors and their role in the birth, life and survival of the pancreatic beta cell", Mol Cell Endocrinol. Nov. 6, 2008;294(1-2):1-9.
Berneman-Zeitouni et al. "The Temporal and Hierarchical Control of Transcription Factors-Induced Liver to Pancreas Transdifferentiation", PLOS ONE Feb. 1, 2014, vol. 9| Issue 2, pp. 1-10.
Bonal et al. "Genes controlling pancreas ontogeny", Int J Dev Biol. 2008;52(7):823-35.
Borowiak "The new generation of beta-cells: replication, stem cell differentiation, and the role of small molecules", Rev Diabet Stud. 2010 Summer;7(2):93-104.
Brun et al. "A focus on the role of Pax4 in mature pancreatic islet beta-cell expansion and survival in health and disease", J Mol Endocrinol. Feb. 2008;40(2):37-45.
Chakrabarti et al. "Transcription factors direct the development and function of pancreatic beta cells", Trends Endocrinol Metab. Mar. 2003;14(2):78-84.
Collombat et al. "Specifying pancreatic endocrine cell fates", Mech Dev. Jul. 2006;123(7):501-12.
Collombat et al. "Opposing actions of Arx and Pax4 in endocrine pancreas development", Genes Dev. Oct. 15, 2003;17(20):2591-603.
Cozar-Castellano et al. "Molecular engineering human hepatocytes into pancreatic beta cells for diabetes therapy", Proc Natl Acad Sci U S A. May 31, 2005;102(22):7781-2.
D'Amour et al. "Efficient differentiation of human embryonic stem cells to definitive endoderm", Nat Biotechnol. Dec. 2005;23(12):1534-41.
Eberhard et al. "The pancreatic beta-cell in the islet and organ community", Curr Opin Genet Dev. Oct. 2009;19(5):469-75.
Ferber et al. "Pancreatic and duodenal homeobox gene 1 induces expression of insulin genes in liver and ameliorates streptozotocin-induced hyperglycemia", Nat Med. May 2000;6(5):568-72.
Figliuzzi et al. "Mesenchymal stem cells help pancreatic islet transplantation to control type 1 diabetes", World J Stem Cells. Apr. 26, 2014;6(2):163-72.
Gefen-Halevi et al. "NKX6.1 promotes PDX-1-induced liver to pancreatic β-cells reprogramming", Cell Reprogram. Dec. 2010;12(6):655-64.
Goodson, In: Medical Applications of Controlled Release 1984. (CRC Press, Boca Raton, Fla.).
Gradwohl et al. "neurogenin3 is required for the development of the four endocrine cell lineages of the pancreas", Proc Natl Acad Sci U S A. Feb. 15, 2000;97(4):1607-11.
Hamad et al. "Distinct requirements for Ras oncogenesis in human versus mouse cells", Genes & Development, 2002, 16:2045-2057.
Hanna et al. "Direct reprogramming of terminally differentiated mature B lymphocytes to pluripotency", Cell. Apr. 18, 2008;133(2):250-64.
He et al. "A simplified system for generating recombinant adenoviruses", Proc Natl Acad Sci U S A. Mar. 3, 1998;95(5):2509-14.
Ieda et al. "Direct reprogramming of fibroblasts into functional cardiomyocytes by defined factors", Cell. Aug. 6, 2010;142(3):375-86.
Ito et al. "Mesenchymal stem cell and islet co-transplantation promotes graft revascularization and function", Transplantation. Jun. 27, 2010;89(12):1438-45.
Iwasaki et al. "The order of expression of transcription factors directs hierarchical specification of hematopoietic lineages", Genes Dev. Nov. 1, 2006;20(21):3010-21.
Joliot et al. "Antennapedia homeobox peptide regulates neural morphogenesis", Proc Natl Acad Sci U S A. Mar. 1, 1991;88(5):1864-8.
Kaneto et al. "A crucial role of MafA as a novel therapeutic target for diabetes", J Biol Chem. Apr. 15, 2005;280(15):15047-52.
Kaneto et al. "PDX-1/VP16 fusion protein, together with NeuroD or Ngn3, markedly induces insulin gene transcription and ameliorates glucose tolerance", Diabetes. Apr. 2005;54(4):1009-22.
Kataoka et al. "MafA is a glucose-regulated and pancreatic beta-cell-specific transcriptional activator for the insulin gene", J Biol Chem. Dec. 20, 2002;277(51):49903-10.
Koizumi et al. "Hepatic regeneration and enforced PDX-1 expression accelerate transdifferentiation in liver", Surgery. Aug. 2004;136(2):449-57.
Kojima et al. "NeuroD-betacellulin gene therapy induces islet neogenesis in the liver and reverses diabetes in mice", Nat Med. May 2003;9(5):596-603.
Kroon et al. "Pancreatic endoderm derived from human embryonic stem cells generates glucose-responsive insulin-secreting cells in vivo", Nat Biotechnol. Apr. 2008;26(4):443-52. doi: 10.1038/nbt1393.
MaxCyte GT® Flow Transfection System at http://www.maxcyte.com/applications/mRNA-CAR.php, 2015.
Meivar-Levy et al. "New organs from our own tissues: liver-to-pancreas transdifferentiation", Trends Endocrinol Metab. Dec. 2003;14(10):460-6.
Meivar-Levy et al. "Regenerative medicine: using liver to generate pancreas for treating diabetes", Isr Med Assoc J. Jun. 2006;8(6):430-4.
Meivar-Levy et al. "Adult cell fate reprogramming: converting liver to pancreas", Methods Mol Biol. 2010;636:251-83.
Meivar-Levy et al. "Human liver cells expressing albumin and mesenchymal characteristics give rise to insulin-producing cells", J Transplant. 2011;2011:252387.
Meivar-Levy et al. "Pancreatic and duodenal homeobox gene 1 induces hepatic dedifferentiation by suppressing the expression of CCAAT/enhancer-binding protein beta", Hepatology. Sep. 2007;46(3):898-905.
Murtaugh et al. "Genes, signals, and lineages in pancreas development", Annu Rev Cell Dev Biol. 2003;19:71-89.
Nishimura et al. "Expression of MafA in pancreatic progenitors is detrimental for pancreatic development", Dev Biol. Sep. 1, 2009;333(1):108-20.
Offield et al. "PDX-1 is required for pancreatic outgrowth and differentiation of the rostral duodenum", Development. Mar. 1996;122(3):983-95.
Olbrot et al. "Identification of beta-cell-specific insulin gene transcription factor RIPE3b1 as mammalian M", Proc Natl Acad Sci U S A. May 14, 2002;99(10):6737-42.
Pang et al. "Induction of human neuronal cells by defined transcription factors", Nature. May 26, 2011;476(7359):220-3.
Reniers et al. "Industrialization of a Cell-based Autologous Therapy Targeting Diabetes: Industrialization of a Liver Cell Proliferation Process from Petri Dish to the Xpansion® Multiplate Bioreactor",

(56) References Cited

OTHER PUBLICATIONS

Pall.com. Xpansion Multiplate Bioreactor System. 2015: http://www.pall.com/main/biopharmaceuticals/product.page?lid=hw7uq21i. Accessed Aug. 13, 2015.
Sapir et al. "Cell-replacement therapy for diabetes: Generating functional insulin-producing tissue from adult human liver cells", Proc Natl Acad Sci U S A. May 31, 2005;102(22):7964-9.
Saudek et al. "A preliminary trial of the programmable implantable medication system for insulin delivery", N Engl J Med. Aug. 31, 1989;321(9):574-9.
Seijffers et al. "Increase in PDX-1 levels suppresses insulin gene expression in RIN 1046-38 cells", Endocrinology. Jul. 1999;140(7):3311-7.
Sheyn et al. "Genetically modified cells in regenerative medicine and tissue engineering", Adv Drug Deliv Rev. Jun. 15, 2010;62(7-8):683-98.
Shternhall et al. "Ectopic PDX-1 expression in liver ameliorates type 1 diabetes", J Autoimmun. Mar.-May 2007;28(2-3):134-42.
Slack et al. "Transdifferentiation and metaplasia—switching cell types", Curr Opin Genet Dev. Oct. 2001;11(5):581-6.
Song et al. "Islet cell differentiation in liver by combinatorial expression of transcription factors neurogenin-3, BETA2, and RIPE3b1", Biochem Biophys Res Commun. Mar. 9, 2007;354(2):334-9.
Stoffers et al. "Homeodomain protein IDX-1: a master regulator of pancreas development and insulin gene expression", Trends Endocrinol Metab. May-Jun. 1997;8(4):145-51.
Szabo et al. "Direct conversion of human fibroblasts to multilineage blood progenitors", Nature. Nov. 25, 2010;468(7323):521-6.
Takahashi et al. "Induction of Pluripotent Stem Cells from Mouse Embryonic and Adult Fibroblast Cultures by Defined Factors", Cell 126, 663-676, Aug. 25, 2006.
Tang et al. "Role of Pax4 in Pdx1-VP16-mediated liver-to-endocrine pancreas transdifferentiation", Lab Invest. Aug. 2006;86(8):829-41.
Treacy et al. "Adenoviral transduction of mesenchymal stem cells: in vitro responses and in vivo immune responses after cell transplantation", PLoS One. 2012;7(8):e42662.
Varda-Bloom et al. "Tissue-specific gene therapy directed to tumor angiogenesis", Gene Ther. Jun. 2001;8(11):819-27.
Vierbuchen et al. "Direct conversion of fibroblasts to functional neurons by defined factors", Nature. Feb. 25, 2010;463(7284):1035-41.
Wang et al. "Adenovirus transduction is required for the correction of diabetes using Pdx-1 or Neurogenin-3 in the liver", Mol Ther. Feb. 2007;15(2):255-63.
Watada et al. "Involvement of the Homeodomain-Containing Transcription Factor PDX-1 in Islet Amyloid Polypeptide Gene Transcription", Biochemical and Biophysical Research Communications 229, 746-751, 1996.
Wu et al. "Receptor-mediated in vitro gene transformation by a soluble DNA carrier system", J Biol Chem. Apr. 5, 1987;262(10):4429-32.
Xu et al "Mesenchymal stem cells differentially mediate regulatory T cells and conventional effector T cells to protect fully allogeneic islet grafts in mice", Diabetologia. Apr. 2012;55(4):1091-102.
Yamanaka et al. "Induction of pluripotent stem cells from mouse fibroblasts by four transcription factors", Cell Prolif. Feb. 2008;41 Suppl 1:51-6.
Yechoor et al. "Minireview: beta-cell replacement therapy for diabetes in the 21st century: manipulation of cell fate by directed differentiation", Mol Endocrinol. Aug. 2010;24(8):1501-11.
Yeung et al. "Human mesenchymal stem cells protect human islets from pro-inflammatory cytokines", PLoS One. 2012;7(5):e38189.
Zhou et al. "In vivo reprogramming of adult pancreatic exocrine cells to beta-cells", Nature. Oct. 2, 2008;455(7213):627-32.
Ahlgren et al. "The morphogenesis of the pancreatic mesenchyme is uncoupled from that of the pancreatic epithelium in IPF1/PDX1-deficient mice" Development. May 1, 1996;122(5)1409-16.

Amann et al. "Tightly regulated tac promoter vectors useful for the expression of unfused and fused proteins in *Escherichia coli*", Gene. Sep. 30, 1988;69(2):301-15.
Anderson WF, Colby M, McGaheuey M, Mehta S. "Human gene therapy" Nature Apr. 1998;392:25-30.
Baldari et al. "A novel leader peptide which allows efficient secretion of a fragment of human interleukin 1 beta in *Saccharomyces cerevisiae*" The EMBO journal. Jan. 1987;6(1):229.
Banerji et al. "A lymphocyte-specific cellular enhancer is located downstream of the joining region in immunoglobulin heavy chain genes" Cell. Jul. 1, 1983;33(3):729-40.
Bhandari et al. "Cloning, nucleotide sequence, and potential regulatory elements of the glutamine synthetase gene from murine 3T3-L1 adipocytes" Proceedings of the National Academy of Sciences. Aug. 1, 1988;85(16):5789-93.
Bonner-Weir et al. "New sources of pancreatic [beta]-cells" Nature biotechnology. Jul. 1, 2005:23(7):857.
Bretherton-Watt et al. "Insulin upstream factor 1 and a novel ubiquitous factor bind to the human islet amyloid polypeptide/amylin gene promoter" Biochemical Journal. Jan. 15, 1996;313(2):495-502.
Brevini et al. "No shortcuts to pig embryonic stem cells" Theriogenology. Sep. 1, 2010;74(4):544-50.
Burke et al. "Liver zonation occurs through a β-catenin-dependent, c-Myc-independent mechanism. Gastroenterology" Jun. 30, 2009;136(7):2316-24.
Byrne et al. "Multiplex gene regulation: a two-tiered approach to transgene regulation in transgenic mice" Proceedings of the National Academy of Sciences. Jul. 1, 1989;86(14):5473-7.
Calame et al. "Transcriptional controlling elements in the immunoglobulin and T cell receptor loci" Advances in immunology. Dec. 31, 1988;43:235-75.
Camper et al. "Postnatal repression of the alpha-fetoprotein gene is enhancer independent" Genes & development. Apr. 1, 1989;3(4):537-46.
Campos et al. "Divergent tissue-specific and developmental expression of receptors for glucagon and glucagon-like peptide-1 in the mouse" Endocrinology. May 1994;134(5):2156-64.
Cao et al. "High glucose is necessary for complete maturation of PDX1-VP16-expressing, hepatic cells into functional insulin-producing cells" Diabetes. Dec. 1, 2004;53(12):3168-78.
Caplan AI "Adult mesenchymal stem cells for tissue engineering versus regenerative medicine" Journal of cellular physiology. Nov. 1, 2007 1;213(2):341-7.
Chen et al. "Gene therapy for brain tumors: regression of experimental gliomas by adenovirus-mediated gene transfer in vivo" Proceedings of the National Academy of Sciences. Apr. 12, 1994;91(8):3054-7.
Chiang et al. "The role of the Wnt signaling pathway in incretin hormone production and function" Frontiers in physiology. Jul. 12, 2012;3:273.
Colnot et al. "Liver Zonation", Cagle PT, Molecular pathology of liver diseases. Monga SP, editor; Chapter 2. Springer Science & Business Media; Dec. 14, 2010; pp. 7-13.
Dunbar et al. "Identification of betacellulin as a major peptide growth factor in milk: purification, characterization and molecular cloning of bovine betacellulin" Biochemical Journal. Dec. 15, 1999;344(3):713-21.
Edlund et al. "Cell-specific expression of the rat insulin gene: evidence for role of two distinct 5'flanking elements" Science. Nov. 22, 1985;230(4728):912-6.
Ferber, S. "Transdifferentiation and its Implementation in Autologous Cell Replacement Therapy for Diabetes"; online presentation, pp. 1-35; upload date: May 29, 2014. Retrieved from the internet on; Apr. 11, 2016; Url: http://medical.wesrch.com/paper-details/pdf-ME1XXF8N4RZNR-transdifferentiation-and-its-implementation-in-autologous-cell-replacemnt-therapy-for-diabetes#page4.
Furukawa et al. "Possible involvement of atypical protein kinase C (PKC) in glucose-sensitive expression of the human insulin gene: DNA-binding activity and transcriptional activity of pancreatic and duodenal homeobox gene-1 (PDX-1) are enhanced via calphostin C-sensitive but phorbol 12-myristate 13-acetate (PMA) and Gö 6976-insensitive pathway" Endocrine journal. 1999;46(1):43-58.

(56) References Cited

OTHER PUBLICATIONS

GenBank Accession No. AAC41260.1, Mar. 6, 1998.
GenBank Accession No. AF036325.21, Mar. 6, 1998.
GenBank Accession No. AAA18355.1, May 5, 1994.
GenBank Accession No. AAA88820.1, Feb. 20, 1996.
GenBank Accession No. U35632.1, Feb. 21, 1996.
Göke et al. "Exendin-4 is a high potency agonist and truncated exendin-(9-39)-amide an antagonist at the glucagon-like peptide 1-(7-36)-amide receptor of insulin-secreting beta-cells" Journal of Biological Chemistry. Sep. 15, 1993;268(26):19650-5.
Goldspiel et al. "Human gene therapy" Clin Pharm 1993;12:488-505.
Gottesman S. "Minimizing proteolysis in *Escherichia coli*: genetic solutions" Methods in enzymology. Dec. 1989;185:119-29.
Gross et al. "Increased susceptibility of islets from diabetes-prone Psammomys obesus to the deleterious effects of chronic glucose exposure" Endocrinology. Dec. 1996;137(12):5610-5.
Ham et al. "Generation of insulin producing cells from the mouse primary hepatocytes" Tissue Eng Reg Med. Dec. 1, 2011;8:564-73.
Ham et al. "Generation of functional insulin-producing cells from neonatal porcine liver-derived cells by PDX1/VP16, BETA2/NeuroD and MafA. PloS one" Nov. 15, 2013;8(11):e79076.
Hamaguchi et al. "Comparison of Cytokine Effects on Mouse Pancreatic α-Cell and β-Cell Lines Viability, Secretory Function, and MHC Antigen Expression" Diabetes. Apr. 1, 1990;39(4):415-25.
Horb et al. "Experimental conversion of liver to pancreas" Current Biology, Jan. 21, 2003;13(2)105-15.
Howard et al. "Intracerebral drug delivery in rats with lesion-induced memory deficits", J Neurosurg. Jul. 1989;71(1):105-12.
Hsu et al. "Molecular cloning of a novel splice variant of the alpha subunit of the mammalian Go protein" Journal of Biological Chemistry. Jul. 5, 1990;265(19):11220-6.
International Search Report for PCT Application No. PCTIL2015051267 dated Apr. 16, 2016.
Iwasaki et al. "The order of expression of transcription factors directs hierarchical specification of hematopoietic lineages" Genes & development. Nov. 1, 2006;20(21):3010-21.
Jonsson et al. "Insulin-promoter-factor 1 is required for pancreas development in mice" Nature. Oct. 13, 1994;371(6498):606.
Kahn A. "Converting hepatocytes to [beta]-cells—a new approach for diabetes?" Nature medicine. May 1, 2000;6(5):505-7.
Kahn et al. "Islet amyloid: a long-recognized but underappreciated pathological feature of type 2 diabetes. Diabetes" Feb. 1, 1999;48(2):241-53.
Kajimoto et al. "Suppression of transcription factor PDX-1/IPF1/STF-1/IDX-1 causes no decrease in insulin mRNA in MIN6 cells" Journal of Clinical Investigation. Oct. 1, 1997;100(7):1840.
Kaufman et al. "Translational efficiency of polycistronic mRNAs and their utilization to express heterologous genes in mammalian cells" The EMBO journal. Jan. 1987;6(1):187.
Kessel et al. "Murine developmental control genes" Science. Jul. 27, 1990;249(4967):374-80.
Kojima et al. "Combined expression of pancreatic duodenal homeobox 1 and islet factor 1 induces immature enterocytes to produce insulin" Diabetes. May 1, 2002;51(5):1398-408.
Koller et al. "Inactivating the beta 2-microglobulin locus in mouse embryonic stem cells by homologous recombination" Proceedings of the National Academy of Sciences. Nov. 1, 1989;86(22):8932-5.
Koya et al. "Reversal of streptozotocin-induced diabetes in mice by cellular transduction with recombinant pancreatic transcription factor pancreatic duodenal homeobox-1" Diabetes. Mar. 1, 2008;57(3):757-69.
Kurjan et al. "Structure of a yeast pheromone gene (MFα): a putative α-factor precursor contains four tandem copies of mature α-factor" Cell. Oct. 1, 1982;30(3):933-43.
Li et al. "In vitro transdifferentiation of hepatoma cells into functional pancreatic cells" Mechanisms of development. Jun. 30, 2005;122(6):835-47.

Lin et al. "Expression of T cell antigen receptor heterodimers in a lipid-linked form" Science. Aug. 10, 1990;249(4969):677.
Loeffler et al. "Gene transfer into primary and established mammalian cell lines with lipopolyamine-coated DNA" Methods in enzymology. Dec. 31, 1993;217:599-618.
Lu "Hepatic progenitor cells of biliary origin with liver repopulation capacity" Nature cell biology. Aug. 1, 2015;17(8):971-83.
Luckow et al. "High level expression of nonfused foreign genes with Autographa californica nuclear polyhedrosis virus expression vectors" Virology. May 1, 1989;170(1):31-9.
Marshak et al. "Purification of the β-cell glucose-sensitive factor that transactivates the insulin gene differentially in normal and transformed islet cells" Proceedings of the National Academy of Sciences. Dec. 24, 1996;93(26):15057-62.
Milewski et al. "Conservation of PDX-1 Structure, Function, and Expression in Zebrafish 1" Endocrinology. Mar. 1, 1998;139(3):1440-9.
Miller et al. "IDX-1: a new homeodomain transcription factor expressed in rat pancreatic islets and duodenum that transactivates the somatostatin gene" The EMBO Journal. Mar. 1, 1994;13(5):1145.
Mitanchez et al. "Regulated expression of mature human insulin in the liver of transgenic mice" FEBS letters. Jan. 16, 1998;421(3):285-9.
Miyashita et al. "Sequential introduction and dosage balance of defined transcription factors affect reprogramming efficiency from pancreatic duct cells into insulin-producing cells" Biochemical and biophysical research communications. Feb. 21, 2014;444(4):514-9.
Munoz et al. "Conventional pluripotency markers are unspecific for bovine embryonic-derived cell-lines" Theriogenology. Jun. 30, 2008;69(9):1159-64.
Muzzin et al. "Hepatic insulin gene expression as treatment for type 1 diabetes mellitus in rats" Molecular Endocrinology. Jun. 1, 1997;11(6):833-7.
Nakajima-Nagata et al. "Pdx-1 enables insulin secretion by regulating synaptotagmin 1 gene expression" Biochemical and biophysical research communications. Jun. 4, 2004;318(3):631-5.
Nicolau et al. "In vivo expression of rat insulin after intravenous administration of the liposome-entrapped gene for rat insulin I" Proceedings of the National Academy of Sciences. Feb. 1, 1983;80(4):1068-72.
Nir et al. "How to make pancreatic βcells—prospects for cell therapy in diabetes" Current opinion in biotechnology. Oct. 31, 2005;16(5):524-9.
Noguchi et al. "Mechanism of PDX-1 protein transduction" Biochemical and biophysical research communications. Jun. 24, 2005;332(1):68-74.
Noguchi et al. "PDX-1 protein containing its own antennapedia-like protein transduction domain can transduce pancreatic duct and islet cells" Diabetes. Jul. 1, 2003:52(7):1732-7.
Novolin R [online], 2005-2010 [retrieved on Apr. 10, 2010]; Retrieved from the Internet:<URL: http://www.drugs.com/pro/novolin-r.html>, pp. 1-15.
Ohneda et al. "The homedomain of PDX-1 mediates multiple protein-protein interactions in the formation of a transcriptional activation complex on the insulin promoter" Molecular and Cellular Biology. Feb. 1, 2000;20(3):900-11.
Okitsu et al. "Transplantation of reversibly immortalized insulin-secreting human hepatocytes controls diabetes in pancreatectomized pigs" Diabetes. Jan. 1, 2004;53(1):105-12.
Otonkoski et al. "Stem cells in the treatment of diabetes" Annals of medicine. Jan. 1, 2005;37(7):513-20.
Ozcan et al. "Functional expression and analysis of the pancreatic transcription factor PDX-1 in yeast" Biochemical and biophysical research communications. Jul. 19, 2002;295(3):724-9.
Paris et al. "Equine embryos and embryonic stem cells: defining reliable markers of pluripotency" Theriogenology. Sep. 1, 2010;74(4):516-24.
Patel et al. "Therapeutic potential of mesenchymal stem cells in regenerative medicine" Stem cells international. Mar. 19, 2013;2013.
Peers B. Biosis Online. Accession No. PREV199598090886. 1994.

(56) References Cited

OTHER PUBLICATIONS

Peers et al. "Insulin expression in pancreatic islet cells relies on cooperative interactions between the helix loop helix factor E47 and the homeobox factor STF-1" Molecular Endocrinology. Dec. 1994;8(12):1798-806.
Pinkert et al. "An albumin enhancer located 10 kb upstream functions along with its promoter to direct efficient, liver-specific expression in transgenic mice" Genes & development. May 1, 1987;1(3):268-76.
Qing-Song et al. "Combined transfection of the three transcriptional factors, PDX-1, NeuroD1, and MafA, causes differentiation of bone marrow mesenchymal stem cells into insulin-producing cells" Experimental diabetes research. Jun. 19, 2012;2012.
Queen et al. "Immunoglobulin gene transcription is activated by downstream sequence elements". Cell. Jul. 1, 1983;33(3):741-8.
Rheinwald et al. "Epidermal growth factor and the multiplication of cultured human epidermal keratinocytes" Nature. Feb. 3, 1977;265(5593):421-4.
Rojas et al. "Islet cell development" InThe Islets of Langerhans 2010 (pp. 59-75). Springer Netherlands.
Ross, "Protein power: Researchers trigger insulin producton in diabetic mice", University of Florida News, Jan. 18, 2008 (http://news.efl.edu/2008/01/08/pdx1/).
Russ et al. "Development of human insulin-producing cells for cell therapy of diabetes", Pediatr Endocrinol Rev. Dec. 2011;9(2):590-7.
Sakurai et al. "Comparison of gene expression efficiency and innate immune response induced by Ad vector and lipoplex" Journal of controlled release. Feb. 26, 2007;117(3):430-7.
Salomaa et al. "Non-insulin-dependent diabetes mellitus and fasting glucose and insulin concentrations are associated with arterial stiffness indexes" Circulation. Mar. 1, 1995;91(5):1432-43.
Saudek et al. "A preliminary trial of the programmable implantable medication system for insulin delivery" New England Journal of Medicine. Aug. 31, 1989;321(9):574-9.
Schmidt et al. "The cytomegalovirus enhancer: a pan-active control element in transgenic mice" Molecular and Cellular Biology. Aug. 1, 1990;10(8):4406-11.
Schultz et al. "Expression and secretion in yeast of a 400-kDa envelope glycoprotein derived from Epstein-Barr virus" Gene. Dec. 31, 1987;54(1):113-23.
Seed, Brian. "An LFA-3 cDNA encodes a phospholipid-linked membrane protein homologous to its receptor CD2." 1987; 840-842.
Serup et al. "Induction of insulin and islet amyloid polypeptide production in pancreatic islet glucagonoma cells by insulin promoter factor 1" Proceedings of the National Academy of Sciences. Aug. 20, 1996;93(17):9015-20.
Shamblott et al. "Cell therapies for type 1 diabetes mellitus" Expert opinion on biological therapy. Mar. 1, 2004;4(3)269-77.
Smith et al. "Single-step purification of polypeptides expressed in *Escherichia coli* as fusions with glutathione S-transferase", Gene. Jul. 15, 1988;67(1):31-40.
Smith et al. "Production of human beta interferon in insect cells infected with a baculovirus expression vector" Molecular and cellular biology. Dec. 1, 1983;3(12):2156-65.
Stemple et al. "Isolation of a stem cell for neurons and glia from the mammalian neural crest" Cell. Dec. 11, 1992;71(6):973-85.
Studier et al. "Use of T7 RNA polymerase to direct expression of cloned genes" in Gene Expression Technology: Methods in Enzymology, vol. 185, 1990, pp. 60-89.
Takebe et al. "SR alpha promoter: an efficient and versatile mammalian cDNA expression system composed of the simian virus 40 early promoter and the R-U5 segment of human T-cell leukemia virus type 1 long terminal repeat" Molecular and Cellular Biology. Jan. 1, 1988;8(1):466-72.
Thowfeequ et al. "Transdifferentiation in developmental biology, disease, and in therapy" Developmental Dynamics. Dec. 1, 2007;236(12):3208-17.
Tréhin et al. "Chances and pitfalls of cell penetrating peptides for cellular drug delivery" European Journal of Pharmaceutics and Biopharmaceutics. Sep. 30, 2004;58(2):209-23.
Tur-Kaspa et al. "Use of electroporation to introduce biologically active foreign genes into primary rat hepatocytes" Molecular and cellular biology. Feb. 1, 1986;6(2):716-8.
Verma et al. "Gene therapy-promises, problems and prospects" Nature. Sep. 18, 1997;389(6648):239-42.
Vieau et al. "Mouse insulinoma beta TC3 cells express prodynorphin messenger ribonucleic acid and derived peptides: a unique cellular model for the study of prodynorphin biosynthesis and processing" Endocrinology. Mar. 1995 ;136(3):1187-96.
Wada et al. "Codon usage tabulated from the GenBank genetic sequence data" Nucleic acids research. 1992;20(Suppl):2011-2118.
Wang et al. "Stoichiometry of Gata4, Mef2c, and Tbx5 Influences the Efficiency and Quality of Induced Cardiac Myocyte ReprogrammingNovelty and Significance" Circulation research. Jan. 16, 2015;116(2):237-44.
Wang et al. "Self-renewing diploid Axin2+ cells fuel homeostatic renewal of the liver" Nature. Aug. 13, 2015;524(7564):180-5.
Wang et al. "Glucagon-like peptide-1 regulates the beta cell transcription factor, PDX 1, in insulinoma cells" Endocrinology. Oct. 1, 1999;140(10):4904-7.
Wang et al. "Pdx1 level defines pancreatic gene expression pattern and cell lineage differentiation" Journal of Biological Chemistry. Jul. 6, 2001;276(27):25279-86.
Weintraub et al. "Anti-sense RNA as a molecular tool for] genetic analysis" Trends in Genetics. Jan. 1, 1985 ;1:22-5.
Winoto et al. "A novel, inducible and T cell-specific enhancer located at the 3'end of the T cell receptor alpha locus" The EMBO journal. Mar. 1989;8(3):729.
Yamada et al. "In vitro transdifferentiation of mature hepatocytes into insulin-producing cells" Endocrine journal. 2006;53(6):789-95.
Yang et al. "In vitro trans-differentiation of adult hepatic stem cells into pancreatic endocrine hormone-producing cells" Proceedings of the National Academy of Sciences. Jun. 11, 2002;99(12):8078-83.
Zaret KS. "Regenerative biology: maintaining liver mass" Nature. Aug. 13, 2015;524(7564):165-6.
Hrvatin et al. "Differentiated human stem cells resemble fetal, not adult, β cells" Proceedings of the National Academy of Sciences. Feb. 25, 2014;111(8):3038-43.
Kirk et al. "Human embryonic stem cell derived islet progenitors mature inside an encapsulation device without evidence of increased biomass or cell escape" Stem cell research. May 31, 2014;12(3)807-14.
Pagliuca et al. "Generation of functional human pancreatic β cells in vitro" Cell. Oct. 9, 2014;159(2):428-39.
Rezania et al. "Reversal of diabetes with insulin-producing cells derived in vitro from human pluripotent stem cells" Nature biotechnology. Nov. 1, 2014;32(11):1121-33.
Shanmukhappa et al. "Hepatic to pancreatic switch defines a role for hemostatic factors in cellular plasticity in mice" Proceedings of the National Academy of Sciences of the United States of America. Jul. 19, 2005;102(29):10182-7.
Thowfeeou et al. "Reprogramming of liver to pancreas" Stem Cells in Regenerative Medicine. 2009:407-18.
Zalzman et al. "Differentiation of human liver-derived, insulin-producing cells toward the β-cell phenotype" Diabetes. Sep. 1, 2005;54(9):2568-75.
Graf T. "Historical origins of transdifferentiation and reprogramming" Cell stem cell. Dec. 2, 2011;9(6):504-16.
Torre et al. "Transcription dynamics in a physiological process: β-catenin signaling directs liver metabolic zonation" The international journal of biochemistry & cell biology. Feb. 28, 2011;43(2):271-8.
Supplementary European Search Report for European Application No. 15875374.9 dated May 18, 2018.

* cited by examiner

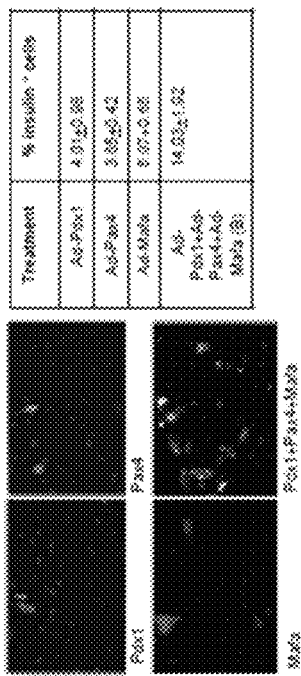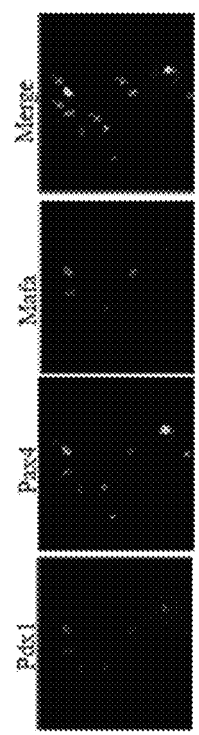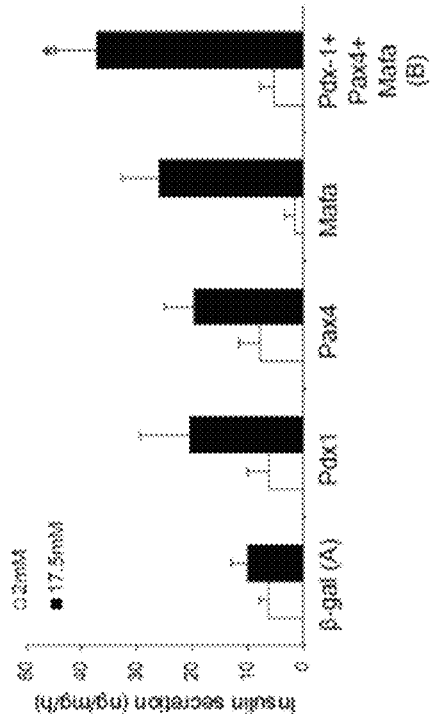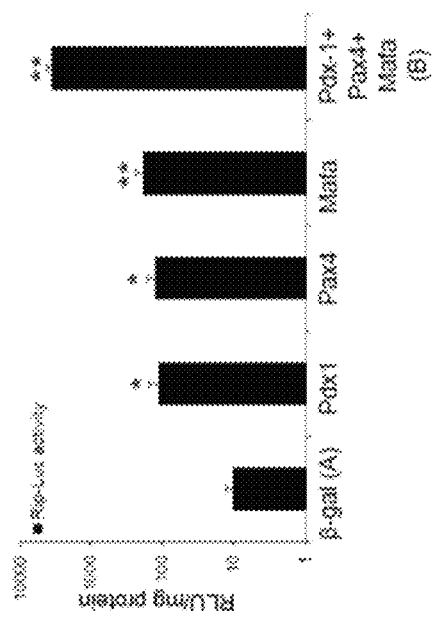
Figure 2A
Figure 2B
Figure 2C
Figure 2D

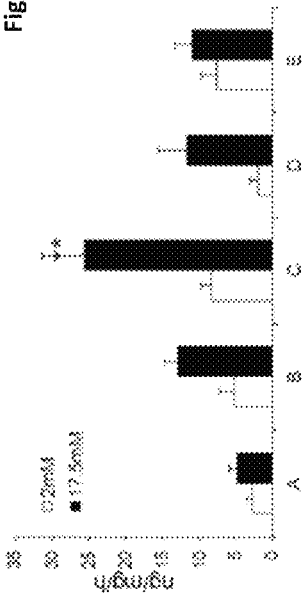
Figure 3A
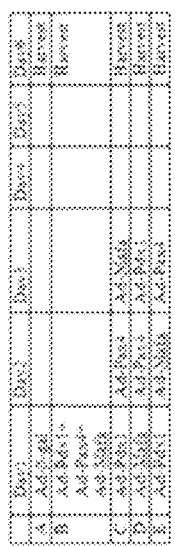
Figure 3B
Figure 3C
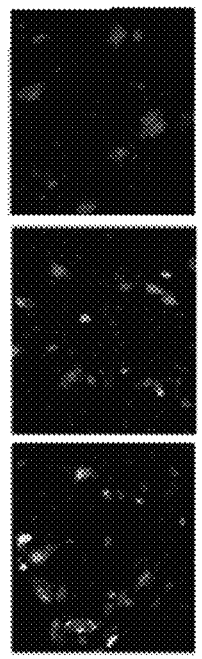
Figure 3D
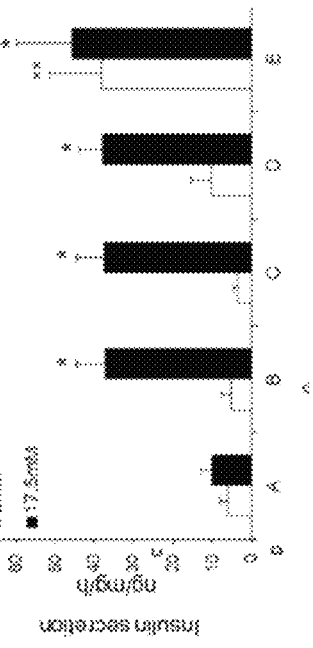
Figure 3E

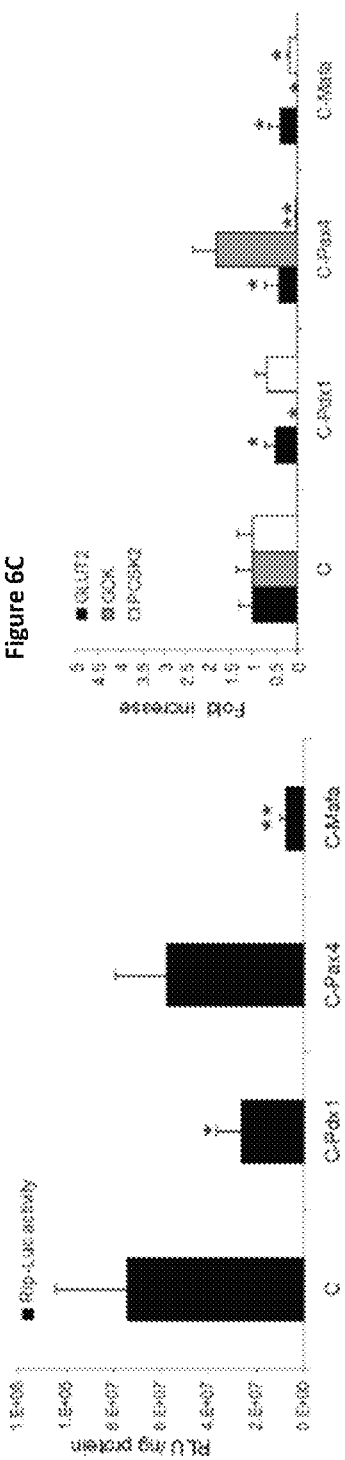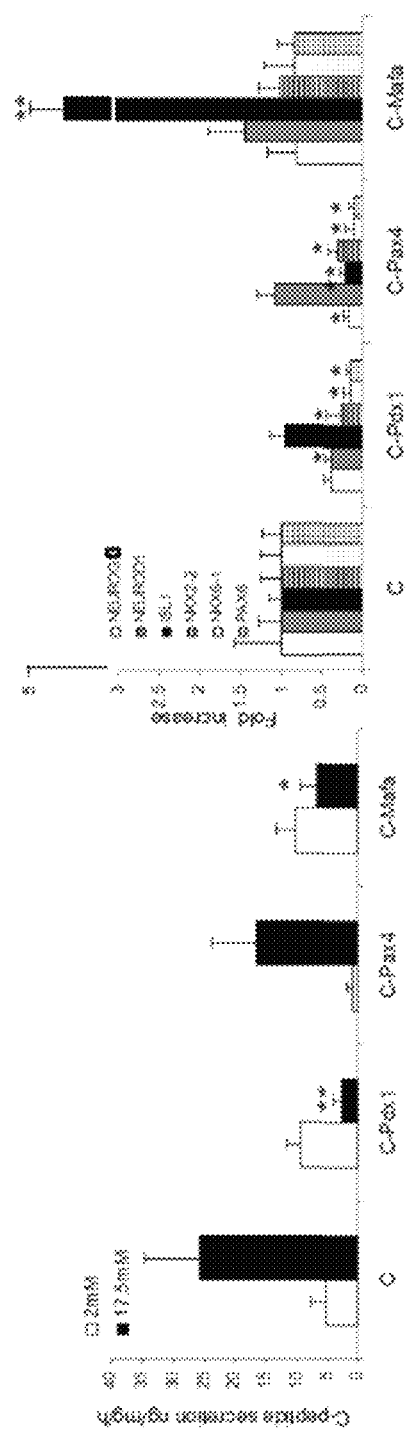
Figure 6A
Figure 6B
Figure 6C
Figure 6D

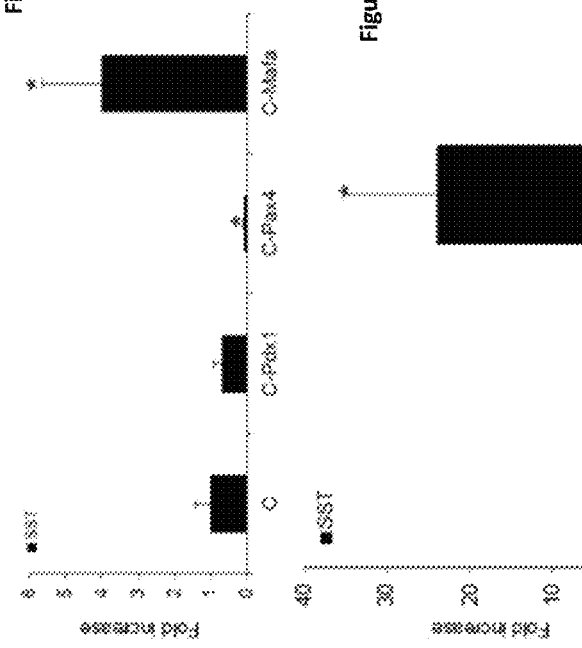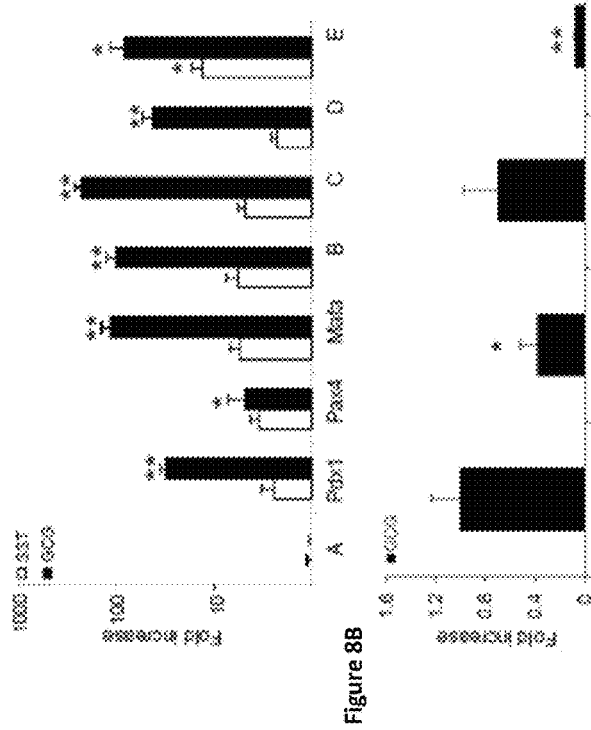
Figure 8A, Figure 8B, Figure 8C, Figure 8D, Figure 8E, Figure 8F Figure 12A
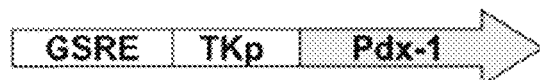
Figure 12B 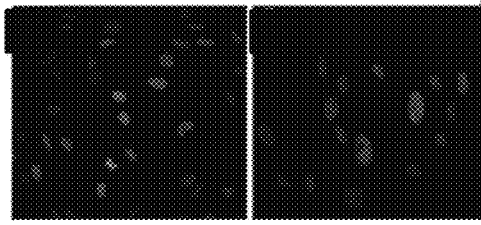 Figure 12C
Figure 12D
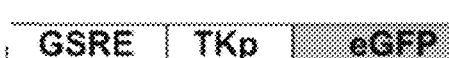
Figure 12E 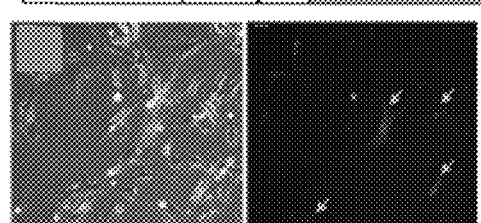 Figure 12F
Figure 13A 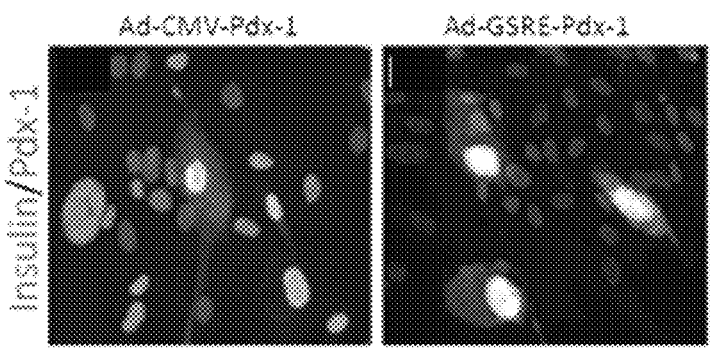 Figure 13B
Figure 13C
| | INS+ | Pdx-1+ | INS+/Pdx-1+ |
|---|---|---|---|
| Ad-CMV-Pdx-1 | 0.0% | 60% | 1% |
| Ad-GSRE-Pdx-1 | 4% | 16% | 2.5% |

Figure 14A
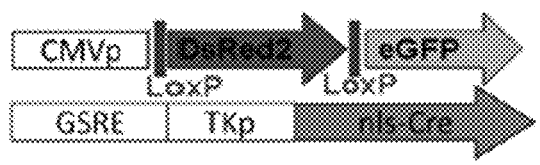
Figure 14B
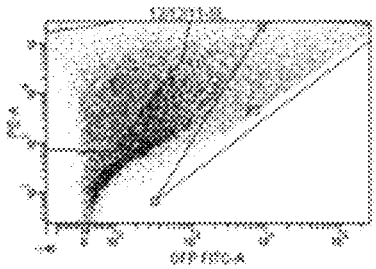
Figure 14C
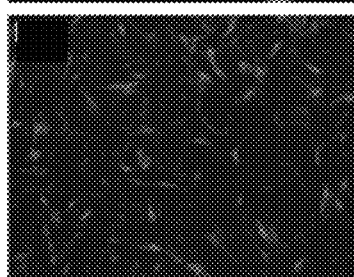
Figure 14D
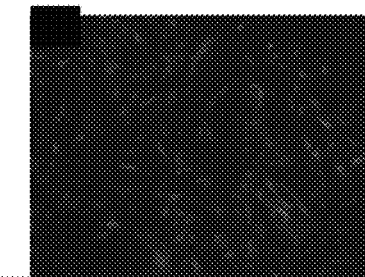
Figure 14E
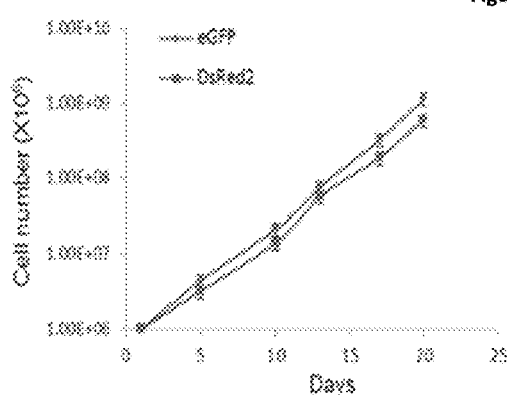
Figure 15A
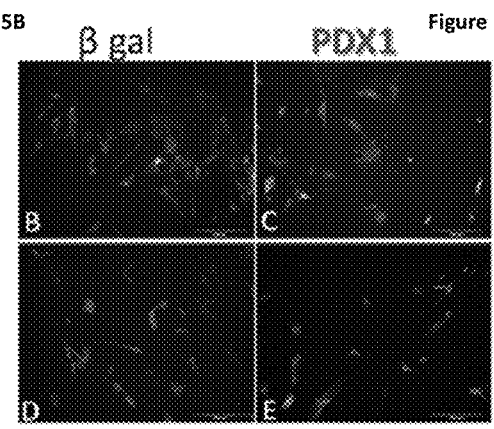
Figure 15B  Figure 15C
Figure 15D  Figure 15E

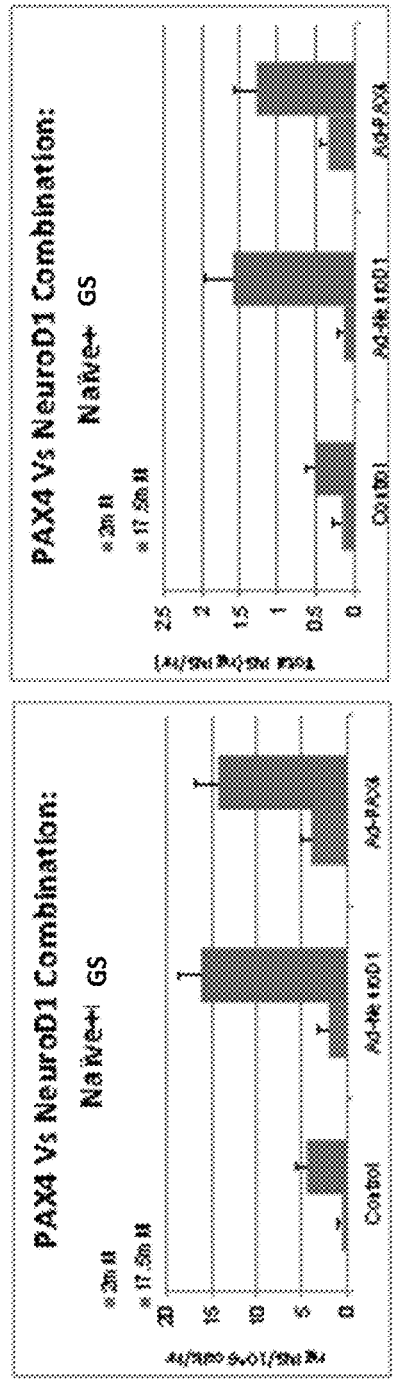
Figure 24A
Figure 24B
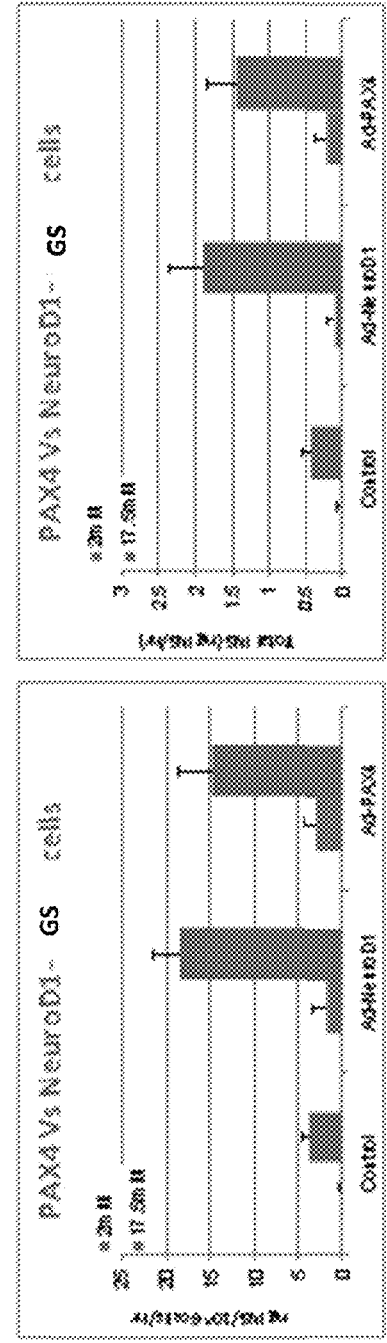
Figure 25A
Figure 25B

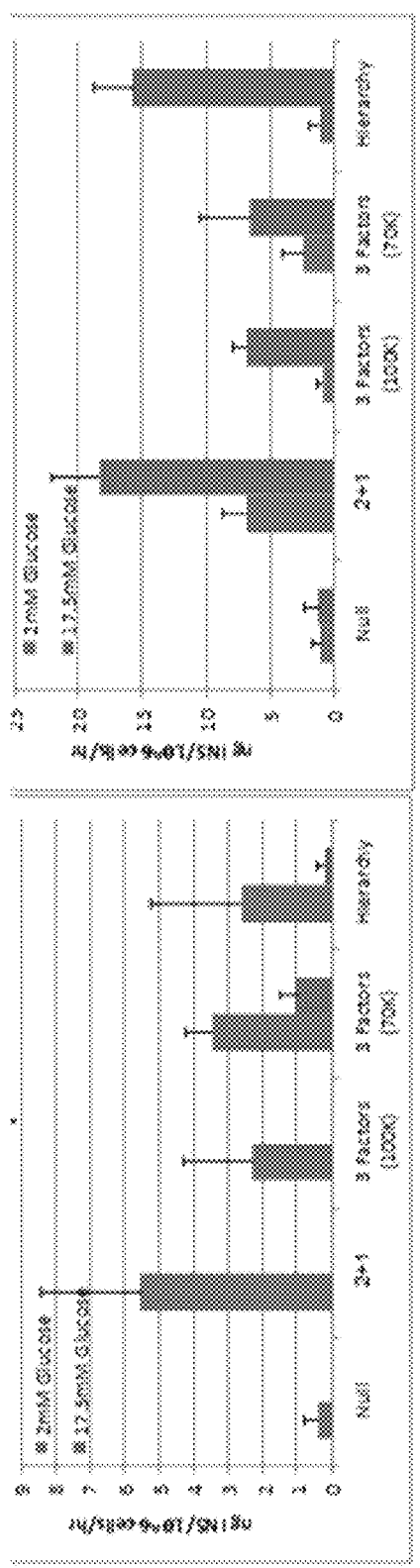
Figure 26A
Figure 26B
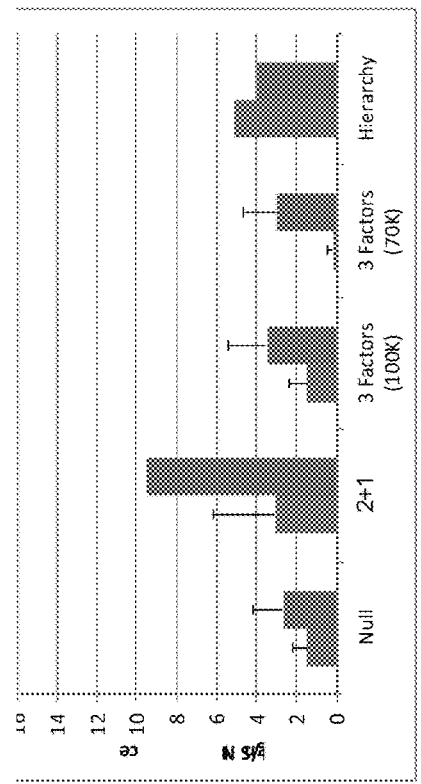
Figure 26C

| Run | Seeding density (cell/cm$^2$) | Harvest density (cell/cm$^2$) | Culture duration (days) |
|---|---|---|---|
| ORG-009 | 4,000 | 17,500 | 8 |
| ORG-014 | 4,000 | 22,780 | 7 |
| ORG-017 | 3,972 | 19,412 | 9 |

Figure 35

Figure 41A — Process CTL — Untreated Control
Figure 41B — Xpansion CTL
Figure 41C — Treated Cells
Figure 41D
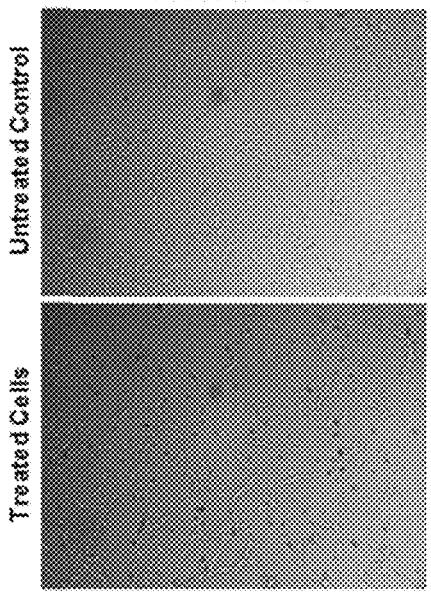
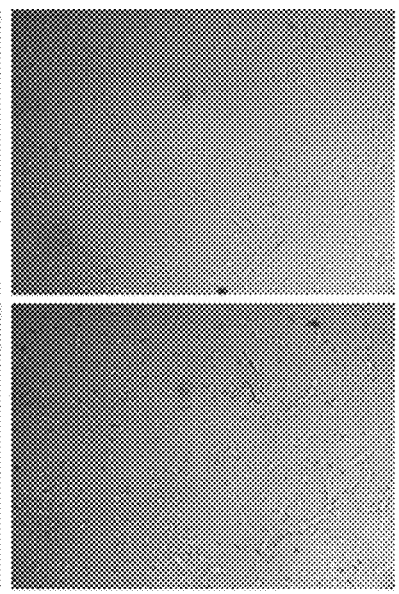
Xpansion 10
Plate 3
Plate 5
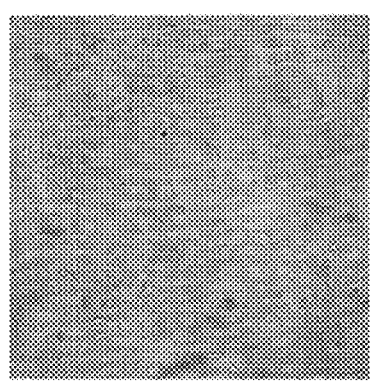
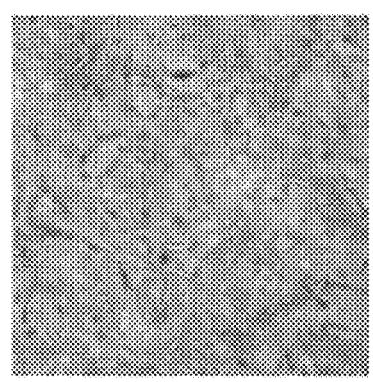
Figure 42A
Figure 42B

| ORG OIL | % CD105 | % CD73 | % CD90 | % CD44 | % Negative markers |
|---|---|---|---|---|---|
| P12 | 99.32 | 99.85 | 99.55 | 99.77 | 0.93 |
| P13 | 98.75 | 99.71 | 99.67 | 99.70 | 0.73 |
| P14 | 96.77 | 98.60 | 99.50 | 99.64 | 0.58 |
| P16_AdV infection | 89.77 | 99.41 | 99.22 | 99.91 | 0.44 |

SEQUENCE LISTING

```
<160> NUMBER OF SEQ ID NOS: 9

<210> SEQ ID NO 1
<211> LENGTH: 51
<212> TYPE: DNA
<213> ORGANISM: Rattus rattus

<400> SEQUENCE: 1
tcacatggaa ggatcaaagc aagcctgctt ctattcttgg aaacagagca a           51

<210> SEQ ID NO 2
<211> LENGTH: 51
<212> TYPE: DNA
<213> ORGANISM: Mus musculus

<400> SEQUENCE: 2
tcacatgaaa ggatcaaagc aaatccgctt ctattcttgg aaacagagca a           51

<210> SEQ ID NO 3
<211> LENGTH: 51
<212> TYPE: DNA
<213> ORGANISM: Homo sapiens

<400> SEQUENCE: 3
tcacatgaat ggatcaaagc aaatccattt ccattcttgg aaaagcagct c           51

<210> SEQ ID NO 4
<211> LENGTH: 283
<212> TYPE: PRT
<213> ORGANISM: Homo sapiens
```

<400> SEQUENCE: 4

```
Met Asn Gly Glu Glu Gln Tyr Tyr Ala Ala Thr Gln Leu Tyr Lys Asp
1               5                   10                  15
Pro Cys Ala Phe Gln Arg Gly Pro Ala Pro Glu Phe Ser Ala Ser Pro
            20                  25                  30
Pro Ala Cys Leu Tyr Met Gly Arg Gln Pro Pro Pro Pro Pro His
        35                  40                  45
Pro Phe Pro Gly Ala Leu Gly Ala Leu Glu Gly Ser Pro Pro Asp
    50                  55                  60
Ile Ser Pro Tyr Glu Val Pro Pro Leu Ala Asp Asp Pro Ala Val Ala
65                  70                  75                  80
His Leu His His His Leu Pro Ala Gln Leu Ala Leu Pro His Pro Pro
                85                  90                  95
Ala Gly Pro Phe Pro Glu Gly Ala Glu Pro Gly Val Leu Glu Glu Pro
            100                 105                 110
Asn Arg Val Gln Leu Pro Phe Pro Trp Met Lys Ser Thr Lys Ala His
            115                 120                 125
Ala Trp Lys Gly Gln Trp Ala Gly Gly Ala Tyr Ala Ala Glu Pro Glu
        130                 135                 140
Glu Asn Lys Arg Thr Arg Thr Ala Tyr Thr Arg Ala Gln Leu Leu Glu
145                 150                 155                 160
Leu Glu Lys Glu Phe Leu Phe Asn Lys Tyr Ile Ser Arg Pro Arg Arg
                165                 170                 175
Val Glu Leu Ala Val Met Leu Asn Leu Thr Glu Arg His Ile Lys Ile
            180                 185                 190
Trp Phe Gln Asn Arg Arg Met Lys Trp Lys Glu Glu Asp Lys Lys
        195                 200                 205
Arg Gly Gly Gly Thr Ala Val Gly Gly Gly Val Ala Glu Pro Glu
    210                 215                 220
Gln Asp Cys Ala Val Thr Ser Gly Glu Glu Leu Leu Ala Leu Pro Pro
225                 230                 235                 240
Pro Pro Pro Pro Gly Gly Ala Val Pro Pro Ala Ala Pro Val Ala Ala
                245                 250                 255
Arg Glu Gly Arg Leu Pro Pro Gly Leu Ser Ala Ser Pro Gln Pro Ser
            260                 265                 270
Ser Val Ala Pro Arg Arg Pro Gln Glu Pro Arg
        275                 280
```

<210> SEQ ID NO 5
<211> LENGTH: 852
<212> TYPE: DNA
<213> ORGANISM: Homo sapiens

<400> SEQUENCE: 5

```
atgaacggcg aggagcagta ctacgcggcc acgcagcttt acaaggaccc atgcgcgttc    60
cagcgaggcc cggcgccgga gttcagcgcc agccccctg cgtgcctgta catgggccgc   120
cagccccgc cgccgccgcc gcacccgttc cctggcgccc tgggcgcgct ggagcagggc   180
agccccccgg acatctcccc gtacgaggtg cccccctcg ccgacgaccc cgcggtggcg   240
caccttcacc accacctccc ggctcagctc gcgctccccc acccgccgc cgggcccttc   300
ccggagggag ccgagccggg cgtcctggag agcccaacc gcgtccagct gccttttccca  360
tgatgaagt ctaccaaagc tcacgcgtgg aaaggccagt gggcaggcgg cgcctacgct   420
gcggagccgg aggagaacaa gcggacgcgc acggcctaca cgcgcgcaca gctgctagag   480
```

```
ctggagaagg agttcctatt caacaagtac atctcacggc cgcgccgggt ggagctggct      540
gtcatgttga acttgaccga gagacacatc aagatctggt tccaaaaccg ccgcatgaag      600
tggaaaaagg aggaggacaa gaagcgcggc ggcgggacag ctgtcggggg tggcggggtc      660
gcggagcctg agcaggactg cgccgtgacc tccggcgagg agcttctggc gctgccgccg      720
ccgccgcccc ccggaggtgc tgtgccgccc gctgccccg ttgccgcccg agagggccgc      780
ctgccgcctg gccttagcgc gtcgccacag ccctccagcg tcgcgcctcg gcggccgcag      840
gaaccacgat ga                                                          852
```

<210> SEQ ID NO 6
<211> LENGTH: 356
<212> TYPE: PRT
<213> ORGANISM: Homo sapiens

<400> SEQUENCE: 6

```
Met Thr Lys Ser Tyr Ser Glu Ser Gly Leu Met Gly Glu Pro Gln Pro
  1               5                  10                  15

Gln Gly Pro Pro Ser Trp Thr Asp Glu Cys Leu Ser Ser Gln Asp Glu
                 20                  25                  30

Glu His Glu Ala Asp Lys Lys Glu Asp Asp Leu Glu Thr Met Asn Ala
             35                  40                  45

Glu Glu Asp Ser Leu Arg Asn Gly Gly Glu Glu Glu Asp Glu Asp Glu
         50                  55                  60

Asp Leu Glu Glu Glu Glu Glu Glu Glu Glu Asp Asp Asp Gln Lys
 65                  70                  75                  80

Pro Lys Arg Arg Gly Pro Lys Lys Lys Met Thr Lys Ala Arg Leu
                 85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
            115                 120                 125

Pro Cys Tyr Ser Lys Thr Gln Lys Leu Ser Lys Ile Glu Thr Leu Arg
130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300
```

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
            325                 330                 335

Asp Ser His Ser His His Glu Arg Val Met Ser Ala Gln Leu Asn Ala
        340                 345                 350

Ile Phe His Asp
        355

<210> SEQ ID NO 7
<211> LENGTH: 1071
<212> TYPE: DNA
<213> ORGANISM: Homo sapiens

<400> SEQUENCE: 7
atgaccaaat cgtacagcga gagtgggctg atgggcgagc ctcagcccca aggtcctcca        60
agctggacag acgagtgtct cagttctcag gacgaggagc acgaggcaga caagaaggag       120
gacgacctcg aagccatgaa cgcagaggag gactcactga ggaacggggg agaggaggag       180
gacgaagatg aggacctgga agaggaggaa gaagaggaag aggaggatga cgatcaaaag       240
cccaagagac gcggccccaa aaagaagaag atgactaagg ctcgcctgga gcgttttaaa       300
ttgagacgca tgaaggctaa cgcccgggag cggaaccgca tgcacggact gaacgcggcg       360
ctagacaacc tgcgcaaggt ggtgccttgc tattctaaga cgcagaagct gtccaaaatc       420
gagactctgc gcttggccaa gaactacatc tgggctctgt cggagatctc cgcgctcaggc      480 aaaagcccag acctggtctc cttcgttcag acgctttgca agggcttatc ccaacccacc       540
accaacctgg ttgcgggctg cctgcaactc aatcctcgga cttttctgcc tgagcagaac       600
caggacatgc ccccgcacct gccgacggcc agcgcttcct tccctgtaca ccctactcc        660 taccagtcgc ctgggctgcc cagtccgcct tacggtacca tggacagctc ccatgtcttc       720
cacgttaagc ctccgccgca cgcctacagc gcagcgctgg agcccttctt tgaaagccct       780
ctgactgatt gcaccagccc ttcctttgat ggacccctca gccgccgct cagcatcaat        840 ggcaacttct ctttcaaaca cgaaccgtcc gccgagtttg agaaaaatta tgcctttacc       900
atgcactatc ctgcagcgac actggcaggg gcccaaagcc acggatcaat cttctcaggc       960
accgctgccc ctcgctgcga gatccccata gacaatatta tgtccttcga tagccattca      1020
catcatgagc gagtcatgag tgcccagctc aatgccatat ttcatgatta g              1071

<210> SEQ ID NO 8
<211> LENGTH: 353
<212> TYPE: PRT
<213> ORGANISM: Homo sapiens

<400> SEQUENCE: 8

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly Gly
65                  70                  75                  80

```
Ala Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Ala Gly His His Val Arg Leu Glu
    210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
    290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
            340                 345                 350

Leu

<210> SEQ ID NO 9
<211> LENGTH: 1059
<212> TYPE: DNA
<213> ORGANISM: Homo sapiens

<400> SEQUENCE: 9
atggccgcgg agctggcgat gggcgccgag ctgcccagca gcccgctggc catcgagtac      60
gtcaacgact cgacctgat gaagttcgag gtgaagaagg agcctcccga ggccgagcgc     120
ttctgccacc gcctgccgcc aggctcgctg tcctcgacgc cgtcagcac gccctgctcc     180 tccgtgccct cctcgcccag cttctgcgcg cccagcccgg gcaccggcgg cggcggcggc     240 gcgggggcg gcgcggctc gtctcaggcc ggggcgccc ccgggccgcc gagcgggggc     300
cccggcgccg tcggggcac ctcggggaag ccggcgctgg aggatctgta ctggatgagc     360
ggctaccagc atcacctcaa ccccgaggcg ctcaacctga cgcccgagga cgcggtggag     420
gcgctcatcg gcagcggcca ccacggcgcg caccacggcg cgcaccaccc ggcggccgcc     480
gcagcctacg aggctttccg cggcccgggc ttcgcgggcg gcggcggagc ggacgacatg     540
```

```
ggcgccggcc accaccacgg cgcgcaccac gccgcccacc accaccacgc cgcccaccac     600
caccaccacc accaccacca tggcggcgcg ggacacggcg gtggcgcggg ccaccacgtg     660
cgcctggagg agcgcttctc cgacgaccag ctggtgtcca tgtcggtgcg cgagctgaac     720
cggcagctcc gcggcttcag caaggaggag gtcatccggc tcaagcagaa gcggcgcacg     780
ctcaagaacc gcggctacgc gcagtcctgc cgcttcaagc gggtgcagca gcggcacatt     840
ctggagagcg agaagtgcca actccagagc caggtggagc agctgaagct ggaggtgggg     900
cgcctggcca aagagcggga cctgtacaag gagaaatacg agaagctggc gggccggggc     960
ggccccggga gcgcgggcgg ggccggtttc ccgcgggagc cttcgccgcc gcaggccggt    1020
cccggcgggg ccaagggcac ggccgacttc ttcctgtag                           1059
```

METHODS OF TRANSDIFFERENTIATION AND METHODS OF USE THEREOF

CROSS REFERENCE TO RELATED APPLICATIONS

This application claims the benefit of U.S. Provisional Application Ser. No. 62/098,050, filed on Dec. 30, 2014, which is incorporated in its entirety herein by reference.

FIELD OF THE INVENTION

The disclosure presented herein provides a method for large-scale production of human insulin producing cells, wherein the insulin producing cells comprise transdifferentiated non-pancreatic β-cell cells that produce insulin in a glucose regulated manner.

BACKGROUND OF THE INVENTION

The beta-cells of the islets of Langerhans in the pancreas secrete insulin in response to factors such as amino acids, glyceraldehyde, free fatty acids, and, most prominently, glucose. The capacity of normal islet beta-cells to sense a rise in blood glucose concentration and to respond to elevated levels of glucose by secreting insulin is critical to the control of blood glucose levels. Increased insulin secretion in response to a glucose load prevents hyperglycemia in normal individuals by stimulating glucose uptake into peripheral tissues, particularly muscle and adipose tissue.

Individuals in whom islet beta-cells function is impaired suffer from diabetes. Insulin-dependent diabetes mellitus, or IDDM (also known as Juvenile-onset or Type I diabetes), represents approximately 10% of all human diabetes. IDDM is distinct from non-insulin dependent diabetes (NIDDM) in that only IDDM involves specific destruction of the insulin producing beta cells of the islets of Langerhans. The destruction of beta-cells in IDDM appears to be a result of specific autoimmune attack, in which the patient's own immune system recognizes and destroys the beta-cells, but not the surrounding alpha-cells (glucagon producing) or delta-cells (somatostatin producing) that comprise the islet.

Treatment options for IDDM are centered on self-injection of insulin, which is an inconvenient and imprecise solution. Thus the development of new therapeutic strategies is highly desirable. The possibility of islet or pancreas fragment transplantation has been investigated as a means for permanent insulin replacement. Current methodologies use either cadaverous material or porcine islets as transplant substrates. However, significant problems to overcome are the low availability of donor tissue, the variability and low yield of islets obtained via dissociation, and the enzymatic and physical damage that may occur as a result of the isolation process. In addition, there are issues of immune rejection and current concerns with xenotransplantation using porcine islets.

It is clear that there remains a critical need to establish alternatives to the treatment of diabetes by self-injection of insulin. While stem cell research has shown promise in this regard, there has not been great success. There is a need for improved procedures for isolating, culturing, and transdifferentiating non-pancreatic cells to be used in the treatment of diabetes. The methods disclosed herein comprise large-scale production of transdifferentiated non-beta pancreatic cells that secrete insulin. These transdifferentiated cells may be used in transplant therapies, obviating the need for the numerous self-injections of insulin, now required for the treatment of diabetes.

SUMMARY OF THE INVENTION

In one aspect, disclosed herein is a method of manufacturing a population of human insulin producing cells, the method comprising the steps of: obtaining adult human liver tissue; processing said liver tissue to recover primary adult human liver cells; propagating and expanding said primary adult human liver cells to a predetermined number of cells; transdifferentiating said expanded cells; and harvesting said transdifferentiated expanded culture; thereby manufacturing said population of human insulin producing cells having an increased insulin content, or increased glucose regulated secretion, or any combination thereof, compared with control non-transdifferentiated liver cells.

In a related aspect, greater than 70% of said population of human insulin producing cells expresses endogenous PDX-1. In a further related aspect the cells expressing PDX-1 also express endogenous NeuroD1 or MafA, or any combination thereof. In yet another related aspect, less than 5% of the population expressing PDX-1 expresses albumin and alpha-1 anti-trypsin.

In a related aspect, the increased insulin content of the cells produced comprises an at least 5% increase compared with said control cells that are not transdifferentiated.

In another aspect, the liver tissue is obtained from a subject suffering from pancreatitis or from insulin dependent diabetes. In a related aspect, the population of human insulin producing cells is autologous for a patient in need of such an insulin therapy. In another related aspect, the population of human insulin producing cells is allogeneic for a patient in need of such an insulin therapy.

In a related aspect, the method comprises propagating and expanding said liver cells through a series of sub-cultivation steps up to a production-bioreactor system. In another related aspect, the bioreactor system comprises a single bioreactor or multiple bioreactors. In another related aspect, the bioreactor comprises a single use bioreactor, a multi-use bioreactor, a closed system bioreactor, or an open system bioreactor, or any combination thereof. In a further related aspect, the transdifferentiating of said expanded cells comprises transdifferentiation through a series of bioreactor systems.

In a related aspect, the transdifferentiating comprises: infecting said expanded cells with an adenoviral vector comprising a nucleic acid encoding a human PDX-1 polypeptide, said infecting at a first time period; infecting said expanded cells of (a) with an adenoviral vector comprising a nucleic acid encoding a human NeuroD1 polypeptide or Pax4 polypeptide, said infecting at a second time period; and infecting said expanded cells of (b) with an adenoviral vector comprising a nucleic acid encoding a human MafA polypeptide, said infecting at a third time period.

In another related aspect, the transdifferentiating comprises: infecting said expanded cells with an adenoviral vector comprising a nucleic acid encoding a human PDX-1 polypeptide and encoding a second pancreatic transcription factor polypeptide, said infecting at a first time period; and infecting said expanded cells of (a) with an adenoviral vector comprising a nucleic acid encoding a human MafA polypeptide, said infecting at a second time period. In a further related aspect, the second pancreatic transcription factor is selected from NeuroD1 and Pax4.

In another related aspect, the method further comprises enriching said primary adult human liver cells for cells predisposed to transdifferentiation. In a further related aspect, the predisposed cells comprise pericentral liver cells. In yet another related aspect, the predisposed cells comprise cells comprising: an active Wnt-signaling pathway; a capability of activating the glutamine synthetase response element (GSRE); increased expression of HOMER1, LAMP3, ITGA6, DCBLD2, THBS1, VAMP4, or BMPR2, or any combination thereof; decreased expression of ABCB1, ITGA4, ABCB4, or PRNP, or any combination thereof; or any combination thereof.

In another related aspect, the method further comprises treating the primary adult human liver cell population with lithium, wherein said treated population is enriched in cells predisposed to transdifferentiation. In another related aspect, treating with lithium occurs prior to transdifferentiation.

In one aspect, disclosed herein is a population of human insulin producing cells manufactured by a method comprising the steps of: obtaining adult human liver tissue; processing said liver tissue to recover primary adult human liver cells; propagating and expanding said primary adult human liver cells to a predetermined number of cells; transdifferentiating said expanded cells; and harvesting said transdifferentiated expanded culture; wherein said population of human insulin producing cells have an increased insulin content or increased glucose regulated insulin secretion, or any combination thereof, compared with control non-transdifferentiated liver cells.

In another related aspect, greater than 70% of the population of human insulin producing cells expresses endogenous PDX-1. In a further related aspect, the cells expressing PDX-1 also express endogenous NeuroD1 or MafA, or any combination thereof. In yet another related aspect, less than 5% of the population expressing PDX-1 expresses albumin and alpha-1 anti-trypsin.

In another related aspect, the population of human insulin producing cells comprises an increased insulin content comprising an at least 5% increase compared with said control cells.

In another related aspect, the population of human insulin producing cells is for use in a cell-based therapy for a patient suffering from pancreatitis or from insulin dependent diabetes. In a further related aspect, the cells are autologous or allogeneic with the patient.

In another aspect, disclosed herein is a composition comprising a population of human insulin producing cells, and a pharmaceutically acceptable carrier.

BRIEF DESCRIPTION OF THE DRAWINGS

The subject matter regarded as transdifferentiated non-beta pancreatic cells having the phenotype and function of pancreatic cells and methods of manufacturing the same is particularly pointed out and distinctly claimed in the concluding portion of the specification. The transdifferentiated non-beta pancreatic cells having the phenotype and function of pancreatic cells, however, both as to organization and method of operation, together with objects, features, and advantages thereof, may best be understood by reference to the following detailed description when read with the accompanying drawings in which:

(FIG. 1A) Insulin (INS); (FIG. 1B) glucagon (GCG); (FIG. 1C) somatostatin (SST); and (FIG. 1D) other pancreas-specific transcription factors ("pTFs") (NKX6.1, ISL1, PAX4, MAFA, NeuroD1, NeuroG3). The results were normalized to β-actin gene expression within the same cDNA sample and are presented as the mean±SE of the relative expression versus control virus treated cells on the same day. n≥4 in two independent experiments (*p<0.05, **p<0.01).

FIGS. 2A-2D show that ectopic co-expression of pancreatic transcription factors (pTFs) PDX-1, Pax4, and MafA in human liver cells in vitro promotes (pro)insulin secretion, compared to that induced by each of the pTFs alone. (FIG. 2A) Immunofluorescence (IF) staining shows expression of pTFs: PDX-1 (left panel), Pax4 (middle left panel), MafA (middle right panel) and a merge of the 3 pTFs (right panel), with arrows indicating cells expressing all three pTFs. (FIG. 2B) Luciferase assay insulin promoter activation by the indicated pTFs; β-gal was used as a control. Results are expressed as Relative Light Unit (RLU)/mg protein. Each data point represents the mean±SE of at least two independent experiments, *p<0.05, **p<0.01 in comparison to control virus treated cells, (n>4). (FIG. 2C) Immunofluorescence staining shows insulin-positive cells after ectopic expression of the indicated pTFs. Original magnification ×20. Quantification of IF staining in table (right). The percent of insulin-positive cells was calculated by counting at least 500 positive cells from at least two independent experiments. (FIG. 2D) Insulin secretion after incubation with the indicated concentrations of glucose was detected by radioimmunoassay. *p<0.05, n>12 in five independent experiments. The significance represents the differences between triple infection and all other treatments.

FIGS. 3A-3E show the effects of concerted and sequential expression of pTFs PDX-1, Pax4, and MafA on pancreatic β-cell maturation. (FIG. 3A) A schematic demonstrating the order of infection of pTFs (treatments B-E) or control virus (Ad-CMV-β-gal, treatment A). (FIG. 3B) Immunofluorescence staining for insulin: treatment B (left panel), treatment C (middle panel), treatment D (right panel). Original magnification is at ×20. Quantification of staining (percent) is indicated below each image. The percent of insulin positive cells were calculated by counting at least 1000 positive cells from at least two independent experiments. (FIG. 3C) Insulin and (FIG. 3D) C-peptide secretion after incubation with the indicated concentration of glucose was measured by radioimmunoassay. Infection treatments are indicated on the X-axis and explained in FIG. 3A. *p<0.05, **p<0.01, compared to control virus treated cells; n>12 in 5 independent experiments. (FIG. 3E) Expression levels of the indicated endogenous pancreas-specific transcription factors after the indicated treatments (X-axis) were measured by RT-PCR. CT values are normalized to β-actin gene expression within the same cDNA sample. Results are presented as relative levels of the mean+SE of the relative expression versus control virus treated cells, *p<0.05 n>8 in 4 independent experiments. The arrow points the specific decrease in Isl-1 expression level under treatment C.

(FIG. 4A) Insulin promoter activation was measured by luciferase assay after the indicated infection treatments. Results are expressed as Relative Light Unit (RLU)/mg protein. Each data point represents the mean±SE of at least two independent experiments, *P<0.05, **P<0.01, compared to control virus treated cells, (n>4). (FIG. 4B) Analysis of glucose transporter 2 (GLUT2) expression levels by RT-PCR was performed after the indicated infection treatments. CT values are normalized to β-actin gene expression within the same cDNA sample. Results are presented as relative levels of the mean+SE compared to control virus treated cells. *$P<0.05$, compared to control virus treated cells $n>8$ in 4 independent experiments. (FIG. 4C) Expression levels of prohormone convertase 2 (PC2; PCSK2) were determined by RT-PCR after the indicated infection treatments. CT values are normalized to β-actin gene expression within the same cDNA sample. Results are presented as relative levels of the mean+SE compared to control virus treated cells **$P<0.01$, $n>8$ in 4 independent experiments.

(FIG. 5A) C-peptide secretion was measured by radioimmunoassay static incubation for 15 min at 0, 5, 10, 15, 20 mM glucose in cells treated by the direct "hierarchical" sequential order (treatment C) *$P<0.05$, $n>7$ in 3 independent experiments. (FIG. 5B) C-peptide secretion was measured by radioimmunoassay over 13 or 28 days in serum free media supplemented with insulin, transferrin and selenium (ITS), before being analyzed for C-peptide secretion. *$P<0.05$,**$P<0.01$, $n>5$ in 2 independent experiments. The significance represents the differences compared to the standard protocol (treatment C on day 6).

FIGS. 6A-6D present four graphs showing the individual role of the pTFs in the transdifferentiation process, using treatment C infection order and exclusion of each pTF (C-PDX-1, exclusion of PDX-1; C-Pax4, exclusion of Pax4; and C-MafA, exclusion of MafA). (FIG. 6A) Insulin promoter activation was measured by luciferase assay. Results are presented mean±SE, *$p<0.1$, **$p<0.05$ compared to the direct "hierarchical" sequential infection order (treatment C), $n>6$ in three independent experiments. (FIG. 6B) C-peptide secretion after incubation for 15 minutes with the indicated concentrations of glucose and measured by radioimmunoassay. *$=p<0.05$, **$=p<0.01$ is compared to the direct "hierarchical" sequential infection order (C), $n>6$ in three independent experiments. (FIG. 6C) Expression levels of pancreatic enzymes were measured by RT-PCR: glucose transporter 2 (GLUT2); glucokinase (GCK); and prohormone convertase (PCSK2). (FIG. 6D) Expression levels of the indicated endogenous pTFs were measured by RT-PCR. CT values are normalized to β-actin gene expression within the same cDNA sample. Results are presented as relative levels of the mean+SE compared to "hierarchy sequential infection" treated liver cells. *$p<0.05$, **$p<0.01$, $n>6$ in three independent experiments.

(FIG. 7A) Expression levels of insulin were measured by RT-PCR. CT values are normalized to β-actin gene expression within the same cDNA sample. Results are presented as relative levels of the mean+SE compared to control virus treated cells. *$P<0.05$, $n>6$ in 3 independent experiments. (FIG. 7B) Insulin secretion was measured by radioimmunoassay. **$P<0.01$, $n>6$ and compared to the direct "hierarchical" sequential infection order (C), $n>6$ in 3 independent experiments. (FIG. 7C) Expression level of glucose transporter 2 (GLUT2) was measured by RT-PCR.

FIGS. 8A-8G shows the individual role of pTFs in promoting the differentiation of cells to produce glucagon (α-cells) and somatostatin (δ-cells) using hierarchical order of infection (treatment C) and exclusion of each pTF. Expression levels of pancreatic hormones glucagon (GCG) (FIGS. 8A and 8B) and somatostatin (SST) (FIGS. 8A and 8D) were determined by RT-PCR after the indicated infection treatments. (FIG. 8C) Expression levels of cell-specific transcription factors ARX and BRAIN4 were also measured by RT-PCR for the indicated infection treatments. (FIG. 8E) Expression levels of somatostatin (SST) were determined by RT-PCR after additional infection with Isl1 (100 MOI). CT values (for FIGS. 8A, 8B, 8C, and 8D) are normalized to β-actin gene expression within the same cDNA sample. Results are presented as relative levels of the mean+SE compared to control virus treated cells (FIG. 8A) or to "hierarchy sequential infection" treated liver cells (FIGS. 8B-8E). *$P<0.05$, **$P<0.1$, $n>6$ in 3 independent experiments. (FIG. 8F) Immunofluorescence staining for somatostatin after treatment C infection (left panel), and after treatment C infection with additional Isl1 infection (right panel). Original magnification ×20. (FIG. 8G) Immunofluorescence staining for somatostatin and insulin showing that the sequential administration of transcription factors in a direct hierarchical manner results in increased maturation of the transdifferentiated cells along the beta-like-pancreatic lineage.

(FIGS. 10C and 10D) analysis of GS expression in human (FIG. 10C) and mice (FIG. 10D) livers indicating the expression of GS at the 1-2 cell layers adjacent to the central veins. Original magnification ×400.

FIGS. 12A-12F shows that the GSRE targets subpopulation of human liver cells in vitro. (FIGS. 12A and 12D) Schematic presentations of Ad-GSRE-TK-PDX-1 or GFP recombinant adenoviruses. Liver cells were infected with Ad-GSRE-TK-Pdx-1 (FIG. 12C) or with Ad-CMV-Pdx-1 (FIG. 12B). Immunofluorescent analysis of PDX-1 expression indicated that 13±2% of the human liver cells infected by Ad-GSRE-TK-Pdx-1 (FIG. 12C) while 70±12% of Ad-CMV-Pdx-1-treated cells (FIG. 12B) expressed the ectopic nuclear factor (rabbit anti-Pdx-1, generous gift from C. Wright, pink; FIGS. 12B and 12C, respectively) Similar results were obtained using Ad-GSRE-TK-eGFP; ~15% of the cells were positive to eGFP (FIGS. 12E and 12F). Ad-CMV-eGFP infection resulted in about 75-80% eGFP positive cells within 3-4 days (data not presented).

FIGS. 13A-13C show that the GSRE targets transdifferentiation-prone cells. Liver cells were infected with Ad-GSRE-TK-Pdx-1 (FIG. 13B) or with Ad-CMV-Pdx-1 (FIG. 13A) for 5 days. (FIGS. 13A and 13B), immunofluorescent analysis of co-staining of insulin (Guinea pig anti-insulin, Dako, green) and (Pdx-1 rabbit anti-Pdx-1, generous gift from C. Wright, pink). (FIG. 13C) Statistical analysis of activation of insulin in the treated cells; Ad-GSRE-TK- Pdx-1 activated insulin production in 50%, whereas Ad-CMV-Pdx-1 only in 5% of the Pdx-1-positive cells. Blue—DAPI, nuclear staining; original magnification ×20.

FIGS. 14A-14E show in vitro lineage tracing for GSRE activating human cells. (FIG. 14A) A schematic presentation of the lentivirus vectors. (FIG. 14B) Adult human liver cells at passages 3-10 were infected with the dual lentivirus system. Liver cells were imaged 10 days after infection for DsRed2 (red) or eGFP (green) fluorescence. (FIG. 14C) The cells were sorted by a fluorescence-activated cell sorter (FACS; Aria cell sorter; Becton Dickinson, San Jose, Calif.) with a fluorescein isothiocyanate filter (530/30 nm) for eGFP and a Pe-Texas Red filter (610/20 nm) for DsRed2. (FIGS. 14D and 14E). The separated cells were cultured separately for several passages (original magnification ×10).

FIGS. 15A-15E show eGFP+ and DsRed2+ cells efficiently proliferate in vitro with a similar rate of proliferation and similar infection capacity. The separate populations of cells were cultured separately for ~1 month. The proliferation rate of each group was analyzed (FIG. 15A) eGFP+ (FIGS. 15B and 15C) and DsRed2+(FIGS. 15D and 15E) cells were infected with Ad-CMV-β-gal (FIGS. 15B and 15D) or with Ad-CMV-Pdx-1 (FIGS. 15C and 15E) for 3 days. Immunofluorescent analysis using anti-Pdx-1 (blue) indicated that almost 80% of both eGFP and DsRed2 cells were infected by the adenovirus.

(FIG. 16A) at the molecular level, insulin and glucagon gene expression was studied by Quantitative real-time PCR compared to the control-treated cells. Cultured pancreatic human islet cells (Passage 3) were used as a positive control. (FIGS. 16B and 16C) At the functional level, glucose-regulated insulin secretion was analyzed by static incubations at low glucose concentrations followed by high glucose concentrations (2 mM and 17.5 mM glucose in Krebs-Ringer buffer (KRB), respectively). Insulin (FIG. 16B) and C-peptide (FIG. 16C) secretion were measured using the human insulin radioimmunoassay kit (DPC; n>8 from 3 different experiments) or human C-peptide radioimmunoassay kit (Linco n>8 from 3 different experiments. *P<0.01 compared to the DsRed2+ cells, using Student's t-test analysis).

(FIG. 21A) APC and DKK1 expression is markedly increased in DsRed2+ cells. This may further suggest that these cells express higher levels of Wnt signaling pathway repressors compared with the eGFP+ cells. n≥6 from 2 different experiments *p<0.01 in DsRed2+ compared to eGFP+ cells, using Student's t-test analysis. (FIG. 21B) Western blot analysis using a specific antibody for activated β-catenin (anti-ABC clone 8E7, Millipore, 1:2000) in eGFP and DsRed2 positive cell extracts. β-actin (SC-1616, Santa Cruz, 1:1000) was used as a normalizing protein. (FIG. 21C) Quantification of the β-catenin protein levels was performed using ImageJ 1.29× software. Activated β-actin (SC-1616, Santa Cruz, 1:1000) was used as a normalizing protein.

FIGS. 24A-24B present the combined insulin secretion measurements of naïve and GS enriched populations of cells on day 6 of the experiment comparing the effect of PAX4 versus NeuroD1. FIG. 24A presents a bar graph of insulin secretion in response to low (2 mM) and high (17.5 mM) concentrations of glucose as Nano grams insulin per million cells per hour (ng/$10^6$/hr). FIG. 24B presents a bar graph of insulin secretion in response to low (2 mM) and high (17.mM) concentrations of glucose as Nano grams insulin per hour (ng/hr).

FIGS. 25A-25D present the individual insulin secretion measurements of naïve and enriched populations of cells on day 6 of the experiment comparing the effect of PAX4 versus NeuroD1. FIG. 25A (enriched for GS expression) and FIG.

25C (Naïve) present bar graphs of insulin secretion in response to low (2 mM) and high (17.mM) concentrations of glucose as Nano grams insulin per million cells per hour (ng/$10^6$/hr). FIG. 25B (enriched for GS expression) and FIG. 25D (Naïve) presents a bar graph of insulin secretion in response to low (2 mM) and high (17.mM) concentrations of glucose as Nano grams insulin per hour (ng/hr).

FIGS. 26A-26C show insulin secretion measured on day 6 of the experiment following incubation with 2 mM glucose (low concentration) or 17.5 mM glucose (high concentration). Results are presented as Nano grams insulin per million cells per hour (ng INS/$10^6$/hr) for primary liver cells obtained from human donors (FIG. 26A Muhammad, FIG. 26B Pedro, and FIG. 26C Leon).

FIGS. 31A and 31C show cells from the Xpansion 50 bioreactor run, while FIG. 31B and FIG. 31D show cells from the Xpansion 200 bioreactor run.

FIG. 35 presents the variability of cell density at harvest from cells manufactured during three individual runs, wherein the starting densities are comparable.

FIGS. 41A-41D present micrographs of cell densities at day 8 at the time of the final harvest, including an image of untreated control cells.

FIGS. 42A-42B present micrographs of cell densities at day 8 at the time of final harvest from plates 3 (FIG. 42A) and 5 (FIG. 42B) of the Xpansion-10 multi-system bioreactor.

FIG. 44A shows a representative FACS plot of several mesenchymal stem cells (MSC) markers, gated on live cells. Markers shown include CD90, CD73, CD105, and CD44. The Negative cocktail includes hematopoietic markers. FIG. 44B shows the frequency of the MSC markers at different cell passages, P12 ($12^{th}$ passage), P13 ($13^{th}$ passage), P14 ($14^{th}$ passage), and in infected cells (P16_AdV infection).

FIG. 45A fluorescent micrographs, FIG. 45B FACS, and FIG. 45C Summary of FACS data.

FIG. 46A fluorescent micrographs, FIG. 46B FACS, and FIG. 46C Summary of FACS data.

FIG. 48A bar graph shows fold increase of insulin following transdifferentiation without pre-treatment of lithium (left) and with pre-treatment of lithium 48 hours prior to transdifferentiation (right). (FIGS. 48B and 48C). Expression levels of pancreatic genes Nkx6.1, Isl-1, and human PDX1 were measured by Real-Time PCR, and normalized to actin. Results are representative of two donors.

Figures 1A, 1B, 1C, 1D:
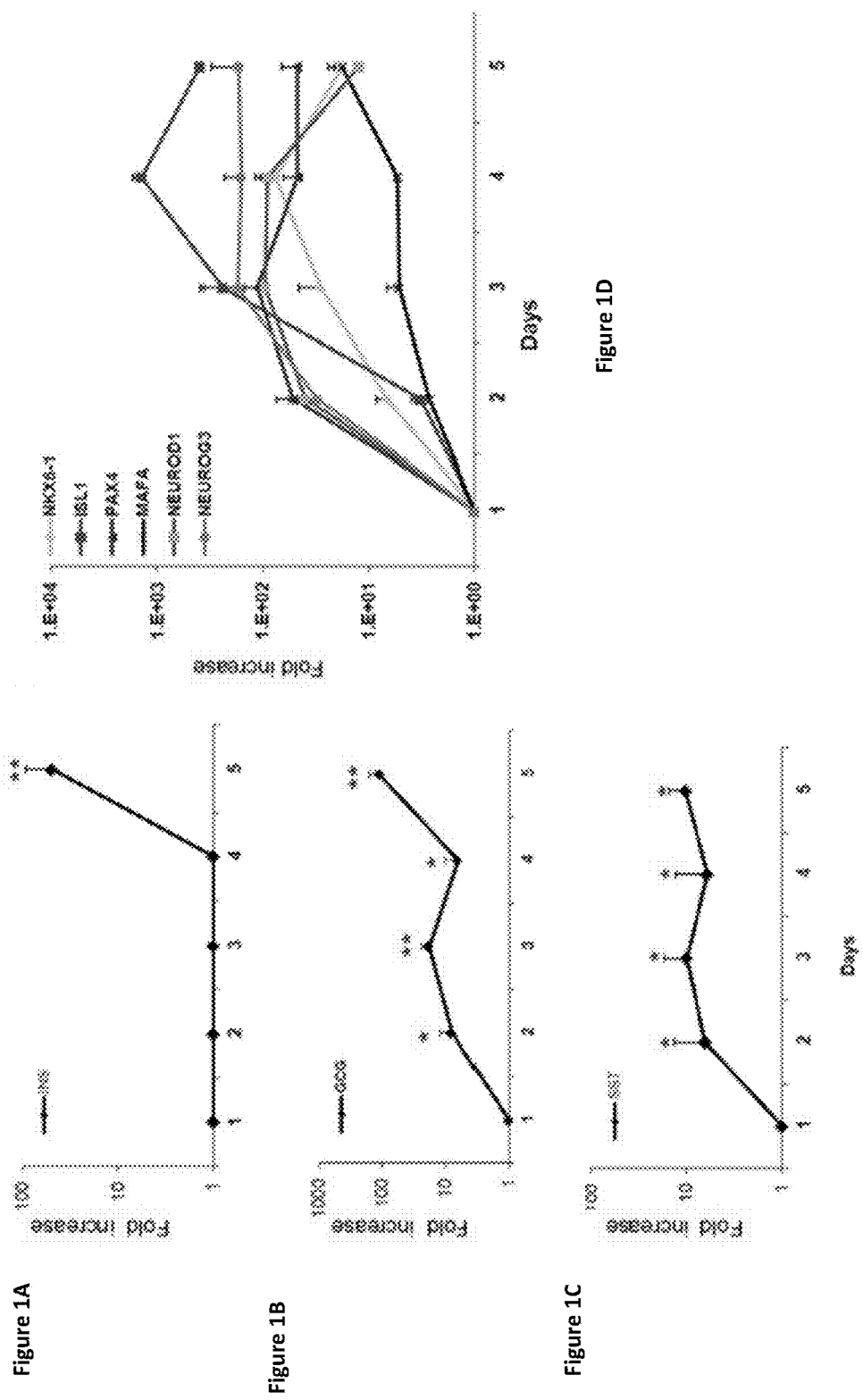
FIGS. 1A-1D show that PDX-1 expression in human liver cells in vitro induces gradual activation of pancreatic hormone expression.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

In the following detailed description, numerous specific details are set forth in order to provide a thorough understanding of the non-pancreatic transdifferentiated human insulin producing cells having pancreatic cell phenotype and functions, and methods of manufacturing the same. In other instances, well-known methods, procedures, and components have not been described in detail so as not to obscure the non-pancreatic transdifferentiated human insulin producing cells having pancreatic cell phenotype and functions, and methods of producing the same.

Transcription factors (TFs) have been shown to induce transdifferentiation in numerous cell lineages. A skilled artisan would appreciate that the term "transdifferentiation" may encompass the process by which a first cell type loses identifying characteristics and changes its phenotype to that of a second cell type without going through a stage in which the cells have embryonic characteristics. In some embodiments, the first and second cells are from different tissues or cell lineages. In one embodiment, transdifferentiation involves converting a mature or differentiated cell to a different mature or differentiated cell. Specifically, lineage-specific transcription factors (TFs) have been suggested to display instructive roles in converting adult cells to endocrine pancreatic cells, neurons, hematopoietic cells and cardiomyocyte lineages, suggesting that transdifferentiation processes occur in a wide spectrum of milieus. In all transdifferentiation protocols, the ectopic TFs serve as a short-term trigger to a potential wide, functional and irreversible developmental process. Numerous studies suggested that ectopic expression of individual TFs activate a desired alternate repertoire and function, in a process involved with the activation of additional relevant otherwise silent TFs. However, the time course, the relative levels and the hierarchy, or order, of the induced TFs, remains unknown.

By exploiting the relative insufficiency of the endogenous transcription factor (TFs) induction by introducing individual ectopic TFs, disclosed herein are methods of transdifferentiation as a sequential and temporally controlled process that is affected by a hierarchical network of TFs.

The human insulin producing cell product, and methods thereof of making and producing this product, as disclosed herein are based on the finding that TF-induced liver to pancreas transdifferentiation is a gradual and consecutive process. Importantly, only sequential administration of pancreatic TFs but not their concerted expression selectively drives lineage specification programs within the endocrine pancreas. Sequential expression of pancreatic TFs in a direct hierarchical mode has been shown to be obligatory for transdifferentiated cell maturation along the β-cell lineage. Specifically, a role for the pancreatic β-cell specific transcription factor MafA has been identified in the final stage of the transdifferentiation process. At this stage, MafA promotes the maturation of transdifferentiated liver cells along the β-cell lineage, in a process associated with Isl1 and somatostatin repression. Surprisingly, it was found that a 2+1 hierarchical method (PDX-1 and Pax4 or NeuroD1, followed by MafA) was successful for selectively driving lineage specification towards a pancreatic phenotype and function within non-pancreatic cells.

The findings described herein suggest fundamental temporal characteristics of transcription factor-mediated transdifferentiation which could contribute to increasing the therapeutic merit of using TF-induced adult cell reprogramming for treating degenerative diseases including diabetes.

Pancreatic transcription factor (pTFs), such as Pdx-1, NeuroD1, Ngn-3 and Pax4, activate liver to pancreas transdifferentiation and individually induce amelioration of hyperglycemia in diabetic mice. Moreover, using an in vitro experimental system of adult human liver cells, it was demonstrated that Pdx-1 activates the expression of numerous β-cell specific markers and induces glucose-regulated secretion of processed insulin. The induced process was associated with the expression of numerous key endogenous pTFs and amelioration of hyperglycemia was demonstrated upon transplantation of the transdifferentiated adult human liver cells in diabetic mice. However, numerous other studies have indicated that using combinations of several key TFs markedly increases the reprogramming efficiency compared to that induced by the ectopic expression of individual TFs. This suggests a potential restricted capacity of the individual ectopic factors to activate the endogenous complementing TFs to sufficient levels needed for an efficient transdifferentiation process. Targeted disruption or temporal mis-expression of pancreatic transcription factors during pancreas organogenesis hampers pancreas development as well as islet cells differentiation and function. By exploiting the relative insufficiency of the endogenous TFs induction by individual ectopic TFs, the disclosure presented herein is related to transdifferentiation as a sequential and temporally controlled process that is affected by a hierarchical network of TFs.

Pancreatic specification is initiated by the homeobox transcription factor Pdx1, which is also required for β-cell function in adults. The endocrine differentiation is then mediated by the basic helix-loop-helix factor Ngn3. The paired homeobox factors Pax4 and Arx, have been implicated as key factors in the segregation of the different endocrine cell types. The final maturation along the β-cell lineage and function is attributed to selective expression of MafA in β-cells in the adult pancreas.

Disclosed herein are methods and human insulin producing cells produced using these methods, based in part on the surprising finding that human liver cells can be directly transdifferentiated to produce an entirely different cell type, pancreatic hormones producing cells including beta cells. Application of select transcription factors in a temporally regulated sequence induced the transdifferentiation of adult liver cells to functional mature beta cells. The methods described herein solve the problem of producing large populations of insulin-producing cells, or pancreatic beta cells, by providing methods for expanding and transdifferentiating adult cells. The compositions comprising the select transcription factors or the generated population of transdifferentiated pancreatic cells can be used for treating a pancreatic disorder using the methods described herein.

Previous efforts to transdifferentiate non-pancreatic cells to pancreatic cells, such as beta cells, utilize either only one transcription factor or the concerted or simultaneous administration of more than one pancreatic transcription factor.

The methods disclosed herein provide for an ordered, sequential administration of specific transcription factors at defined time points. Alternative methods disclosed herein, provide for a "two pTFs+one pTF" (2+1) combined and ordered, sequential administration of specific transcription factors at defined time points. Furthermore, the methods described herein substantially increase the transdifferentiation efficiency compared to that induced by each of the individual transcription factors alone.

Disclosed herein is a population of cells that possess increased transdifferentiation capacity. These cells are characterized by (1) potential cell membrane markers, (2) possessing the capacity to activate glutamine synthetase regulatory element (GSRE), and (3) by being uniquely equipped with active Wnt-signaling. At least 30% of the cells in the population are capable of activating GSRE. For example the cells are endothelial cells, epithelial cells, mesenchymal cells, fibroblasts, or liver cells. In one embodiment, the cells are human cells. In some embodiments, the cells can be transdifferentiated along the pancreatic lineage to mature pancreatic cells with pancreatic function. In other embodiments, the cells can be transdifferentiated along the neural lineage to neural cells.

Thus, methods disclosed herein solve the problem of previous transdifferentiation or reprogramming protocols that often have restricted efficiency. For example, although ectopic expression of key pancreatic transcription factors results in expression in each host cell, only up to 15% of the cells are successfully transdifferentiated to exhibit pancreatic function.

Further, disclosed herein are methods for isolating the population of cells with enriched or increased transdifferentiation capacity. For example, one method for isolating these cells is by sorting out cells that activate GFP expression operatively linked to the glutamine synthetase regulatory element, or a fragment thereof, thereby isolating those cells that can activate GSRE. The cells may be sorted by FACS and can be propagated in culture, separately from the rest of the cells, for rapid expansion of the cells with enriched transdifferentiation capacity. The population of cells with enriched capacity for transdifferentiation is only a small proportion of the cells that make up the tissue in vivo. For example, in a given tissue or population of cells, the population of cells with enriched capacity for transdifferentiation is only about less than 1%, 2%, 3%, 4%, 5%, about 10%, about 15%, of the entire population of cells in a given tissue. Therefore, methods are disclosed herein for the isolation of said cells with increased transdifferentiation capacity from cells that do not have increased transdifferentiation capacity. Accordingly, the enriched non-pancreatic β-cells, disclosed herein have the advantage of a cell population with a greater proportion of cells that have increased transdifferentiation capacity to increase the efficiency of transdifferentiation to provide transdifferentiated cells for treatment of various diseases or disorders.

It will be obvious to those skilled in the art that various changes and modifications may be made to the methods described herein within the spirit and scope of the non-pancreatic β-cells transdifferentiation human insulin producing cell product, and methods of making and using said product.

Methods of Producing Pancreatic Beta-Cells

Disclosed herein are methods for producing cells that exhibit a mature pancreatic beta cell phenotype by contacting mammalian non-pancreatic cells with pancreatic transcription factors, such as PDX-1, Pax-4, NeuroD1, and MafA, at specific time points. In some embodiments, the methods comprise contacting a mammalian non-pancreatic cell with PDX-1 at a first time period; contacting the cells from the first step with Pax-4 at a second time period; and contacting the cells from the second step with MafA at a third time period. In one embodiment, the methods comprise contacting a mammalian non-pancreatic cell with PDX-1 at a first time period; contacting the cells from the first step with NeuroD1 at a second time period; and contacting the cells from the second step with MafA at a third time period. In another embodiment, the methods comprise contacting a mammalian non-pancreatic cell with PDX-1 and a second transcription factor at a first time period and contacting the cells from the first step with MafA at a second time period. In yet a further embodiment, a second transcription factor is selected from NeuroD1 and Pax4. In another embodiment, the transcription factors provided together with PDX-1 comprise Pax-4, NeuroD1, Ngn3, or Sox-9. In another embodiment, the transcription factors provided together with PDX-1 comprises Pax-4. In another embodiment, the transcription factors provided together with PDX-1 comprises NeuroD1. In another embodiment, the transcription factors provided together with PDX-1 comprises Ngn3. In another embodiment, the transcription factors provided together with PDX-1 comprises Sox-9.

In other embodiments, the methods comprise contacting a mammalian non-pancreatic cell with PDX-1 at a first time period; contacting the cells from the first step with Ngn3 at a second time period; and contacting the cells from the second step with MafA at a third time period. In other embodiments, the methods comprise contacting a mammalian non-pancreatic cell with PDX-1 at a first time period; contacting the cells from the first step with Sox9 at a second time period; and contacting the cells from the second step with MafA at a third time period. In another embodiment, the methods comprise contacting a mammalian non-pancreatic cell with PDX-1 and a second transcription factor at a first time period and contacting the cells from the first step with MafA at a second time period, wherein a second transcription factor is selected from NeuroD1, Ngn3, Sox9, and Pax4.

In another embodiment, the methods comprise contacting a mammalian non-pancreatic cell with PDX-1 and NeuroD1 at a first time period, and contacting the cells from the first step with MafA at a second time period. In another embodiment, the methods comprise contacting a mammalian non-pancreatic cell with PDX-1 and Pax4 at a first time period, and contacting the cells from the first step with MafA at a second time period. In another embodiment, the methods comprise contacting a mammalian non-pancreatic cell with PDX-1 and Ngn3 at a first time period, and contacting the cells from the first step with MafA at a second time period. In another embodiment, the methods comprise contacting a mammalian non-pancreatic cell with PDX-1 and Sox9 at a first time period, and contacting the cells from the first step with MafA at a second time period.

In another embodiment, the cells are contacted with all three factors (PDX-1; NeuroD1 or Pax4 or Ngn3; and MafA) at the same time but their expression levels are controlled in such a way as to have them expressed within the cell at a first time period for PDX-1, a second time period for NeuroD1 or Pax4 or Ngn3; and a third time period for MafA. The control of expression can be achieved by using appropriate promoters on each gene such that the genes are expressed sequentially, by modifying levels of mRNA, or by other means known in the art.

In one embodiment, the methods described herein further comprise contacting the cells at, before, or after any of the above steps with the transcription factor Sox-9.

In one embodiment, the first and second time periods are identical resulting in contacting a cell population with two pTFs at a first time period, wherein at least one pTF comprises pDX-1, followed by contacting the resultant cell population with a third pTF at a second time period, wherein said third pTF is MafA.

In one embodiment, the second time period is at least 24 hours after the first time period. In an alternative embodiment, the second time period is less than 24 hours after the first time period. In another embodiment, the second time period is about 1 hour after the first time period, about 2 hours, about 3 hours, about 4 hours, about 5 hours, about 6 hours, about 7 hours, about 8 hours, about 9 hours, about 10 hours, about 11 hours, or about 12 hours after the first time period. In some embodiments, the second time period can be at least 24 hours, at least 48 hours, at least 72 hours, and at least 1 week or more after the first time period.

In another embodiment, the third time period is at least 24 hours after the second time period. In an alternative embodiment, the third time period is less than 24 hours after the second time period. In another embodiment, the third time period is at the same time as the second time period. In another embodiment, the third time period is about 1 hour after the second time period, about 2 hours, about 3 hours, about 4 hours, about 5 hours, about 6 hours, about 7 hours, about 8 hours, about 9 hours, about 10 hours, about 11 hours, or about 12 hours after the second time period.

In other embodiments, the third time period can be at least 24 hours, at least 48 hours, at least 72 hours, and at least 1 week or more after the second time period.

In one embodiment, the first, second, and third time periods are concurrent resulting in contacting a cell population with three pTFs at a single time period, wherein at least one pTF comprises pDX-1, at least one pTF comprises NeuroD1 or Pax4, and at least one pTF comprises MafA. In another embodiment, the first, second, and third time periods are concurrent resulting in contacting a cell population with three pTFs at a single time period, wherein one pTF consists of pDX-1, one pTF consists of NeuroD1 or Pax4, and one pTF consists of MafA.

In one embodiment, transcription factors comprise polypeptides, or ribonucleic acids or nucleic acids encoding the transcription factor polypeptides. In another embodiment, the transcription factor comprises a polypeptide. In another embodiment, the transcription factor comprises a nucleic acid sequence encoding the transcription factor. In another embodiment, the transcription factor comprises a Deoxyribonucleic acid sequence (DNA) encoding the transcription factor. In still another embodiment, the DNA comprises a cDNA. In another embodiment, the transcription factor comprises a ribonucleic acid sequence (RNA) encoding the transcription factor. In yet another embodiment, the RNA comprises an mRNA.

Transcription factors for use in the disclosure presented herein can be a polypeptide, ribonucleic acid or a nucleic acid. A skilled artisan would appreciate that the term "nucleic acid" may encompass DNA molecules (e.g., cDNA or genomic DNA), RNA molecules (e.g., mRNA, microRNA or other RNA derivatives), analogs of the DNA or RNA generated using nucleotide analogs, and derivatives, fragments and homologs thereof. The nucleic acid molecule can be single-stranded or double-stranded. In one embodiment, the nucleic acid is a DNA. In other embodiments the nucleic acid is mRNA. mRNA is particularly advantageous in the methods disclosed herein, as transient expression of PDX-1 is sufficient to produce pancreatic beta cells. The polypeptide, ribonucleic acid or nucleic acid maybe delivered to the cell by means known in the art including, but not limited to, infection with viral vectors, electroporation and lipofection.

In certain embodiments, transcription factors for use in the methods described herein are selected from the group consisting of PDX-1, Pax-4, NeuroD1, and MafA. In other embodiments, transcription factors for use in the methods described herein are selected from the group consisting of PDX-1, Pax-4, NeuroD1, MafA, Ngn3, and Sox9.

The homeodomain protein PDX-1 (pancreatic and duodenal homeobox gene-1), also known as IDX-1, STF-1, or IUF-1, plays a central role in regulating pancreatic islet development and function. PDX-1 is either directly or indirectly involved in islet-cell-specific expression of various genes such as, for example insulin, glucagon, somatostatin, proinsulin convertase 1/3 (PC1/3), GLUT-2 and glucokinase. Additionally, PDX-1 mediates insulin gene transcription in response to glucose. Suitable sources of nucleic acids encoding PDX-1 include for example the human PDX-1 nucleic acid (and the encoded protein sequences) available as GenBank Accession Nos. U35632 and AAA88820, respectively. In one embodiment, the amino acid sequence of a PDX-1 polypeptide is set forth in SEQ ID NO: 4:

```
                                        (SEQ ID NO: 4)
MNGEEQYYAATQLYKDPCAFQRGPAPEFSASPPACLYMGRQPPPPPPH

PFPGALGALEQGSPPDISPYEVPPLADDPAVAHLHHHLPAQLALPHPP

AGPFPEGAEPGVLEEPNRVQLPFPWMKSTKAHAWKGQWAGGAYAAEPE

ENKRTRTAYTRAQLLELEKEFLFNKYISRPRRVELAVMLNLTERHIKI

WFQNRRMKWKKEEDKKRGGGTAVGGGGVAEPEQDCAVTSGEELLALPP

PPPPGGAVPPAAPVAAREGRLPPGLSASPQPSSVAPRRPQEPR.
```

In one embodiment, the nucleic acid sequence of a PDX-1 polynucleotide is set forth in SEQ ID NO: 5:

```
                                        (SEQ ID NO: 5)
ATGAACGGCGAGGAGCAGTACTACGCGGCCACGCAGCTTTACAAGGAC

CCATGCGCGTTCCAGCGAGGCCCGGCGCCGGAGTTCAGCGCCAGCCCC

CCTGCGTGCCTGTACATGGGCCGCCAGCCCCCGCCGCCGCCGCCGCAC

CCGTTCCCTGGCGCCCTGGGCGCGCTGGAGCAGGGCAGCCCCCCGGAC

ATCTCCCCGTACGAGGTGCCCCCCCTCGCCGACGACCCCGCGGTGGCG

CACCTTCACCACCACCTCCCGGCTCAGCTCGCGCTCCCCCACCCGCCC

GCCGGGCCCTTCCCGGAGGGAGCCGAGCCGGGCGTCCTGGAGGAGCCC

AACCGCGTCCAGCTGCCTTTCCCATGGATGAAGTCTACCAAAGCTCAC

GCGTGGAAAGGCCAGTGGGCAGGCGGCGCCTACGCTGCGGAGCCGGAG

GAGAACAAGCGGACGCGCACGGCCTACACGCGCGCACAGCTGCTAGAG

CTGGAGAAGGAGTTCCTATTCAACAAGTACATCTCACGGCCGCGCCGG

GTGGAGCTGGCTGTCATGTTGAACTTGACCGAGAGACACATCAAGATC

TGGTTCCAAAACCGCCGCATGAAGTGGAAAAAGGAGGAGGACAAGAAG

CGCGGCGGCGGGACAGCTGTCGGGGGTGGCGGGGTCGCGGAGCCTGAG
```

-continued

```
CAGGACTGCGCCGTGACCTCCGGCGAGGAGCTTCTGGCGCTGCCGCCG

CCGCCGCCCCCCGGAGGTGCTGTGCCGCCCGCTGCCCCCGTTGCCGCC

CGAGAGGGCCGCCTGCCGCCTGGCCTTAGCGCGTCGCCACAGCCCTCC

AGCGTCGCGCCTCGGCGGCCGCAGGAACCACGATGA.
```

Other sources of sequences for PDX-1 include rat PDX nucleic acid and protein sequences as shown in GenBank Accession No. U35632 and AAA18355, respectively, and are incorporated herein by reference in their entirety. An additional source includes zebrafish PDX-1 nucleic acid and protein sequences are shown in GenBank Accession No. AF036325 and AAC41260, respectively, and are incorporated herein by reference in their entirety.

Pax-4, also known as paired box 4, paired box protein 4, paired box gene 4, MODY9 and KPD, is a pancreatic-specific transcription factor that binds to elements within the glucagon, insulin and somatostatin promoters, and is thought to play an important role in the differentiation and development of pancreatic islet beta cells. In some cellular contexts, Pax-4 exhibits repressor activity. Suitable sources of nucleic acids encoding Pax-4 include for example the human Pax-4 nucleic acid (and the encoded protein sequences) available as GenBank Accession Nos. NM_006193.2 and AAD02289.1, respectively.

MafA, also known as V-maf musculoaponeurotic fibrosarcoma oncogene homolog A or RIPE3B1, is a beta-cell-specific and glucose-regulated transcriptional activator for insulin gene expression. MafA may be involved in the function and development of beta cells as well as in the pathogenesis of diabetes. Suitable sources of nucleic acids encoding MafA include for example the human MafA nucleic acid (and the encoded protein sequences) available as GenBank Accession Nos. NM_201589.3 and NP_963883.2, respectively. In one embodiment, the amino acid sequence of a MafA polypeptide is set forth in SEQ ID NO: 8:

```
                                       (SEQ ID NO: 8)
MAAELAMGAELPSSPLAIEYVNDFDLMKFEVKKEPPEAERFCHRLPPG

SLSSTPLSTPCSSVPSSPSFCAPSPGTGGGGAGGGGGSSQAGGAPGP

PSGGPGAVGGTSGKPALEDLYWMSGYQHHLNPEALNLTPEDAVEALIG

SGHHGAHHGAHHPAAAAAYEAFRGPGFAGGGGADDMGAGHHHGAHHAA

HHHHAAHHHHHHHHHGGAGHGGGAGHHVRLEERFSDDQLVSMSVREL

NRQLRGFSKEEVIRLKQKRRTLKNRGYAQSCRFKRVQQRHILESEKCQ

LQSQVEQLKLEVGRLAKERDLYKEKYEKLAGRGGPGSAGGAGFPREPS

PPQAGPGGAKGTADFFL.
```

In another embodiment, the nucleic acid sequence of a MafA polynucleotide is set forth in SEQ NO: 9:

```
                                       (SEQ ID NO: 9)
ATGGCCGCGGAGCTGGCGATGGGCGCCGAGCTGCCCAGCAGCCCGCTG

GCCATCGAGTACGTCAACGACTTCGACCTGATGAAGTTCGAGGTGAAG

AAGGAGCCTCCCGAGGCCGAGCGCTTCTGCCACCGCCTGCCGCCAGGC

TCGCTGTCCTCGACGCCGCTCAGCACGCCCTGCTCCTCCGTGCCCTCC

TCGCCCAGCTTCTGCGCGCCCAGCCCGGGCACCGGCGGCGGCGGCGGC

GCGGGGGGCGGCGGCGGCTCGTCTCAGGCCGGGGGCGCCCCCGGGCCG

CCGAGCGGGGGCCCCGGCGCCGTCGGGGGCACCTCGGGGAAGCCGGCG

CTGGAGGATCTGTACTGGATGAGCGGCTACCAGCATCACCTCAACCCC

GAGGCGCTCAACCTGACGCCCGAGGACGCGGTGGAGGCGCTCATCGGC

AGCGGCCACCACGGCGCGCACCACGGCGCGCACCACCCGGCGGCCGCC

GCAGCCTACGAGGCTTTCCGCGGCCCGGGCTTCGCGGGCGGCGGCGGA

GCGGACGACATGGGCGCCGGCCACCACCACGGCGCGCACCACGCCGCC

CACCACCACCACGCCGCCCACCACCACCACCACCACCACCATGGC

GGCGCGGGACACGGCGGTGGCGCGGGCCACCACGTGCGCCTGGAGGAG

CGCTTCTCCGACGACCAGCTGGTGTCCATGTCGGTGCGCGAGCTGAAC

CGGCAGCTCCGCGGCTTCAGCAAGGAGGAGGTCATCCGGCTCAAGCAG

AAGCGGCGCACGCTCAAGAACCGCGGCTACGCGCAGTCCTGCCGCTTC

AAGCGGGTGCAGCAGCGGCACATTCTGGAGAGCGAGAAGTGCCAACTC

CAGAGCCAGGTGGAGCAGCTGAAGCTGGAGGTGGGGCGCCTGGCCAAA

GAGCGGGACCTGTACAAGGAGAAATACGAGAAGCTGGCGGGCCGGGGC

GGCCCCGGGAGCGCGGGCGGGGCCGGTTTCCCGCGGGAGCCTTCGCCG

CCGCAGGCCGGTCCCGGCGGGGCCAAGGGCACGGCCGACTTCTTCCTG

TAG
```

Neurog3, also known as neurogenin 3 or Ngn3, is a basic helix-loop-helix (bHLH) transcription factor required for endocrine development in the pancreas and intestine. Suitable sources of nucleic acids encoding Neurog3 include for example the human Neurog3 nucleic acid (and the encoded protein sequences) available as GenBank Accession Nos. NM_020999.3 and NP_066279.2, respectively.

NeuroD1, also known as Neuro Differentiation 1 or NeuroD, and beta-2 (β2) is a Neuro D-type transcription factor. It is a basic helix-loop-helix transcription factor that forms heterodimers with other bHLH proteins and activates transcription of genes that contain a specific DNA sequence known as the E-box. It regulates expression of the insulin gene, and mutations in this gene result in type II diabetes mellitus. Suitable sources of nucleic acids encoding NeuroD1 include for example the human NeuroD1 nucleic acid (and the encoded protein sequences) available as GenBank Accession Nos. NM_002500.4 and NP_002491.2, respectively.

In one embodiment, the amino acid sequence of a NeuroD1 polypeptide is set forth in SEQ ID NO: 6:

```
                                       (SEQ ID NO: 6)
MTKSYSESGLMGEPQPQGPPSWTDECLSSQDEEHEADKKEDDLETMNA

EEDSLRNGGEEEDEDEDLEEEEEEEEEDDDQKPKRRGPKKKKMTKARL

ERFKLRRMKANARERNRMHGLNAALDNLRKVVPCYSKTQKLSKIETLR

LAKNYIWALSEILRSGKSPDLVSFVQTLCKGLSQPTTNLVAGCLQLNP

RTFLPEQNQDMPPHLPTASASFPVHPYSYQSPGLPSPPYGTMDSSHVF
```

-continued

HVKPPPHAYSAALEPFFESPLTDCTSPSFDGPLSPPLSINGNFSFKHE

PSAEFEKNYAFTMHYPAATLAGAQSHGSIFSGTAAPRCEIPIDNIMSF

DSHSHHERVMSAQLNAIFHD.

In another embodiment, the nucleic acid sequence of a NeuroD1 polynucleotide is set forth in SEQ ID NO: 7.

(SEQ ID NO: 7)
ATGACCAAATCGTACAGCGAGAGTGGGCTGATGGGCGAGCCTCAGCCC

CAAGGTCCTCCAAGCTGGACAGACGAGTGTCTCAGTTCTCAGGACGAG

GAGCACGAGGCAGACAAGAAGGAGGACGACCTCGAAGCCATGAACGCA

GAGGAGGACTCACTGAGGAACGGGGGAGAGGAGGAGGACGAAGATGAG

GACCTGGAAGAGGAGGAAGAAGAGGAAGAGGAGGATGACGATCAAAAG

CCCAAGAGACGCGGCCCCAAAAAGAAGAAGATGACTAAGGCTCGCCTG

GAGCGTTTTAAATTGAGACGCATGAAGGCTAACGCCCGGGAGCGGAAC

CGCATGCACGGACTGAACGCGGCGCTAGACAACCTGCGCAAGGTGGTG

CCTTGCTATTCTAAGACGCAGAAGCTGTCCAAAATCGAGACTCTGCGC

TTGGCCAAGAACTACATCTGGGCTCTGTCGGAGATCTCGCGCTCAGGC

AAAAGCCCAGACCTGGTCTCCTTCGTTCAGACGCTTTGCAAGGGCTTA

TCCCAACCCACCACCAACCTGGTTGCGGGCTGCCTGCAACTCAATCCT

CGGACTTTTCTGCCTGAGCAGAACCAGGACATGCCCCCGCACCTGCCG

ACGGCCAGCGCTTCCTTCCCTGTACACCCCTACTCCTACCAGTCGCCT

GGGCTGCCCAGTCCGCCTTACGGTACCATGGACAGCTCCCATGTCTTC

CACGTTAAGCCTCCGCCGCACGCCTACAGCGCAGCGCTGGAGCCCTTC

TTTGAAAGCCCTCTGACTGATTGCACCAGCCCTTCCTTTGATGGACCC

CTCAGCCCGCCGCTCAGCATCAATGGCAACTTCTCTTTCAAACACGAA

CCGTCCGCCGAGTTTGAGAAAAATTATGCCTTTACCATGCACTATCCT

GCAGCGACACTGGCAGGGGCCCAAAGCCACGGATCAATCTTCTCAGGC

ACCGCTGCCCCTCGCTGCGAGATCCCCATAGACAATATTATGTCCTTC

GATAGCCATTCACATCATGAGCGAGTCATGAGTGCCCAGCTCAATGCC

ATATTTCATGATTAG.

Sox9 is a transcription factor that is involved in embryonic development. Sox9 has been particularly investigated for its importance in bone and skeletal development. SOX-9 recognizes the sequence CCTTGAG along with other members of the HMG-box class DNA-binding proteins. In the context of the disclosure presented herein, the use of Sox9 may be involved in maintaining the pancreatic progenitor cell mass, either before or after induction of transdifferentiation. Suitable sources of nucleic acids encoding Sox9 include for example the human Sox9 nucleic acid (and the encoded protein sequences) available as GenBank Accession Nos. NM_000346.3 and NP_000337.1, respectively.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 4-9 of greater than 60%. In another embodiment, "homology" refers to identity to a sequence selected from SEQ ID No: 1-76 of greater than 70%. In another embodiment, the identity is greater than 75%, greater than 78%, greater than 80%, greater than 82%, greater than 83%, greater than 85%, greater than 87%, greater than 88%, greater than 90%, greater than 92%, greater than 93%, greater than 95%, greater than 96%, greater than 97%, greater than 98%, or greater than 99%. In another embodiment, the identity is 100%. Each possibility represents a separate embodiment of the disclosure presented herein.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example Each method of determining homology represents a separate embodiment of the disclosure presented herein.

The cell can be any cell that is capable of producing pancreatic hormones, e.g., bone marrow muscle, spleen, kidney, blood, skin, pancreas, or liver. In one embodiment, the cell is a non-pancreatic cell. In another embodiment, the cell is a non-pancreatic β-cell. In one embodiment, the cells are capable of functioning as a pancreatic islet, i.e., store, process and secrete pancreatic hormones. In another embodiment, secretion is glucose regulated.

In another embodiment, glucose regulated insulin secretion comprises at least 0.001 pg insulin/$10^6$ cells/hour in response to high glucose concentrations. In another embodiment, glucose regulated insulin secretion comprises at least 0.002 pg insulin/$10^6$ cells/hour in response to high glucose concentrations. In another embodiment, glucose regulated insulin secretion comprises at least 0.003 pg insulin/$10^6$ cells/hour in response to high glucose concentrations. In another embodiment, glucose regulated insulin secretion comprises at least 0.005 pg insulin/$10^6$ cells/hour in response to high glucose concentrations. In another embodiment, glucose regulated insulin secretion comprises at least 0.007 pg insulin/$10^6$ cells/hour in response to high glucose concentrations. In another embodiment, glucose regulated insulin secretion comprises at least 0.01 pg insulin/$10^6$ cells/hour in response to high glucose concentrations. In another embodiment, glucose regulated insulin secretion comprises at least 0.5 pg insulin/$10^6$ cells/hour in response to high glucose concentrations. In another embodiment, glucose regulated insulin secretion comprises at least 1 pg insulin/$10^6$ cells/hour in response to high glucose concentrations. In another embodiment, glucose regulated insulin secretion comprises at least 5 pg insulin/$10^6$ cells/hour in response to high glucose concentrations. In another embodiment, glucose regulated insulin secretion comprises at least 10 pg insulin/$10^6$ cells/hour in response to high glucose concentrations. In another embodiment, glucose regulated insulin secretion comprises at least 50 pg insulin/$10^6$ cells/hour in response to high glucose concentrations. In another embodiment, glucose regulated insulin secretion comprises at least 100 pg insulin/$10^6$ cells/hour in response to high glucose concentrations. In another embodiment, glucose regulated insulin secretion comprises at least 500 pg insulin/$10^6$ cells/hour in response to high glucose concentrations. In another embodiment, glucose regulated insulin secretion comprises at least 1 ng insulin/$10^6$ cells/hour in response to high glucose concentrations. In another embodiment, glucose regulated insulin secretion comprises at least 5 ng insulin/$10^6$ cells/hour in response to high glucose concentrations. In another embodiment, glucose regulated insulin secretion comprises at least 10 ng insulin/$10^6$ cells/hour in response to high glucose concentrations. In another embodiment, glucose regulated insulin secretion comprises at least 50 ng insulin/$10^6$ cells/hour in response to high glucose concentrations. In another embodiment, glucose regulated insulin secretion comprises at least 100 ng insulin/$10^6$ cells/hour in response to high glucose concentrations. In another embodiment, glucose regulated insulin secretion comprises at least 500 ng insulin/$10^6$ cells/hour in response to high glucose concentrations. In another embodiment, glucose regulated insulin secretion comprises at least 1 µg insulin/$10^6$ cells/hour in response to high glucose concentrations. In another embodiment, glucose regulated insulin secretion comprises at least 5 µg insulin/$10^6$ cells/hour in response to high glucose concentrations. In another embodiment, glucose regulated insulin secretion comprises at least 10 µg insulin/$10^6$ cells/hour in response to high glucose concentrations. In another embodiment, glucose regulated insulin secretion comprises at least 50 µg insulin/$10^6$ cells/hour in response to high glucose concentrations. In another embodiment, glucose regulated insulin secretion comprises at least 100 µg insulin/$10^6$ cells/hour in response to high glucose concentrations.

In another embodiment, the pancreatic hormone comprises insulin, which may be secreted upon an extracellular trigger. In another embodiment, the cell is a liver cell. In additional embodiments, the cell is totipotent or pluripotent. In alternative embodiments the cell is a hematopoietic stem cell, embryonic stem cell or preferably a hepatic stem cell. In other embodiments, the cell is an induced pluripotent stem cells.

In one embodiment, the source of a cell population disclosed here in is a human source. In another embodiment, the source of a cell population disclosed here in is an autologous human source relative to a subject in need of insulin therapy. In another embodiment, the source of a cell population disclosed here in is an allogeneic human source relative to a subject in need of insulin therapy.

In certain embodiments, the cell is a mesenchymal stem cell, also known as a mesenchymal stromal cell, (MSC) such as a MSC derived from, liver tissue, adipose tissue, bone marrow, skin, placenta, umbilical cord, Wharton's jelly or cord blood. By "umbilical cord blood" or "cord blood" is meant to refer to blood obtained from a neonate or fetus, most preferably a neonate and preferably refers to blood which is obtained from the umbilical cord or the placenta of newborns. These cells can be obtained according to any conventional method known in the art. MSC are defined by expression of certain cell surface markers including, but not limited to, CD105, CD73 and CD90 and ability to differentiate into multiple lineages including osteoblasts, adipocytes and chondroblasts. MSC can be obtained from tissues by conventional isolation techniques such as plastic adherence, separation using monoclonal antibodies such as STRO-1 or through epithelial cells undergoing an epithelial-mesenchymal transition (EMT).

A skilled artisan would appreciate that the term "adipose tissue-derived mesenchymal stem cells" may encompass undifferentiated adult stem cells isolated from adipose tissue and may also be term "adipose stem cells", having all the same qualities and meanings. These cells can be obtained according to any conventional method known in the art.

A skilled artisan would appreciate that the term, "placental-derived mesenchymal stem cells" may encompass undifferentiated adult stem cells isolated from placenta and may be referred to herein as "placental stem cells", having all the same meanings and qualities.

The cell population that is exposed to, i.e., contacted with, the compounds (i.e. PDX-1, Pax-4, MafA, NeuroD1 and/or Sox-9 polypeptides or nucleic acid encoding PDX-1, Pax-4, MafA, NeuroD1 and/or Sox-9 polypeptides) can be any number of cells, i.e., one or more cells, and can be provided in vitro, in vivo, or ex vivo. The cell population that is contacted with the transcription factors can be expanded in vitro prior to being contacted with the transcription factors. The cell population produced exhibits a mature pancreatic beta cell phenotype. These cells can be expanded in vitro by methods known in the art prior to transdifferentiation and maturation along the β-cell lineage, and prior to administration or delivery to a patient or subject in need thereof.

The subject is, in one embodiment, a mammal. The mammal can be, e.g., a human, non-human primate, mouse, rat, dog, cat, horse, or cow.

In some embodiments, the transcription factor is a polypeptide, such as PDX-1, Pax-4, MafA, NeuroD1 or Sox-9, or combination thereof and is delivered to a cell by methods known in the art. For example, the transcription factor polypeptide is provided directly to the cells or delivered via a microparticle or nanoparticle, e.g., a liposomal carrier.

In some embodiments, the transcription factor is a nucleic acid. For example, the nucleic acid encodes a PDX-1, Pax-4, MafA, NeuroD1 or Sox-9 polypeptide. The nucleic acid encoding the transcription factor, or a combination of such nucleic acids, can be delivered to a cell by any means known in the art. In some embodiments, the nucleic acid is incorporated in an expression vector or a viral vector. In one embodiment, the viral vector is an adenovirus vector. In another embodiment, an adenoviral vector is a first generation adenoviral (FGAD) vector. In another embodiment, an FGAD is unable in integrate into the genome of a cell. In another embodiment, a FGAD comprises an E1-deleted recombinant adenoviral vector. In another embodiment, a FGAD provide transient expression of encoded polypeptides.

The expression or viral vector can be introduced to the cell by any of the following: transfection, electroporation, infection, or transduction. In other embodiments the nucleic acid is mRNA and it is delivered for example by electroporation. In one embodiment, methods of electroporation comprise flow electroporation technology. For example, in another embodiment, methods of electroporation comprise use of a MaxCyte electroporation system (MaxCyte Inc. Georgia USA).

In certain embodiments, the manufactured population of human insulin producing cells comprises a reduction of liver phenotypic markers. In one embodiment, there is a reduction of expression of albumin, alpha-1 anti-trypsin, or a combination thereof. In another embodiment, less than 5% of the cell population expressing endogenous PDX-1 expresses albumin and alpha-1 anti-trypsin. In another embodiment, less than 10%, 9%, 8%, 7%, 6%, 4%, 3%, 2%, or 1% of the cell population expressing endogenous PDX-1 expresses albumin and alpha-1 anti-trypsin.

Cell Populations Predisposed for Transdifferentiation

The disclosure presented herein provides liver derived cell populations that are predisposed for transdifferentiation. The cell populations may be useful in the methods of producing pancreatic beta cells described herein. Cells that are predisposed for transdifferentiation of the disclosure presented herein may also be referred to as having increased or enriched transdifferentiation capacity. By "increased transdifferentiation capacity" is meant that when the cell population of the disclosure presented herein is subjected to a differentiation protocol (i.e. introduction of a pancreatic transcription factor), greater than 15%, greater than 20%, greater than 30%, greater than 40%, greater than 50%, greater than 60%, greater than 70% or greater than 80% of the cells may differentiate to an alternate cell type. In one embodiment, a population of endothelial cells, epithelial cells, mesenchymal cells, fibroblasts, or liver cells with increased transdifferentiation capacity may be differentiated to mature pancreatic cells or mature neural cells (transdifferentiation).

In another embodiment, cell populations that are predisposed for transdifferentiation have the capability of activating the glutamine synthetase response element (GSRE). For example, in the cell populations of the disclosure presented herein, at least 2%, at least 3%, at least 4%, at least 5%, at least 10%, at least 15%, at least 20%, at least 30%, at least 40%, at least 50%, at least 60%, at least 70%, at least 80% or at least 90% of the cells in the population are capable of activating GSRE. In one embodiment, at least 30% of the cells in the population are capable of activating GSRE. Glutamine synthetase is an enzyme predominantly expressed in the brain, kidneys and liver, and plays an essential role in the metabolism of nitrogen by catalyzing the condensation of glutamate and ammonia to form glutamine Glutamine synthetase is, for example, uniquely expressed in pericentral liver cells and astrocytes in the brain. Data presented herein indicate that cells that demonstrate activation of GSRE provide a unique selective parameter for the isolation of cells predisposed for transdifferentiation. In another embodiment, a predisposed population of cells comprises pericentral liver cells.

Activation of GSRE can be measured by methods known to one of ordinary skill in the art. For example, a recombinant adenovirus can be generated containing the glutamine synthetase response element operatively linked to a promoter and a reporter gene, such as a fluorescent protein. This recombinant adenovirus with the GSRE-reporter can be introduced into a heterogeneous mixture of cells containing some proportion of cells that are predisposed for transdifferentiation. Those cells that are competent for activation of the GSRE will express the reporter gene, which can be detected by methods known in the art, thereby identifying cells predisposed for transdifferentiation.

Figure 17:
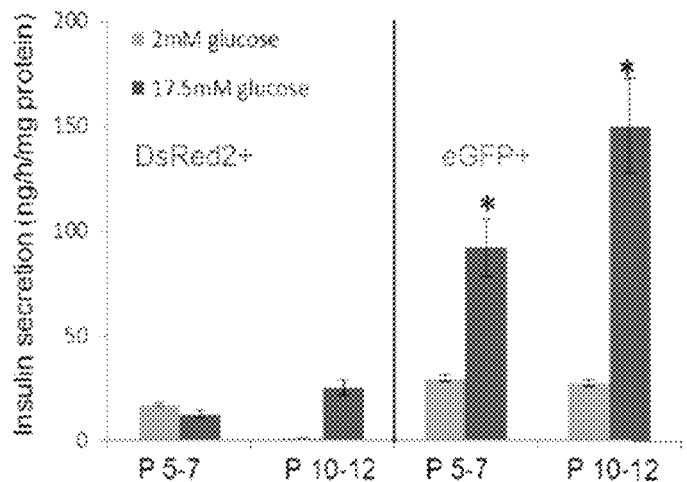
FIG. 17 shows higher transdifferentiation efficiency in eGFP+ population is stable with increasing passages in culture. The two groups proliferated separately after sorting and were similarly treated with pTFs (Ad-Pdx-1+Ad-Pax-4+Ad-MafA and soluble factors) after a few passages (5-7 passages post sorting) or a higher number of passages (10-12 passages post sorting). Regulated insulin secretion was analyzed by static incubations at low followed by high glucose concentrations (2 mM and 17.5 mM glucose in KRB, respectively). Insulin secretion is measured using the human insulin radioimmunoassay kit (DPC; n≥6 from 2 different experiments). No statistical significant differences were detected between the low and high number of passages in both populations of cells, suggesting a persistent tendency of eGFP tagged cells to undergo pTFs induced transdifferentiation along the β-cell lineage and function.

A heterogeneous population of cells, in which those cells predisposed for transdifferentiation are unknown, can be contacted with an adenoviral vector that contains the GSRE operatively linked to a minimal TK promoter and eGFP. The cells that activate the GSRE will express GFP and can be identified by various methods known in the art to detect GFP expression. For example, separation of the GSRE-activated cells which are predisposed for transdifferentiation from the cells that are not predisposed for transdifferentiation can be achieved through FACs apparatus, sorter and techniques known to those ordinarily skilled in the art (FIG. 14). The separated cells that are predisposed for transdifferentiation can then be propagated or expanded in vitro. Results described herein demonstrate that passaging of the cells predisposed for transdifferentiation for 5-12 passages or more retain their transdifferentiation capacity. For example, isolated liver cells predisposed for transdifferentiation continue to produce and secrete insulin in a glucose-dependent manner even after 12 passages in culture (FIG. 17).

In another embodiment, cell populations that are predisposed for transdifferentiation also have active Wnt signaling pathways. Wnt signaling pathways play a significant role in stem cell pluripotency and cell fate during development, as well as body axis patterning, cell proliferation, and cell migration. Wnt signaling pathways are activated by the binding of a Wnt-protein ligand to a Frizzled (Fz) family receptor (a G-coupled protein receptor), optionally activating a co-receptor protein, and the subsequent activation of a cytoplasmic protein called Dishevelled (Dsh). In the canonical Wnt pathway, co-receptor LRP-5/6 is also activated and beta-catenin accumulates in the cytoplasm and is eventually translocated into the nucleus to act as a transcriptional coactivator of TCF/LEF transcription factors. Without Wnt signaling, a destruction complex that includes proteins such as adenomatosis polyposis *coli* (APC), Axin, protein phosphatase 2A (PP2A), glycogen synthase kinase 3 (GSK3) and casein kinase 1α (CK1α) targets β-catenin for ubiquitination and its subsequent degradation by the proteasome. However, activation of the Frizzled receptor by Wnt binding causes disruption of the destruction complex, thereby allowing β-catenin to accumulate.

Wnt signaling can also occur through noncanonical pathways that utilize different co-receptor proteins and activate different downstream effectors to, for example, regulate of the cytoskeleton, stimulate of calcium release from the endoplasmic reticulum, activate mTOR pathways, and regulate myogenesis.

One of ordinary skill in the art could readily use methods known in the art to determine the activation of Wnt signaling pathways. For example, cells that express Wnt3a, decreased levels of DKK1 or DKK3, decreased levels of APC, increased activated beta-catenin levels, or STAT3 binding elements have active Wnt signaling pathways. DKK1, DKK3, and APC are known inhibitors of Wnt signaling pathways. Other signaling effectors that indicate active Wnt signaling pathways are readily known in the art.

In one embodiment, methods disclosed further comprise treating the primary adult human liver cell population with lithium, wherein said treated population is enriched in cells predisposed to transdifferentiation. In another embodiment, methods disclosed further comprise treating the primary adult human liver cell population with lithium, wherein said cells predisposed to transdifferentiation within the population have an increased predisposition following treatment with lithium. Thus, an enriched population of cells predisposed to transdifferentiation may be established by treating a primary adult population of cells with lithium.

In one embodiment, a primary adult population of cells is treated with 10 mM of lithium. In another embodiment, a primary adult population of cells is treated with 1 mM of lithium. In one embodiment, a primary adult population of cells is treated with between 1-10 mM of lithium. In one embodiment, a primary adult population of cells is treated with 2 mM of lithium. In one embodiment, a primary adult population of cells is treated with 3 mM of lithium. In one embodiment, a primary adult population of cells is treated with 4 mM of lithium. In one embodiment, a primary adult population of cells is treated with 5 mM of lithium. In one embodiment, a primary adult population of cells is treated with 6 mM of lithium. In one embodiment, a primary adult population of cells is treated with 7 mM of lithium. In one embodiment, a primary adult population of cells is treated with 8 mM of lithium. In one embodiment, a primary adult population of cells is treated with 9 mM of lithium. In one embodiment, a primary adult population of cells is treated with about 10-20 mM of lithium. In one embodiment, a primary adult population of cells is treated with 15 mM of lithium. In one embodiment, a primary adult population of cells is treated with 20 mM of lithium. In one embodiment, a primary adult population of cells is treated with 10-50 mM of lithium. In one embodiment, a primary adult population of cells is treated with 10-100 mM of lithium.

In another embodiment, cells were treated prior to the time of transdifferentiation (the first time period). In another embodiment, cells were treated 12 hours prior to transdifferentiation (the first time period). In another embodiment, cells were treated 24 hours prior to transdifferentiation (the first time period). In another embodiment, cells were treated 36 hours prior to transdifferentiation (the first time period). In another embodiment, cells were treated 48 hours prior to transdifferentiation (the first time period). In another embodiment, cells were treated 60 hours prior to transdifferentiation (the first time period). In another embodiment, cells were treated 72 hours prior to transdifferentiation (the first time period). In yet another embodiment, cells were treated at the time of transdifferentiation (the first time period).

In one embodiment, the cell populations used in methods disclosed herein are predisposed for transdifferentiation to the pancreatic lineage, wherein the transdifferentiated cells exhibit pancreatic phenotype and function. For example, the transdifferentiated cells exhibit mature pancreatic beta cell phenotype and function, which includes, but is not limited to, expression, production, and/or secretion of pancreatic hormones. Pancreatic hormones can include, but are not limited to, insulin, somatostatin, glucagon, or islet amyloid polypeptide (IAPP). Insulin can be hepatic insulin or serum insulin. In one embodiment, the insulin is a fully process form of insulin capable of promoting glucose utilization, and carbohydrate, fat and protein metabolism. For example, the cells predisposed for transdifferentiation may encompass about 15% of all the cells in a heterogeneous in vitro primary human liver cell culture. When the cells ectopically express pTFs, greater than 5%, 10%, 15%, 20%, 25%, 30%, 40%, 50% of the cells in culture produce insulin or secrete C-peptide.

Figure 10A:
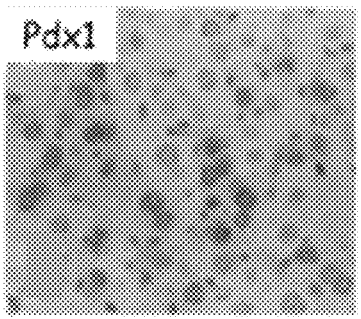
FIGS. 10A-10D shows PDX-1-induced insulin producing cells' (IPCs) activation in mice in vivo is restricted to cells adjacent to the central veins that are characterized by glutamine synthetase (GS) expression Immunohistochemical analysis of Pdx-1 (FIG. 10A) and insulin (FIG. 10B) 14 days after Ad-CMV-PDX-1 administration. Arrows indicate positive cells, mostly located at the proximity of central veins (cv).
Figure 10B:
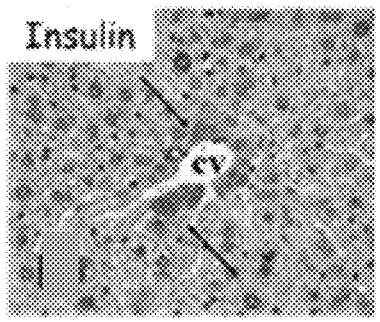
Figure 10C:
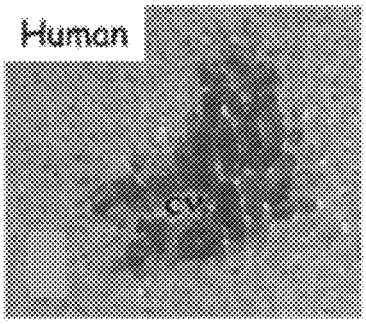
Figure 10D:
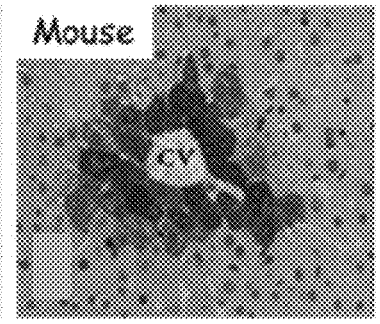

In one embodiment, cell populations that are predisposed for transdifferentiation are located in close proximity to the central veins of the liver, or are pericentral liver cells. As shown herein, although over 40-50% of liver cells that ectopically express pancreatic transcription factors, such as PDX-1, only a subset of cells produced insulin upon pTF expression. These insulin-producing cells (IPCs) were primarily located close to the central veins, as shown by FIG. 10B. These cells are also characterized by expression of glutamine synthetase and active Wnt signaling.

In another embodiment, the cell populations used in methods disclosed herein is predisposed for transdifferentiation to the neural lineage, wherein the transdifferentiated cells express neural markers, exhibit neural phenotype, or exhibit neural function. The transdifferentiated cells can be neurons or glial cells.

In another embodiment, cells with increased predisposition for transdifferentiation may be identified through specific cell surface markers. For example, cells with increased levels of HOMER1, LAMP5 or BMPR2 indicate cells with increased transdifferentiation capacity when compared to cells without predisposition for transdifferentiation. Cells with decreased levels of ABCB1, ITGA4, ABCB4, or PRNP indicate cells with increased transdifferentiation capacity when compared to cells without predisposition for transdifferentiation. Any combination of the cell surface markers described can be used to distinguish a cell population predisposed to transdifferentiation from a cell population that is not predisposed to transdifferentiation. Antibodies to these cell surface markers are commercially available. Immunoassay or immunoaffinity techniques known in the art may be utilized to distinguish cells with increased transdifferentiation capacity from those cells without transdifferentiation capacity.

Use of the cell populations of the disclosure presented herein to produce cells that exhibit pancreatic cell phenotypes provide certain advantages over differentiating heterogeneous populations of non-pancreatic cells to produce cells that exhibit pancreatic cell phenotypes. Previous studies that describe expressing a pancreatic transcription factor (pTF) such as PDX-1 in a heterogeneous population of non-pancreatic cells (i.e., liver cells) show that at best, only 15% of the PDX-1-expressing cells are competent for producing insulin. Therefore, only 15% of the cells were successfully differentiated to a mature pancreatic beta cell capable of producing and secreting pancreatic hormones. In contrast, introducing pTFs into the cell populations of the disclosure presented herein results in at least 30%, at least 40%, at least 50%, at least 60%, at least 70%, or at least 80% of the cells are differentiated to a mature pancreatic beta cell phenotype, for example, produce insulin, glucagon, and/or secrete c-peptide. In one embodiment, when the cells of the cell population of the disclosure presented herein express a pancreatic transcription factor, at least 30% of the cells produce insulin or secrete C-peptide.

Methods of Transdifferentiation

The disclosure presented herein also provides methods for utilizing the cell populations with increased transdifferentiation capacity to produce cells that exhibit a mature differentiated cell type, where the differentiated cell has a different phenotype from the starting cell population. For example, a population of cells with increased transdifferentiation capacity (i.e. epithelial cells, fibroblasts or liver cells) can be differentiated to cells along the pancreatic or neural lineage to exhibit mature differentiated pancreatic or neural cell phenotypes. Any means known in the art for differentiating cells to pancreatic or neural lineage can be utilized.

In one embodiment, the cell population predisposed for transdifferentiation may be differentiated along the neural lineage through the expression of neural transcription factors. Suitable neural transcription factors are known in the art. In other embodiments, the cell population of the disclosure presented herein may be differentiated to mature neural cells through contacting the cells with various cytokines, growth factors, or other agents known in the art to differentiate cells to the neural lineage. The differentiated neural cells may express neural markers, exhibit a neural phenotype (i.e., neural gene expression profile), or exhibit neural function. The differentiated cells can be neurons or glial cells.

In another embodiment, the cell population predisposed for transdifferentiation may be differentiated along the pancreatic lineage through the expression of pancreatic transcription factors. The pancreatic transcription factors are, for example, PDX-1, Pax-4, MafA, NeuroD1, or a combination thereof. Methods for producing pancreatic beta cells are described in U.S. Pat. No. 6,774,120 and U.S. Publication No. 2005/0090465, the contents of which are incorporated by reference in their entireties.

In another embodiment, the cell population predisposed for transdifferentiation may be differentiated along the pancreatic lineage through the methods described herein.

Pancreatic Beta-Cell Phenotypes

The methods provided herein produce cells with a mature pancreatic beta cell phenotype or function. A skilled artisan would appreciate that the term "pancreatic beta cell phenotype or function" may encompass cells that display one or more characteristics typical of pancreatic beta cells, i.e. pancreatic hormone production, processing, storage in secretory granules, hormone secretion, activation of pancreatic gene promoters, or characteristic beta cell gene expression profile. Hormone secretion includes nutritionally and/or hormonally regulated secretion. In one embodiment, the cells produced exhibit at least one pancreatic beta cell phenotype or function, as described herein.

The pancreatic hormone can be for example, insulin, glucagon, somatostatin or islet amyloid polypeptide (IAPP). Insulin can be hepatic insulin or serum insulin. In another embodiment the pancreatic hormone is hepatic insulin. In an alternative embodiment the pancreatic hormone is serum insulin (i.e., a fully processed form of insulin capable of promoting, e.g., glucose utilization, carbohydrate, fat and protein metabolism).

In some embodiments the pancreatic hormone is in the "prohormone" form. In other embodiments the pancreatic hormone is in the fully processed biologically active form of the hormone. In other embodiments the pancreatic hormone is under regulatory control i.e., secretion of the hormone is under nutritional and hormonal control similar to endogenously produced pancreatic hormones. For example, in one embodiment disclosed herein, the hormone is under the regulatory control of glucose.

The pancreatic beta cell phenotype can be determined for example by measuring pancreatic hormone production, i.e., insulin, somatostatin or glucagon protein mRNA or protein expression. Hormone production can be determined by methods known in the art, i.e. immunoassay, Western blot, receptor binding assays or functionally by the ability to ameliorate hyperglycemia upon implantation in a diabetic host. Insulin secretion can also be measured by, for example, C-peptide processing and secretion. In another embodiment, high-sensitivity assays may be utilized to measure insulin secretion. In another embodiment, high-sensitivity assays comprise an enzyme-linked immunosorbent assay (ELISA), a mesoscale discovery assay (MSD), or an Enzyme-Linked ImmunoSpot assay (ELISpot), or an assay known in the art.

In some embodiments, the cells may be directed to produce and secrete insulin using the methods specified herein. The ability of a cell to produce insulin can be assayed by a variety of methods known to those of ordinary skill in the art. For example, insulin mRNA can be detected by RT-PCR or insulin may be detected by antibodies raised against insulin. In addition, other indicators of pancreatic differentiation include the expression of the genes Isl-1, Pdx-1, Pax-4, Pax-6, and Glut-2. Other phenotypic markers for the identification of islet cells are disclosed in U.S. 2003/0138948, incorporated herein in its entirety.

The pancreatic beta cell phenotype can be determined for example by promoter activation of pancreas-specific genes. Pancreas-specific promoters of particular interest include the promoters for insulin and pancreatic transcription factors, i.e. endogenous PDX-1. Promoter activation can be determined by methods known in the art, for example by luciferase assay, EMSA, or detection of downstream gene expression.

In some embodiments, the pancreatic beta-cell phenotype can also be determined by induction of a pancreatic gene expression profile. A skilled artisan would appreciate that the term "pancreatic gene expression profile" may encompass a profile to include expression of one or more genes that are normally transcriptionally silent in non-endocrine tissues, i.e., a pancreatic transcription factor, pancreatic enzymes or pancreatic hormones. Pancreatic enzymes are, for example, PCSK2 (PC2 or prohormone convertase), PC1/3 (prohormone convertase 1/3), glucokinase, glucose transporter 2 (GLUT-2). Pancreatic-specific transcription factors include, for example, Nkx2.2, Nkx6.1, Pax-4, Pax-6, MafA, NeuroD1, NeuroG3, Ngn3, beta-2, ARX, BRAIN4 and Isl-1.

Induction of the pancreatic gene expression profile can be detected using techniques well known to one of ordinary skill in the art. For example, pancreatic hormone RNA sequences can be detected in, e.g., Northern blot hybridization analyses, amplification-based detection methods such as reverse-transcription based polymerase chain reaction or systemic detection by microarray chip analysis. Alternatively, expression can be also measured at the protein level, i.e., by measuring the levels of polypeptides encoded by the gene. In a specific embodiment PC1/3 gene or protein expression can be determined by its activity in processing prohormones to their active mature form. Such methods are well known in the art and include, e.g., immunoassays based on antibodies to proteins encoded by the genes, or HPLC of the processed prohormones.

In some embodiments, the cells exhibiting a mature beta-cell phenotype generated by the methods described herein may repress at least one gene or the gene expression profile of the original cell. For example, a liver cell that is induced to exhibit a mature beta-cell phenotype may repress at least one liver-specific gene. One skilled in the art could readily determine the liver-specific gene expression of the original cell and the produced cells using methods known in the art, i.e. measuring the levels of mRNA or polypeptides encoded by the genes. Upon comparison, a decrease in the liver-specific gene expression would indicate that transdifferentiation has occurred.

In certain embodiments, the transdifferentiated cells disclosed herein comprise a reduction of liver phenotypic markers. In one embodiment, there is a reduction of expression of albumin, alpha-1 anti-trypsin, or a combination thereof. In another embodiment, less than 5% of the cell population expressing endogenous PDX-1 expresses albumin and alpha-1 anti-trypsin. In another embodiment, less than 10%, 9%, 8%, 7%, 6%, 4%, 3%, 2%, or 1% of the transdifferentiated cells expressing endogenous PDX-1 expresses albumin and alpha-1 anti-trypsin.

Methods of Treating a Pancreatic Disorder

The disclosure presented herein discloses methods for use in treating, i.e., preventing or delaying the onset or alleviating a symptom of a pancreatic disorder in a subject. For example, the pancreatic disorder is a degenerative pancreatic disorder. The methods disclosed herein are particularly useful for those pancreatic disorders that are caused by or result in a loss of pancreatic cells, e.g., islet beta cells, or a loss in pancreatic cell function.

Common degenerative pancreatic disorders include, but are not limited to: diabetes (e.g., type I, type II, or gestational) and pancreatic cancer. Other pancreatic disorders or pancreas-related disorders that may be treated by using the methods disclosed herein are, for example, hyperglycemia, pancreatitis, pancreatic pseudocysts or pancreatic trauma caused by injury. Additionally, individuals whom have had a pancreatectomy are also suitable to treatment by the disclosed methods.

Diabetes is a metabolic disorder found in three forms: type 1, type 2 and gestational. Type 1, or IDDM, is an autoimmune disease; the immune system destroys the pancreas' insulin-producing beta cells, reducing or eliminating the pancreas' ability to produce insulin. Type 1 diabetes patients must take daily insulin supplements to sustain life. Symptoms typically develop quickly and include increased thirst and urination, chronic hunger, weight loss, blurred vision and fatigue. Type 2 diabetes is the most common, found in 90 percent to 95 percent of diabetes sufferers. It is associated with older age, obesity, family history, previous gestational diabetes, physical inactivity and ethnicity. Gestational diabetes occurs only in pregnancy. Women who develop gestational diabetes have a 20 percent to 50 percent chance of developing type 2 diabetes within five to 10 years.

A subject suffering from or at risk of developing diabetes is identified by methods known in the art such as determining blood glucose levels. For example, a blood glucose value above 140 mg/dL on at least two occasions after an overnight fast means a person has diabetes. A person not suffering from or at risk of developing diabetes is characterized as having fasting sugar levels between 70-110 mg/dL.

Symptoms of diabetes include fatigue, nausea, frequent urination, excessive thirst, weight loss, blurred vision, frequent infections and slow healing of wounds or sores, blood pressure consistently at or above 140/90, HDL cholesterol less than 35 mg/dL or triglycerides greater than 250 mg/dL, hyperglycemia, hypoglycemia, insulin deficiency or resistance. Diabetic or pre-diabetic patients to which the compounds are administered are identified using diagnostic methods know in the art.

Hyperglycemia is a pancreas-related disorder in which an excessive amount of glucose circulates in the blood plasma. This is generally a glucose level higher than (200 mg/dl). A subject with hyperglycemia may or may not have diabetes.

Pancreatic cancer is the fourth most common cancer in the U.S., mainly occurs in people over the age of 60, and has the lowest five-year survival rate of any cancer. Adenocarcinoma, the most common type of pancreatic cancer, occurs in the lining of the pancreatic duct; cystadenocarcinoma and acinar cell carcinoma are rarer. However, benign tumors also grow within the pancreas; these include insulinoma—a tumor that secretes insulin, gastrinoma—which secretes higher-than-normal levels of gastrin, and glucagonoma—a tumor that secretes glucagon.

Pancreatic cancer has no known causes, but several risks, including diabetes, cigarette smoking and chronic pancreatitis. Symptoms may include upper abdominal pain, poor appetite, jaundice, weight loss, indigestion, nausea or vomiting, diarrhea, fatigue, itching or enlarged abdominal organs. Diagnosis is made using ultrasound, computed tomography scan, magnetic resonance imaging, ERCP, percutaneous transhepatic cholangiography, pancreas biopsy or blood tests. Treatment may involve surgery, radiation therapy or chemotherapy, medication for pain or itching, oral enzymes preparations or insulin treatment.

Pancreatitis is the inflammation and autodigestion of the pancreas. In autodigestion, the pancreas is destroyed by its own enzymes, which cause inflammation. Acute pancreatitis typically involves only a single incidence, after which the pancreas will return to normal. Chronic pancreatitis, however, involves permanent damage to the pancreas and pancreatic function and can lead to fibrosis. Alternately, it may resolve after several attacks. Pancreatitis is most frequently caused by gallstones blocking the pancreatic duct or by alcohol abuse, which can cause the small pancreatic ductules to be blocked. Other causes include abdominal trauma or surgery, infections, kidney failure, lupus, cystic fibrosis, a tumor or a scorpion's venomous sting.

Symptoms frequently associated with pancreatitis include abdominal pain, possibly radiating to the back or chest, nausea or vomiting, rapid pulse, fever, upper abdominal swelling, ascites, lowered blood pressure or mild jaundice. Symptoms may be attributed to other maladies before being identified as associated with pancreatitis.

Method of Treating a Neurological Disorders

The disclosure presented herein also provides methods for treating a subject with a neurological disease or disorder. The population of cells described herein is useful for treating a subject with a neurological disease or disorder that is characterized by loss of neural cells or neural function, by way of replenishing the degenerated or nonfunctional cells. Neurodegenerative diseases that may be treated using the methods described herein include, but are not limited to, Parkinson's disease, Parkinsonian disorders, Alzheimer's disease, Huntington's disease, amyotrophic lateral sclerosis, Lewy body disease, age-related neurodegeneration, neurological cancers, and brain trauma resulting from surgery, accident, ischemia, or stroke. The population of cells described herein can be differentiated to a neural cell population with neural function, and the differentiated neural cell population may be administered to a subject with a neurological disease or disorder.

Recombinant Expression Vectors and Host Cells

Another embodiment disclosed herein, pertains to vectors. In one embodiment, a vector used in methods disclosed herein comprises an expression vector. In another embodiment, an expression vector comprises a nucleic acid encoding a PDX-1, Pax-4, NeuroD1 or MafA protein, or other pancreatic transcription factor, such as Ngn3, or derivatives, fragments, analogs, homologs or combinations thereof. In some embodiments, the expression vector comprises a single nucleic acid encoding any of the following transcription factors: PDX-1, Pax-4, NeuroD1, Ngn3, MafA, or Sox-9 or derivatives or fragments thereof. In some embodiments, the expression vector comprises two nucleic acids encoding any combination of the following transcription factors: PDX-1, Pax-4, NeuroD1, Ngn3, MafA, or Sox-9 or derivatives or fragments thereof. In a yet another embodiment, the expression vector comprises nucleic acids encoding PDX-1 and NeuroD1. In a still another embodiment, the expression vector comprises nucleic acids encoding PDX-1 and Pax4. In another embodiment, the expression vector comprises nucleic acids encoding MafA.

A skilled artisan would appreciate that the term "vector" encompasses a nucleic acid molecule capable of transporting another nucleic acid to which it has been linked. One type of vector is a "plasmid", which encompasses a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. A skilled artisan would appreciate that the terms "plasmid" and "vector" may be used interchangeably having all the same qualities and meanings. In one embodiment, the term "plasmid" is the most commonly used form of vector. However, the disclosure presented herein is intended to include such other forms of expression vectors, such as viral vectors (e.g., replication defective retroviruses, lentivirus, adenoviruses and adeno-associated viruses), which serve equivalent functions. Additionally, some viral vectors are capable of targeting a particular cells type either specifically or non-specifically.

The recombinant expression vectors disclosed herein comprise a nucleic acid disclosed herein, in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, a skilled artisan would appreciate that the term "operably linked" may encompass nucleotide sequences of interest linked to the regulatory sequence(s) in a manner that allows for expression of the nucleotide sequence (e.g., in an in vitro transcription/translation system or in a host cell when the vector is introduced into the host cell). A skilled artisan would appreciate that term "regulatory sequence" may encompass promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors disclosed here may be introduced into host cells to thereby produce proteins or peptides, including fusion proteins or peptides, encoded by nucleic acids as described herein (e.g., PDX-1, Pax-4, MafA, NeuroD1 or Sox-9 proteins, or mutant forms or fusion proteins thereof, etc.).

For example, an expression vector comprises one nucleic acid encoding a transcription factor operably linked to a promoter. In expression vectors comprising two nucleic acids encoding transcription factors, each nucleic acid may be operably linked to a promoter. The promoter operably linked to each nucleic acid may be different or the same. Alternatively, the two nucleic acids may be operably linked to a single promoter. Promoters useful for the expression vectors disclosed here could be any promoter known in the art. The ordinarily skilled artisan could readily determine suitable promoters for the host cell in which the nucleic acid is to be expressed, the level of expression of protein desired, or the timing of expression, etc. The promoter may be a constitutive promoter, an inducible promoter, or a cell-type specific promoter.

The recombinant expression vectors disclosed here can be designed for expression of PDX-1 in prokaryotic or eukaryotic cells. For example, PDX-1, Pax-4, MafA, NeuroD1, and/or Sox-9 can be expressed in bacterial cells such as *E. coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences disclosed here can be carried out by standard DNA synthesis techniques.

In another embodiment, the PDX-1, Pax-4, MafA, NeuroD1, or Sox-9 expression vector is a yeast expression vector. Examples of vectors for expression in yeast *S. cerevisiae* include pYepSec1 (Baldari, et al., (1987) EMBO J 6:229-234), pMFa (Kujan and Herskowitz, (1982) Cell 30:933-943), pJRY88 (Schultz et al., (1987) Gene 54:113-123), pYES2 (Invitrogen Corporation, San Diego, Calif.), and picZ (Invitrogen Corp, San Diego, Calif.).

Alternatively, PDX-1, Pax-4, MafA, NeuroD1 or Sox-9 can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156-2165) and the pVL series (Lucklow and Summers (1989) Virology 170:31-39).

In yet another embodiment, a nucleic acid disclosed here is expressed in mammalian cells using a mammalian expression vector. Examples of mammalian expression vectors include pCDM8 (Seed (1987) Nature 329:840) and pMT2PC (Kaufman et al. (1987) EMBO J 6: 187-195). When used in mammalian cells, the expression vectors control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268-277), lymphoid-specific promoters (Calame and Eaton (1988) Adv Immunol 43:235-275), in particular promoters of T cell receptors (Winoto and Baltimore (1989) EMBO J 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) PNAS 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally regulated promoters are also encompassed, e.g., the murine hox promoters (Kessel and Gruss (1990) Science 249:374-379) and the alpha-fetoprotein promoter (Campes and Tilghman (1989) Genes Dev 3:537-546).

The disclosure herein, further provides a recombinant expression vector comprising a DNA molecule disclosed here cloned into the expression vector in an antisense orientation. That is, the DNA molecule is operatively linked to a regulatory sequence in a manner that allows for expression (by transcription of the DNA molecule) of an RNA molecule that is antisense to PDX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another embodiment disclosed herein pertains to host cells into which a recombinant expression vector disclosed here has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX-1, Pax-4, MafA, NeuroD1 or Sox-9 or a combination thereof, and may either maintain or loose original characteristics.

A host cell can be any prokaryotic or eukaryotic cell. For example, PDX-1, Pax-4, MafA, NeuroD1 or Sox-9 protein can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA may be introduced into prokaryotic or eukaryotic cells via conventional transformation, transduction, infection or transfection techniques. A skilled artisan would appreciate that the terms "transformation" "transduction", "infection" and "transfection" may encompass a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition, transfection can be mediated by a transfection agent. A skilled artisan would appreciate that the term "transfection agent" may encompass any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. integration of the foreign DNA into the host genome) or "transient" (i.e., DNA is episomally expressed in the host cells or mRNA is electroporated into cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding PDX-1 or can be introduced on a separate vector. Cells stably transfected with the introduced nucleic acid can be identified by drug selection (e.g., cells that have incorporated the selectable marker gene will survive, while the other cells die). In another embodiment the cells modulated by PDX-1 or the transfected cells are identified by the induction of expression of an endogenous reporter gene. In a specific embodiment, the promoter is the insulin promoter driving the expression of green fluorescent protein (GFP).

In one embodiment the PDX-1, Pax-4, MafA, NeuroD1, or Sox-9 nucleic acid is present in a viral vector. In one embodiment, the PDX-1 and NeuroD1 nucleic acids are present in the same viral vector. In another embodiment, the PDX-1 and Pax4 nucleic acids are present in the same viral vector. In another embodiment the PDX-1, Pax-4, MafA, NeuroD1, or Sox-9 nucleic acid is encapsulated in a virus. In another embodiment, the PDX-1 and NeuroD1 is encapsulated in a virus (i.e., nucleic acids encoding PDX-1 and NeuroD1 are encapsulated in the same virus particle). In another embodiment, the PDX-1 and Pax4 are encapsulated in a virus (i.e., nucleic acids encoding PDX-1 and Pax4 are encapsulated in the same virus particle). In some embodiments the virus preferably infects pluripotent cells of various tissue types, e.g. hematopoietic stem, cells, neuronal stem cells, hepatic stem cells or embryonic stem cells, preferably the virus is hepatotropic. A skilled artisan would appreciate that the term "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

Gene Therapy

In one embodiment, a nucleic acid or nucleic acids encoding a PDX-1, Pax-4, MafA, NeuroD1, or Sox-9 polypeptide or a combination thereof, as disclosed herein, or functional derivatives thereof, are administered by way of gene therapy. Gene therapy refers to therapy that is performed by the administration of a specific nucleic acid to a subject. In one embodiment, the nucleic acid produces its encoded peptide(s), which then serve to exert a therapeutic effect by modulating function of an aforementioned disease or disorder. e.g., diabetes. Any of the methodologies relating to gene therapy available within the art may be used in the practice of the disclosure presented herein. See e.g., Goldspiel, et al., 1993. Clin Pharm 12: 488-505.

In another embodiment, the therapeutic comprises a nucleic acid that is part of an expression vector expressing any one or more of the aforementioned PDX-1, Pax-4, MafA, NeuroD1, and/or Sox-9 polypeptides, or fragments, derivatives or analogs thereof, within a suitable host. In one embodiment, such a nucleic acid possesses a promoter that is operably linked to coding region(s) of a PDX-1, Pax-4, MafA, NeuroD1 and Sox-9 polypeptide. The promoter may be inducible or constitutive, and, optionally, tissue-specific. The promoter may be, e.g., viral or mammalian in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. Proc Natl Acad Sci USA 86: 8932-8935. In yet another embodiment, the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In another embodiment, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. J Biol Chem 262: 4429-4432), which can be used to "target" cell types that specifically express the receptors of interest, etc.

An additional approach to gene therapy involves transferring a gene or mRNA into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In another embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. Meth Enzymol 217: 599-618. The chosen technique should provide for the stable transfer of the nucleic acid to the cell, such that the nucleic acid is expressible by the cell. In yet another embodiment, said transferred nucleic acid is heritable and expressible by the cell progeny. In an alternative embodiment, the transferred nucleic acid remains episomal and induces the expression of the otherwise silent endogenous nucleic acid.

In one embodiment, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total number of cells that are envisioned for use depend upon the desired effect, patient state, and the like, and may be determined by one skilled within the art. In one embodiment, at least $10^6$ transdifferentiated cells are needed for use in a method of treating as disclosed herein. In another embodiment, at least $10^7$ transdifferentiated cells, at least $10^8$ transdifferentiated cells, at least $10^9$ transdifferentiated cells, or at least $10^{10}$ transdifferentiated cells are needed for use in a method of treating as disclosed herein. In yet another embodiment, about $1.8 \times 10^9$ transdifferentiated cells are needed for use in a method of treating as disclosed herein.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle that is suitable for administration to an animal e.g., physiological saline. A therapeutically effective amount is an amount that is capable of producing a medically desirable result, e.g., an increase of a pancreatic gene in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. For example the DNA is administers at approximately $2 \times 10^{12}$ virions per Kg.

Methods of Manufacturing Human Insulin Producing (IP) Cells

Figure 32:
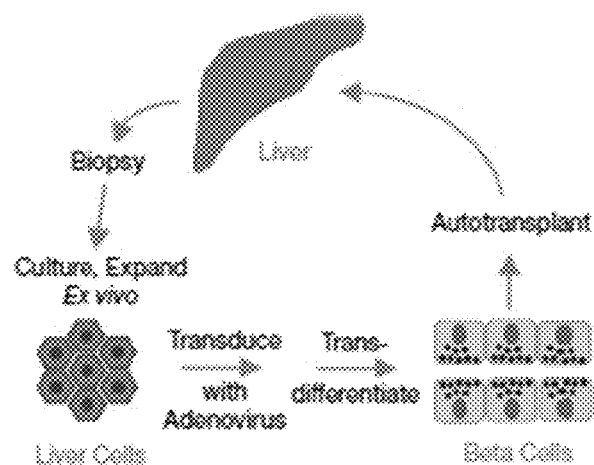
FIG. 32 presents a liver cell-based autologous cell therapy schema, adapted from Cozar-Castellan and Stewart (2005) Proc Nat Acad Sci USA 102(22): 7781-7782.

Manufacturing of human insulin producing cells may overcome the shortage of tissue available for cell-based therapies, for instance for treating a subject suffering from type I Diabetes Mellitus. Methods of manufacturing human insulin producing cells in sufficient numbers, in one embodiment, provides a cell-based product for use in these and other therapies, as disclosed herein (FIG. 32).

Figure 34:
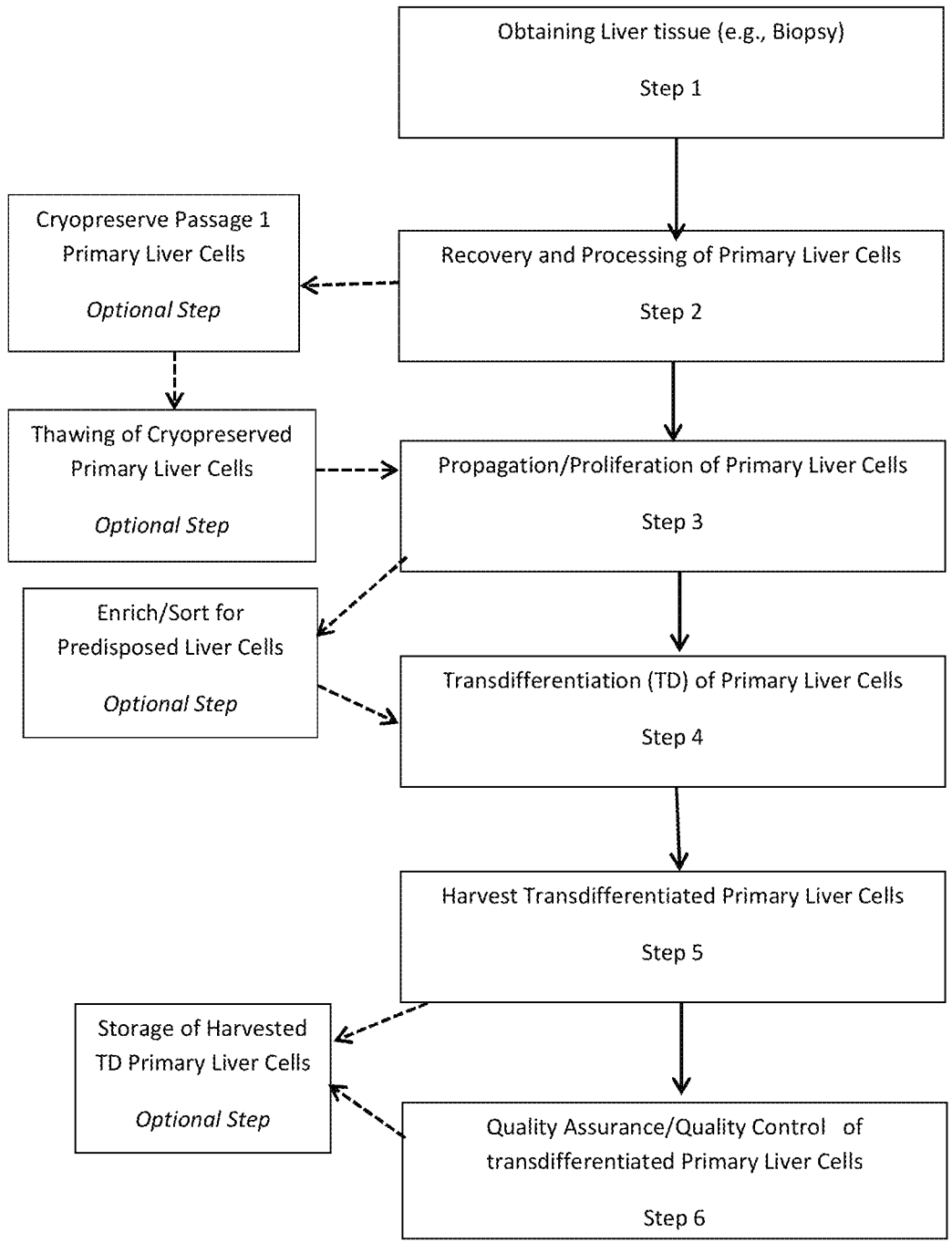
FIG. 34 presents an overview of the autologous insulin-producing (AIP) cell manufacturing process. Steps include: Step 1—Obtaining liver tissue (e.g., a liver biopsy); Step 2—Processing of the tissue to recover primary liver cells; Step 3—Propagating the primary liver cells to predetermined cell number; Step 4—Transdifferentiation of the primary liver cells; Step 5—Harvesting of the primary transdifferentiated liver cells; and Step 6—testing the transdifferentiated cells for quality assurance and quality control (i.e., safety, purity and potency). Optional steps include cryopreserving early passage primary liver cells, where in one embodiment an early passage is passage 1; thawing cryopreserved cells for use at a later date and storage of transdifferentiated cells for use at a later date.

Reference is now made to FIG. 34, which presents a flowchart of a manufacturing process of the human insulin producing cell product, which may in one embodiment be autologous or allogeneic insulin producing cells (AIP). FIG. 34 describes one embodiment of a manufacturing process of human insulin producing cells, wherein the starting material comprises liver tissue. A skilled artisan would recognize that any source of non-pancreatic β-cell tissue could be used in this manufacturing process.

Embodiments for many of the steps presented in FIG. 34 are described in detail throughout this application, and will not be repeated herein, though they should be considered herein. Reference is also made to Examples 20 and 21, which exemplify many of these steps. In brief, the manufacturing process may be understood based on the steps presented below.

As indicated at Step 1: Obtaining Liver Tissue. In one embodiment, liver tissue is human liver tissue. In another embodiment, the liver tissue is obtained as part of a biopsy. In another embodiment, liver tissue is obtained by way of any surgical procedure known in the art. In another embodiment, obtaining liver tissue is performed by a skilled medical practitioner. In another embodiment, liver tissue obtained is liver tissue from a healthy individual. In a related embodiment, the healthy individual is an allogeneic donor for a patient in need of a cell-based therapy that provides processed insulin in a glucose regulated manner, for example a type I Diabetes mellitus patient or a patient suffering for pancreatitis. In another embodiment, donor Screening and Donor Testing was performed to ensure that tissue obtained from donors shows no clinical or physical evidence of or risk factors for infectious or malignant diseases were from manufacturing of AIP cells. In yet another embodiment, liver tissue is obtained from a patient in need of a cell-based therapy that provides processed insulin in a glucose regulated manner, for example a type I Diabetes mellitus patient or a patient suffering for pancreatitis. In still another embodiment, liver tissue is autologous with a patient in need of a cell-based therapy that provides processed insulin in a glucose regulated manner, for example a type I Diabetes mellitus patient or a patient suffering for pancreatitis.

Figure 33:
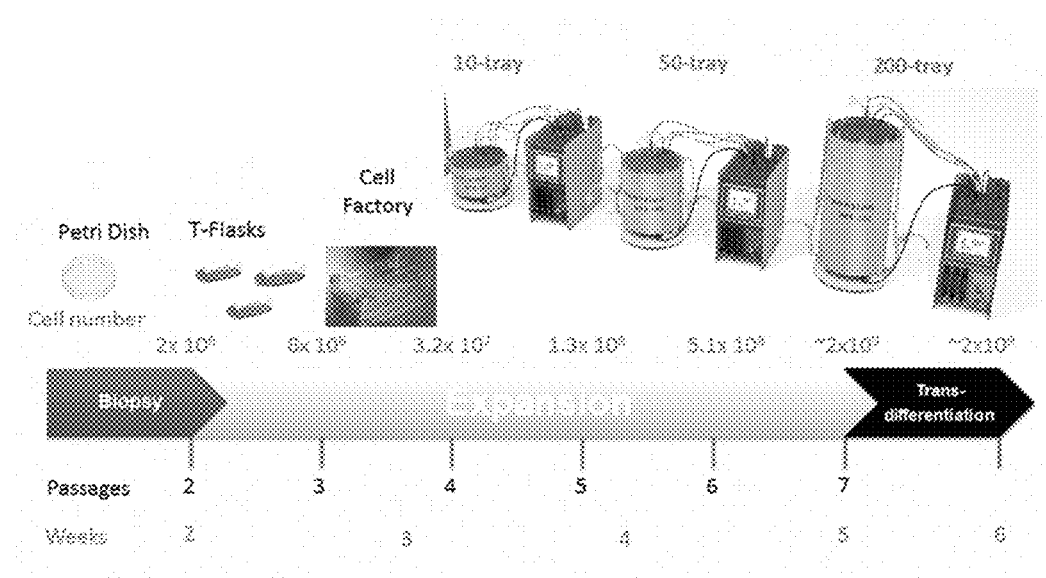
FIG. 33 presents a manufacturing process showing adult human primary liver cells undergoing a 1,000-fold expansion before transdifferentiation and final quality assurance/quality control (QA/QC) testing.

As indicated at Step 2: Recovery and Processing of Primary Liver Cells. Liver tissue is processed using well know techniques in the art for recovery of adherent cells to be used in further processing. In one embodiment, liver tissue is cut into small pieces of about 1-2 mm and gently pipetted up and down in sterile buffer solution. The sample may then be incubated with collagenase to digest the tissue. Following a series of wash steps, in another embodiment, primary liver cells may be plated on pre-treated fibronectin-coated tissue culture tissue dishes. The skilled artisan would know well how to then process (passage) the cells following well-known techniques for propagation of liver cells. Briefly, cells may be grown in a propagation media and through a series of seeding and harvesting cell number is increased. Cells may be split upon reaching 80% confluence and re-plated. FIG. 33 (0-2 weeks) shows a schematic of one embodiment of this recovery and process step representing 2 passages of the primary liver cells.

A skilled artisan would appreciate the need for sufficient cells at, for example the 2 week time period, prior to beginning the expansion phase of the protocol (step 3). The skilled artisan would recognize that the 2-week time period is one example of a starting point for expanding cells, wherein cells may be ready for expansion be before or after this time period. In one embodiment, recovery and processing of primary cells yields at least $1 \times 10^5$ cells after two passages of the cells. In another embodiment, recovery and processing of primary cells yields at least $1 \times 10^6$ cells after two passages of the cells. In another embodiment, recovery and processing of primary cells yields at least $2 \times 10^6$ cells after two passages of the cells. In another embodiment, recovery and processing of primary cells yields at least $5 \times 10^6$ cells after two passages of the cells. In another embodiment, recovery and processing of primary cells yields at least $1 \times 10^7$ cells after two passages of the cells. In another embodiment, recovery and processing of primary cells yields between $1 \times 10^5$-$1 \times 10^6$ cells after two passages of the cells. In another embodiment, recovery and processing of primary cells yields between $1 \times 10^6$-$1 \times 10^7$ cells after two passages of the cells. In another embodiment, enough starting tissue is used to ensure the recovery and processing of primary cells yields enough cells after two passages for an adequate seeding density at Step 3, large-scale expansion of the cells.

In one embodiment, 1 passage primary cells are cryopreserved for later use. In another embodiment, early passage primary cells are cryopreserved for later use. In yet another embodiment, $2^{nd}$ passage primary cells are cryopreserved for later use.

As indicated at Step 3: Propagation/Proliferation of Primary Liver Cells

Step 3 represents the large-scale expansion phase of the manufacturing process. A skilled artisan would appreciate the need for sufficient cells at the 5 week time period, prior to beginning the transdifferentiation phase of the protocol (step 4), wherein a predetermined number of cells may be envisioned to be needed for treating a patient. In one embodiment, the predetermined number of cells needed prior to transdifferentiation comprises about $1 \times 10^8$ primary cells. In another embodiment, the predetermined number of cells needed prior to transdifferentiation comprises about $2\times10^8$ primary cells. In one embodiment, the predetermined number of cells needed prior to transdifferentiation comprises about $3\times10^8$ primary cells, $4\times10^8$ primary cells, $5\times10^8$ primary cells, $6\times10^8$ primary cells, $7\times10^8$ primary cells, $8\times10^8$ primary cells, $9\times10^8$ primary cells, $1\times10^9$ primary cells, $2\times10^9$ primary cells, $3\times10^9$ primary cells, $4\times10^9$ primary cells, $5\times10^9$ primary cells, $6\times10^9$ primary cells, $7\times10^9$ primary cells, $8\times10^9$ primary cells, $9\times10^9$ primary cells, or $1\times10^{10}$ primary cells.

In one embodiment, the cell seeding density at the time of expansion comprises $1\times10^3$-$10\times10^3$ cell/cm$^2$. In another embodiment, the cell seeding density at the time of expansion comprises $1\times10^3$-$8\times10^3$ cell/cm$^2$. In another embodiment, the cell seeding density at the time of expansion comprises $1\times10^3$-$5\times10^3$ cell/cm$^2$. In another embodiment, the cell seeding density at the time of expansion comprises $1\times10^3$. In another embodiment, the cell seeding density at the time of expansion comprises $2\times10^3$. In another embodiment, the cell seeding density at the time of expansion comprises $3\times10^3$. In another embodiment, the cell seeding density at the time of expansion comprises $4\times10^3$. In another embodiment, the cell seeding density at the time of expansion comprises $5\times10^3$. In another embodiment, the cell seeding density at the time of expansion comprises $6\times10^3$. In another embodiment, the cell seeding density at the time of expansion comprises $7\times10^3$. In another embodiment, the cell seeding density at the time of expansion comprises $8\times10^3$. In another embodiment, the cell seeding density at the time of expansion comprises $9\times10^3$. In another embodiment, the cell seeding density at the time of expansion comprises $10\times10^3$.

In another embodiment, the range for cells seeding viability at the time of expansion comprises 60-100%. In another embodiment, the range for cells seeding viability at the time of expansion comprises a viability of about 70-99%. In another embodiment, the cell seeding viability at the time of expansion comprises a viability of about 60%. In another embodiment, the cell seeding viability at the time of expansion comprises a viability of about 65%. In another embodiment, the cell seeding viability at the time of expansion comprises a viability of about 70%. In another embodiment, the cell seeding viability at the time of expansion comprises a viability of about 75%. In another embodiment, the cell seeding viability at the time of expansion comprises a viability of about 80%. In another embodiment, the cell seeding viability at the time of expansion comprises a viability of about 85%. In another embodiment, the cell seeding viability at the time of expansion comprises a viability of about 90%. In another embodiment, the cell seeding viability at the time of expansion comprises a viability of about 95%. In another embodiment, the cell seeding viability at the time of expansion comprises a viability of about 99%. In another embodiment, the cell seeding viability at the time of expansion comprises a viability of about 99.9%.

Figure 28:
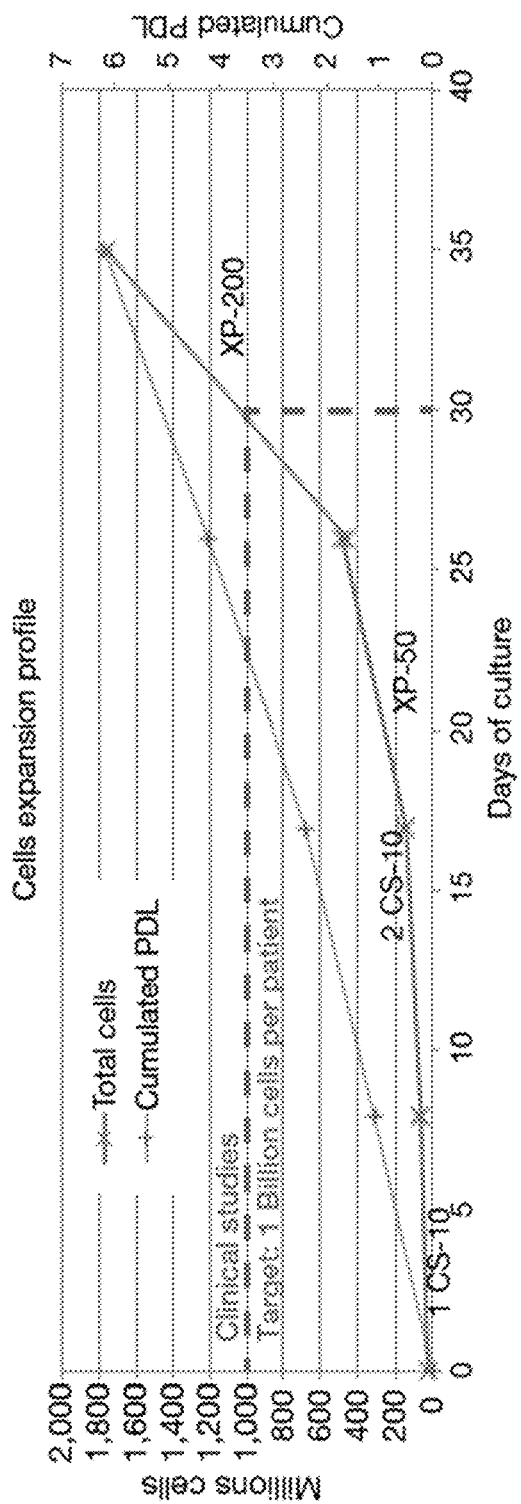
FIG. 28 presents a typical seed train and cell expansion profile of human liver-derived primary cells from multi-tray Cell Stack (CS) 10 plates to the XP-200 bioreactor. Dotted lines in green represent a target in terms of numbers of cells required per patient (targeting diabetes cell-based autologous therapy), wherein the target number shown is 1 billion cells per patient. PDL represents Population Doubling Limit. CS represents Cell Stack multitrays.
Figure 29:
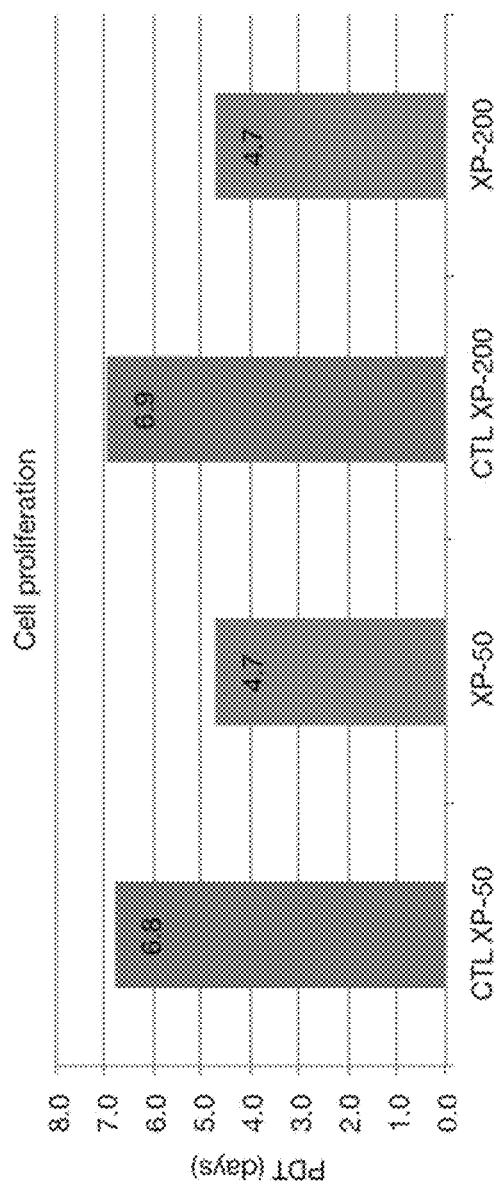
FIG. 29 presents Population Doubling Time (PDT) in days in the XP-50 and XP-200 bioreactors and in their control classic multi-tray support counterparts (CTL XP50 and CTL XP-200). The data is based on harvested cell densities. The numbers in each bar represent the PDT.

FIG. 33 schematically illustrates one embodiment of this expansion period. In one embodiment, expansion occurs between weeks 2 and 5. The skilled artisan would recognize variability within starting tissue material (FIG. 29). Therefore, in another embodiment expansion occurs between weeks 2 and 6. In still another embodiment, expansion occurs between weeks 2 and 7. In another embodiment, expansion occurs between weeks 2 and 4. In yet another embodiment, expansion occurs until the needed number of primary cells has been propagated. For example, FIG. 28 shows that a target goal of 1 billion cells was reached by day 30 of culture.

A skilled artisan would appreciate that concurrent with expansion of cells, the population could be enhanced for transdifferentiation. Description of primary adult liver cells enhanced for transdifferentiation and methods for enriching these populations have been disclosed herein, and are exemplified in Examples 10-17 and 23. In one embodiment, selection for GSRE activity is used to enrich a population of adult cells for transdifferentiation. In another embodiment, levels of gene expression are measured for genes known to have either increased or decreased expression, wherein such increases or decreases indicate predisposition to transdifferentiation. In another embodiment, primary adult liver cells may be incubated with lithium prior to transdifferentiation, wherein the incubation enhances predisposition of a population of cells within said population of primary adult liver cells.

In one embodiment, bioreactors are used to expand and propagate primary cells prior to the transdifferentiation step. Bioreactors may be used for cultivation of cells, in which conditions are suitable for high cell concentrations (See Example 20). In another embodiment, a bioreactor provides a closed system for expansion of cells. In another embodiment, multiple bioreactors are used in a series for cell expansion. In another embodiment, a bioreactor used in the methods disclosed herein is a single use bioreactor. In another embodiment, a bioreactor used is a multi-use bioreactor. In yet another embodiment, a bioreactor comprises a control unit for monitoring and controlling parameters of the process. In another embodiment, parameters for monitoring and controlling comprise Dissolve Oxygen (DO), pH, gases, and temperature.

As indicated at Step 4: Transdifferentiation (TD) of primary Liver Cells.

In one embodiment, transdifferentiation comprises any method of transdifferentiation disclosed herein. For example, transdifferentiation may comprise a hierarchy (1+1+1) protocol or a "2+1" protocol, as disclosed herein.

In one embodiment, the resultant cell population following transdifferentiation comprises transdifferentiated cells having a pancreatic phenotype and function. In another embodiment, the resultant cell population following transdifferentiation comprises transdifferentiated cells having a mature β-cell pancreatic phenotype and function. In another embodiment, the resultant cell population following transdifferentiation comprises transdifferentiated cells having increased insulin content. In another embodiment, the resultant cell population following transdifferentiation comprises transdifferentiated cells able to secrete processed insulin in a glucose-regulated manner. In another embodiment, the resultant cell population following transdifferentiation comprises transdifferentiated cells has increased C-peptide levels.

In another embodiment, the resultant cell population following transdifferentiation comprises transdifferentiated cells having increased endogenous expression of at least one pancreatic gene marker. In another embodiment, endogenous expression is increased for at least two pancreatic gene markers. In another embodiment, endogenous expression is increased for at least three pancreatic gene markers. In another embodiment, endogenous expression is increased for at least four pancreatic gene markers. In a related embodiment, pancreatic gene markers comprise PDX-1, NeuroD1, MafA, Nkx6.1, glucagon, somatostatin and Pax4.

In one embodiment, endogenous PDX-1 expression is greater than $10^2$ fold over non-differentiated cells. In another embodiment, endogenous PDX-1 expression is greater than $10^3$ fold over non-differentiated cells. In another embodiment, endogenous PDX-1 expression is greater than $10^4$ fold over non-differentiated cells. In another embodiment, endogenous PDX-1 expression is greater than $10^5$ fold over non-differentiated cells. In another embodiment, endogenous PDX-1 expression is greater than $10^6$ fold over non-differentiated cells.

In another embodiment, endogenous NeuroD1 expression is greater than $10^2$ fold over non-differentiated cells. In another embodiment, endogenous NeuroD1 expression is greater than $10^3$ fold over non-differentiated cells. In another embodiment, endogenous NeuroD1 expression is greater than $10^4$ fold over non-differentiated cells. In another embodiment, endogenous NeuroD1 expression is greater than $10^5$ fold over non-differentiated cells.

In another embodiment, endogenous MafA expression is greater than $10^2$ fold over non-differentiated cells. In another embodiment, endogenous MafA expression is greater than $10^3$ fold over non-differentiated cells. In another embodiment, endogenous MafA expression is greater than $10^4$ fold over non-differentiated cells. In another embodiment, endogenous MafA expression is greater than $10^5$ fold over non-differentiated cells.

In another embodiment, endogenous glucagon expression is greater than 10 fold over non-differentiated cells. In another embodiment, endogenous glucagon expression is greater than $10^2$ fold over non-differentiated cells. In another embodiment, endogenous glucagon expression is greater than $10^3$ fold over non-differentiated cells.

In another embodiment, endogenous expression of PDX-1, NeuroD1, or MafA, or any combination thereof is each greater than 60% over non-differentiated cells. In another embodiment, endogenous expression of PDX-1, NeuroD1, or MafA, or any combination thereof is each greater than 70% over non-differentiated cells. In another embodiment, endogenous expression of PDX-1, NeuroD1, or MafA, or any combination thereof is each greater than 80% over non-differentiated cells In another embodiment, the resultant cell population following transdifferentiation comprises transdifferentiated cells having at least 60% viability. In another embodiment, the resultant cell population following transdifferentiation comprises transdifferentiated cells having at least 70% viability. In another embodiment, the resultant cell population following transdifferentiation comprises transdifferentiated cells having at least 80% viability. In another embodiment, the resultant cell population following transdifferentiation comprises transdifferentiated cells having at least 90% viability.

In another embodiment, the resultant cell population following transdifferentiation comprises transdifferentiated cells showing decreased liver cell markers. In another embodiment, the resultant cell population following transdifferentiation comprises transdifferentiated cells showing decreased albumin or alpha-1 antitrypsin (AAT), or any combination. In another embodiment, the resultant cell population following transdifferentiation comprises transdifferentiated cells comprising less than 1% by FACS albumin or alpha-1 antitrypsin (AAT), or any combination.

In another embodiment, transdifferentiated cells maintain a pancreatic phenotype and function for at least 6 months. In another embodiment, transdifferentiated cells maintain a pancreatic phenotype and function for at least 12 months. In another embodiment, transdifferentiated cells maintain a pancreatic phenotype and function for at least 18 months. In another embodiment, transdifferentiated cells maintain a pancreatic phenotype and function for at least 24 months. In another embodiment, transdifferentiated cells maintain a pancreatic phenotype and function for at least 36 months. In another embodiment, transdifferentiated cells maintain a pancreatic phenotype and function for at least 48 months. In another embodiment, transdifferentiated cells maintain a pancreatic phenotype and function for at least 4 years. In another embodiment, transdifferentiated cells maintain a pancreatic phenotype and function for at least 5 years.

In one embodiment, cell number is maintained during transdifferentiation. In another embodiment, cell number decreases by less than 5% during transdifferentiation. In another embodiment, cell number decreases by less than 10% during transdifferentiation. In another embodiment, cell number decreases by less than 15% during transdifferentiation. In another embodiment, cell number decreases by less than 20% during transdifferentiation. In another embodiment, cell number decreases by less than 25% during transdifferentiation.

As indicated at Step 5: Harvest Transdifferentiated Primary Liver Cells

In one embodiment, transdifferentiated primary liver cells comprising human insulin producing cells are harvested and used for a cell-based therapy. In one embodiment, cell number is maintained during harvesting. In another embodiment, cell number decreases by less than 5% during harvesting. In another embodiment, cell number decreases by less than 10% during harvesting. In another embodiment, cell number decreases by less than 15% during harvesting. In another embodiment, cell number decreases by less than 20% during harvesting. In another embodiment, cell number decreases by less than 25% during harvesting.

In one embodiment, the number of transdifferentiated cells recovered at harvest is about $1\times10^7$-$1\times10^{10}$ cells total. In another embodiment, the number of transdifferentiated cells recovered at harvest is about $1\times10^8$-$1\times10^{10}$ cells total. In another embodiment, the number of transdifferentiated cells recovered at harvest is about $1\times10^7$-$1\times10^9$ cells total. In another embodiment, the number of transdifferentiated cells recovered at harvest is about $1\times10^7$ cells total. In another embodiment, the number of transdifferentiated cells recovered at harvest is about $5\times10^7$ cells total. In another embodiment, the number of transdifferentiated cells recovered at harvest is about $7.5\times10^7$ cells total. In another embodiment, the number of transdifferentiated cells recovered at harvest is about $1\times10^8$ cells total. In another embodiment, the number of transdifferentiated cells recovered at harvest is about $2.5\times10^8$ cells total. In another embodiment, the number of transdifferentiated cells recovered at harvest is about $5\times10^8$ cells total. In another embodiment, the number of transdifferentiated cells recovered at harvest is about $7.5\times10^8$ cells total. In another embodiment, the number of transdifferentiated cells recovered at harvest is about $1\times10^9$ cells total. In another embodiment, the number of transdifferentiated cells recovered at harvest is about $2\times10^8$ cells total. In another embodiment, the number of transdifferentiated cells recovered at harvest is about $3\times10^8$ cells total. In another embodiment, the number of transdifferentiated cells recovered at harvest is about $4\times10^9$ cells total. In another embodiment, the number of transdifferentiated cells recovered at harvest is about $5\times10^9$ cells total. In another embodiment, the number of transdifferentiated cells recovered at harvest is about $6\times10^9$ cells total. In another embodiment, the number of transdifferentiated cells recovered at harvest is about $7\times10^9$ cells total. In another embodiment, the number of transdifferentiated cells recovered at harvest is about $8 \times 10^9$ cells total. In another embodiment, the number of transdifferentiated cells recovered at harvest is about $9 \times 10^9$ cells total.

In one embodiment, the density of transdifferentiated cells at harvest is about $1 \times 10^3$-$1 \times 10^5$ cells/cm$^2$. In another embodiment, the density of transdifferentiated cells at harvest is about $1 \times 10^4$-$5 \times 10^4$ cells/cm$^2$. In another embodiment, the density of transdifferentiated cells at harvest is about $1 \times 10^4$-$4 \times 10^4$ cells/cm$^2$. In another embodiment, the density of transdifferentiated cells at harvest is about $1 \times 10^3$ cells/cm$^2$. In another embodiment, the density of transdifferentiated cells at harvest is about $2 \times 10^3$ cells/cm$^2$. In another embodiment, the density of transdifferentiated cells at harvest is about $3 \times 10^3$ cells/cm$^2$. In another embodiment, the density of transdifferentiated cells at harvest is about $4 \times 10^3$ cells/cm$^2$. In another embodiment, the density of transdifferentiated cells at harvest is about $5 \times 10^3$ cells/cm$^2$. In another embodiment, the density of transdifferentiated cells at harvest is about $6 \times 10^3$ cells/cm$^2$. In another embodiment, the density of transdifferentiated cells at harvest is about $7 \times 10^3$ cells/cm$^2$. In another embodiment, the density of transdifferentiated cells at harvest is about $8 \times 10^3$ cells/cm$^2$. In another embodiment, the density of transdifferentiated cells at harvest is about $9 \times 10^3$ cells/cm$^2$. In another embodiment, the density of transdifferentiated cells at harvest is about $1 \times 10^4$ cells/cm$^2$. In another embodiment, the density of transdifferentiated cells at harvest is about $2 \times 10^4$ cells/cm$^2$. In another embodiment, the density of transdifferentiated cells at harvest is about $3 \times 10^4$ cells/cm$^2$. In another embodiment, the density of transdifferentiated cells at harvest is about $4 \times 10^4$ cells/cm$^2$. In another embodiment, the density of transdifferentiated cells at harvest is about $5 \times 10^4$ cells/cm$^2$. In another embodiment, the density of transdifferentiated cells at harvest is about $6 \times 10^4$ cells/cm$^2$. In another embodiment, the density of transdifferentiated cells at harvest is about $7 \times 10^4$ cells/cm$^2$. In another embodiment, the density of transdifferentiated cells at harvest is about $8 \times 10^4$ cells/cm$^2$. In another embodiment, the density of transdifferentiated cells at harvest is about $9 \times 10^4$ cells/cm$^2$.

In another embodiment, the range for cell viability at the time of harvesting comprises 50-100%. In another embodiment, the range for cell viability at the time of harvesting comprises 60-100%. In another embodiment, the range for cell viability at the time of harvesting comprises 50-90%. In another embodiment, the range for cell viability at the time of harvesting comprises a viability of about 60-99%. In another embodiment, the range for cell viability at the time of harvesting comprises a viability of about 60-90%. In another embodiment, the cell viability at the time of harvesting comprises a viability of about 60%. In another embodiment, the cell viability at the time of harvesting comprises a viability of about 65%. In another embodiment, the cell viability at the time of harvesting comprises a viability of about 70%. In another embodiment, the cell viability at the time of harvesting comprises a viability of about 75%. In another embodiment, the cell viability at the time of harvesting comprises a viability of about 80%. In another embodiment, the cell viability at the time of harvesting comprises a viability of about 85%. In another embodiment, the cell viability at the time of harvesting comprises a viability of about 90%. In another embodiment, the cell viability at the time of harvesting comprises a viability of about 95%. In another embodiment, the cell viability at the time of harvesting comprises a viability of about 99%. In another embodiment, the cell viability at the time of harvesting comprises a viability of about 99.9%.

In another embodiment, transdifferentiated primary liver cells comprising human insulin producing cells are harvested and stored for use in a cell-based therapy at a later date. In another embodiment, storage comprises cryopreserving the cells.

As indicated at Step 6: Quality Analysis/Quality Control

Before any use of transdifferentiated cells in a cell-based therapy, the transdifferentiated cells must undergo a quality analysis/quality control assessment. FACS analysis and/or RT-PCR may be used to accurately determine membrane markers and gene expression. Further, analytical methodologies for insulin secretion are well known in the art including ELISA, MSD, ELISpot, HPLC, RP-HPLC. In one embodiment, insulin secretion testing is at low glucose concentrations (about 2 mM) in comparison to high glucose concentrations (about 17.5 mM).

Therapeutics Compositions

The herein-described transdifferentiation-inducing compounds, or ectopic pancreatic transcription factors (i.e., PDX-1, Pax-4, MafA, NeuroD1 or Sox-9 polypeptides, ribonucleic acids or nucleic acids encoding PDX-1, Pax-4, MafA, NeuroD1 or Sox-9 polypeptides) and the cells having a pancreatic beta cell phenotype produced by the methods disclosed here, when used therapeutically, are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the disclosure presented herein may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local, e.g. through portal vein delivery to the liver. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the disclosure presented herein including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. J Biol Chem 262:4429-4432); (iv) construction of a Therapeutic nucleic acid as part of a retroviral, adenoviral or other vector, and the like. In one embodiment of the disclosure presented herein, the Therapeutic may be delivered in a vesicle, in particular a liposome. In a liposome, the protein of the disclosure presented herein is combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like.

Preparation of such liposomal formulations is within the level of skill in the art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, e.g.: a delivery pump (See, e.g., Saudek, et al., 1989. New Engl J Med 321:574 and a semi-permeable polymeric material (See, e.g., Howard, et al., 1989. J Neurosurg 71:105). Additionally, the controlled release system can be placed in proximity of the therapeutic target (e.g., the brain), thus requiring only a fraction of the systemic dose. See, e.g., Goodson, In: Medical Applications of Controlled Release 1984. (CRC Press, Boca Raton, Fla.).

In one embodiment of the disclosure presented herein, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. Proc Natl Acad Sci USA 88:1864-1868), and the like. Alternatively, a nucleic acid Therapeutic can be introduced intracellularly and incorporated within host cell DNA for expression, by homologous recombination or remain episomal.

In one embodiment, the Therapeutic is a cell having pancreatic beta cell phenotype produced by the methods disclosed here and, the Therapeutic is administered intravenously. Specifically, the Therapeutic can be delivered via a portal vein infusion.

A skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Suitable dosage ranges for intravenous administration of the Therapeutics of the disclosure presented herein are generally at least 1 million transdifferentiated cells, at least 2 million transdifferentiated cells, at least 5 million transdifferentiated cells, at least 10 million transdifferentiated cells, at least 25 million transdifferentiated cells, at least 50 million transdifferentiated cells, at least 100 million transdifferentiated cells, at least 200 million transdifferentiated cells, at least 300 million transdifferentiated cells, at least 400 million transdifferentiated cells, at least 500 million transdifferentiated cells, at least 600 million transdifferentiated cells, at least 700 million transdifferentiated cells, at least 800 million transdifferentiated cells, at least 900 million transdifferentiated cells, at least 1 billion transdifferentiated cells, at least 2 billion transdifferentiated cells, at least 3 billion transdifferentiated cells, at least 4 billion transdifferentiated cells, or at least 5 billion transdifferentiated cells. In one embodiment, the dose is 1-2 billion transdifferentiated cells into a 60-75 kg subject. One skilled in the art would appreciate that effective doses may be extrapolated from dose-response curves derived from in vitro or animal model test systems. In another embodiment, the effective dose may be administered intravenously into the liver portal vein.

Cells may also be cultured ex vivo in the presence of therapeutic agents, nucleic acids, or proteins of the disclosure presented herein in order to proliferate or to produce a desired effect on or activity in such cells. Treated cells can then be introduced in vivo via the administration routes described herein for therapeutic purposes.

Pharmaceutical Compositions

The compounds, e.g., PDX-1, Pax-4, MafA, NeuroD1, or Sox-9 polypeptides, nucleic acids encoding PDX-1, Pax-4, MafA, NeuroD1, or Sox-9 polypeptides, or a nucleic acid or compound that increases expression of a nucleic acid that encodes PDX-1, Pax-4, MafA, NeuroD1, or Sox-9 polypeptides (also referred to herein as "active compounds") and derivatives, fragments, analogs and homologs thereof and pancreatic beta cells produced by the methods disclosed here, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solution, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition disclosed here is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists.

It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed here are dictated by and directly dependent on the unique characteristics of the active compound and the particular therapeutic effect to be achieved.

The nucleic acid molecules disclosed here can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

It should be understood that the disclosure presented herein is not limited to the particular methodologies, protocols and reagents, and examples described herein. The terminology and examples used herein is for the purpose of describing particular embodiments only, for the intent and purpose of providing guidance to the skilled artisan, and is not intended to limit the scope of the disclosure presented herein.

EXAMPLES

Example 1: General Methods

Human Liver Cells

Adult human liver tissues were obtained from individuals 3-23 years old or older. Liver tissues were used with the approval from the Committee on Clinical Investigations (the institutional review board). The isolation of human liver cells was performed as described (Sapir et al, (2005) Proc Natl Acad Sci USA 102: 7964-7969; Meivar-Levy et al, (2007) Hepatology 46: 898-905). The cells were cultured in Dulbecco's minimal essential medium (1 g/l of glucose) supplemented with 10% fetal calf serum, 100 units/ml penicillin; 100 ng/ml streptomycin; 250 ng/ml amphotericin B (*Biological Industries*, Beit Haemek, Israel), and kept at 37° C. in a humidified atmosphere of 5% $CO_2$ and 95% air.

Viral Infection

The adenoviruses used in this study were as follows: Ad-CMV-Pdx-1 (Sapir et al, 2005 ibid; Meivar-Levy et al, 2007 ibid), Ad-RIP-luciferase (Seijffers et al, (1999) Endocrinology 140: 3311-3317), Ad-CMV-β-Gal, Ad-CMV-MafA (generous gift from Newgard, C. B., Duke University), Ad-CMV-Pax4-IRES-GFP (generous gift from St Onge, L. DeveloGen AG, Gottingen, Germany), and Ad-CMV-Isl1 (generous gift from Kieffer, T. University of British Columbia, Vancouver, Canada). The viral particles were generated by the standard protocol (He et al, (1998) Proc Natl Acad Sci USA 95: 2509-2514).

Liver cells were infected with recombinant adenoviruses for 5-6 days (Table 1) supplemented with EGF (20 ng/ml; Cytolab, Ltd., Israel) and nicotinamide (10 mM; Sigma). The optimal multiplicity of infection (MOI) was determined according to cell survival (<75%) and induction of C-peptide secretion. The MOI of the viruses used were; Ad-CMV-Pdx-1 (1000 MOI), Ad-CMV-Pax4-IRES-GFP (100 MOI), Ad-CMV-MafA (10 MOI) and Ad-CMV-Isl1 (100 MOI).

RNA Isolation, RT and RT-PCR Reactions

Total RNA was isolated and cDNA was prepared and amplified, as described previously (Ber et al, (2003) J Biol Chem 278: 31950-31957; Sapir et al, (2005) ibid). Quantitative real-time RT-PCR was performed using ABI Step one plus sequence Detection system (*Applied Biosystems*, CA, USA), as described previously (Sapir et al, (2005) ibid; Meivar-Levy et al, (2007) ibid; Aviv et al, (2009) J Biol Chem 284: 33509-33520).

C-Peptide and Insulin Secretion Detection

C-peptide and insulin secretion were measured by static incubations of primary cultures of adult liver cells 6 days after the initial exposure to the viral treatment, as described (Sapir et al, (2005) ibid; Meivar-Levy et al, (2007) ibid; Aviv et al, (2009) ibid). The glucose-regulated C-peptide secretion was measured at 2 mM and 17.5 mM glucose, which was determined by dose-dependent analyses to maximally induce insulin secretion from transdifferentiated liver cells, without having adverse effects on treated cells function (Sapir et al, (2005) ibid; Meivar-Levy et al, (2007) ibid; Aviv et al, (2009) ibid). C-peptide secretion was detected by radioimmunoassay using the human C-peptide radioimmunoassay kit (Linco Research, St. Charles, Mo.; <4% cross-reactivity to human proinsulin). Insulin secretion was detected by radioimmunoassay using human insulin radioimmunoassay kit (DPC, Angeles, Calif.; 32% cross-reactivity to human proinsulin). The secretion was normalized to the total cellular protein measured by a Bio-Rad protein assay kit.

Luciferase Assay

Human liver cells were co-infected with Ad-RIP-luciferase (200 moi) and the various adenoviruses (as described below). Six days later, luciferase activity was measured using the Luciferase assay System (Promega) and the LKB 1250 Luminometer (LKB, Finland). The results were normalized to total cellular protein measured by the Bio-Rad Protein Assay kit (Bio-Rad).

Immunofluorescence

Human liver cells treated with the various adenoviruses, were plated on glass cover slides in 12-well culture plates ($2 \times 10^5$ cells/well). 3-4 days later, the cells were fixed and stained as described (Sapir et al, (2005) ibid; Meivar-Levy et al, (2007) ibid; Aviv et al, (2009) ibid). The antibodies used in this study were: anti-rabbit PDX-1, anti-goat PDX-1 (both 1:1000 a generous gift from C. V. E. Wright), anti-human insulin, anti-human somatostatin (both 1:100, Dako, Glostrup, Denmark), anti-Pax4 (1:100; R&D Systems, Minneapolis, Minn.), anti-MafA (1:160; Santa Cruz Biotechnology, Inc., Santa Cruz, Calif.). The secondary antibodies used were: anti-rabbit IgG Cyanine (cy2) conjugated antibody 1:250, anti-rabbit IgG indocarbocyanine (cy3) conjugated antibody 1:250, anti-goat IgG Cyanine (cy2) conjugated antibody 1:200, anti-goat IgG indocarbocyanine (cy3) conjugated antibody 1:250, and anti-mouse IgG indocarbocyanine (cy3) conjugated antibody 1:250 (all from *Jackson ImmunoResearch*, PA). Finally, the cells were stained with 4',6-diamidino-2-phenyl-indole (DAPI, Sigma). The slides were imaged and analyzed using a fluorescent microscope (Provis, Olympus).

Purity Assays

A flow cytometry based assay has been developed as the principal purity assay to ensure that more than 90% of the cells during expansion and transdifferentiation have a mesenchymal stem cell (MSC) like phenotype. Cultivated MSCs should stain positive for CD73, CD90, CD105 and CD44 and should be negative for CD45, CD34, CD14 or CD11b, CD19 or CD79α, and HLA-DR surface molecules.

Figures 44A, 44B:
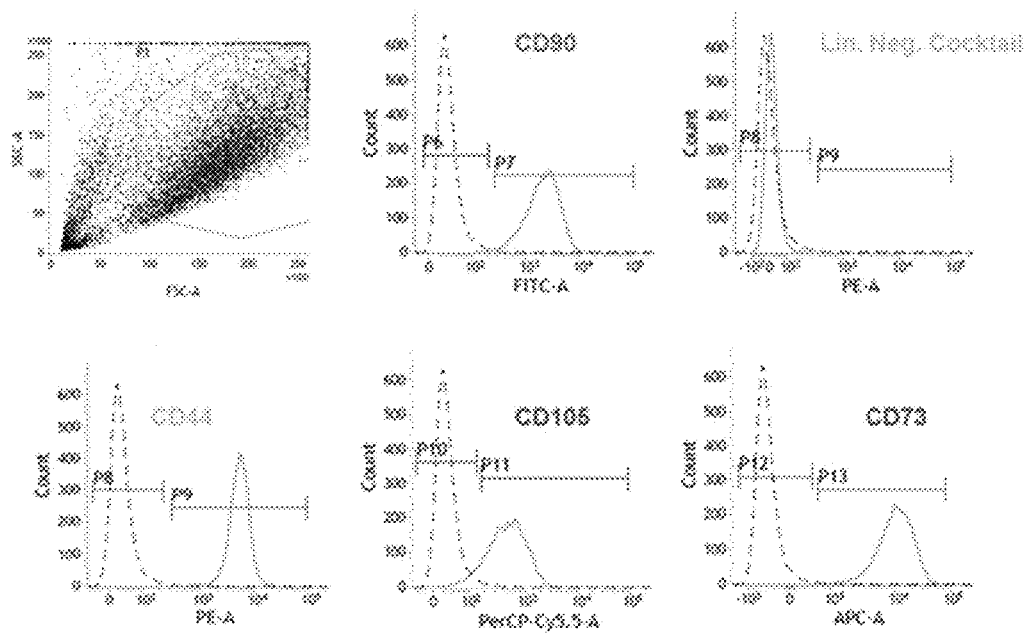
FIGS. 44A and 44B present the results of flow cytometry analysis of expanded and transdifferentiated liver cells.

As shown in FIGS. 44A and 44B, expanded liver cells and infected cells expressed CD90, CD44, CD105 and CD73 markers at high levels (≥90%) while they did not express lineage negative markers (cocktail of CD34, CD11b, CD45, CD19 and HLA-DR). To note, CD105 expression was slightly decreased in infected cells at P16 compared to non-infected cells at P14. Additional experiments are needed to understand if this decrease is significant and if it decreases with passage numbers or with transdifferentiation. These results demonstrate that MSC markers were stable over time and during transdifferentiation of liver cells. Flow cytometry for MSC markers may be indeed used as a QC test.

Next step will be to develop flow cytometry or Immunofluorescence assays to quantify the subpopulations expressing or co-expressing the various exogenous transcription factors and ideally insulin or C-peptide.

Statistical Analysis

Statistical analyses were performed with a 2-sample Student t-test assuming unequal variances.

Example 2: PDX-1-Induced Transdifferentiation

Previous studies (Sapir et al, (2005) ibid; Meivar-Levy et al, (2007) ibid; Aviv et al, (2009) ibid; Gefen-Halevi et al, (2010) Cell Reprogram 12: 655-664; Meivar-Levy et al, (2011) J Transplant 2011: 252387) have suggested that PDX-1 alone is capable of inducing β-cell like phenotype and function in human liver cells, possibly due to its capacity to activate numerous otherwise silent endogenous pTFs in liver. The activation of the pancreatic lineage was fast and occurred within 5 days (Sapir et al, (2005) ibid, Ber et al, (2003) ibid)

In this example, the sequence of events that mediate PDX-1 induced liver to pancreas transdifferentiation is examined Adenoviral vectors encoding Pdx-1 were introduced to adult human liver cells, and the effects of ectopic PDX-1 expression were monitored for four consecutive days post infection (Days 2-5; FIGS. 1A-1D). Pancreatic hormone and pancreas-specific transcription factor expression was determined by quantitative RT-PCR analysis every day for 5 days. Results were normalized to β-actin gene expression within the same cDNA sample and are presented as the mean±SE of the relative expression versus control virus (Ad-CMV-β-gal, 1000 MOI) treated cells on the same day. Two independent experiments were performed, with n≥4, *p<0.05 and **p<0.01.

Both glucagon and somatostatin genes were immediately activated, within one day after Ad-Pdx-1 infection (FIGS. 1B and 1C). However, insulin expression was only detected on the fourth to fifth day post-infection (FIG. 1A). To provide a mechanistic explanation for the distinct temporal activation of the three major pancreatic hormones, expression levels of endogenously activated transcription factors were analyzed during the transdifferentiation process. The early pancreatic endocrine transcription factors, NGN3 and NEUROD1 were immediately activated (FIG. 1D). However, β-cell specific TFs, such as NKX6.1 and MafA, were only gradually and modestly activated in response to ectopic PDX-1 expression, reaching their peak expression level on the fourth and fifth day, respectively. The activation of insulin gene expression on the fifth day was associated not only with an increase in MafA expression but also with a decrease in Isl1 expression (FIG. 1D). These data suggest that transdifferentiation of human liver cells along the pancreatic lineage, despite being rapid, is a gradual and consecutive process. The distinct temporal activation of pancreatic hormone gene expression (such as somatostatin and glucagon) can be partially attributed to the time course and the relative levels of the endogenously activated pTFs expression.

Example 3: Combined Expression of Pdx-1, Pax4 and Mafa Increases the Efficiency of Liver to Pancreas Transdifferentiation Previous studies have suggested that the concerted expression of several pTFs increases the transdifferentiation efficiency along the β-cell lineage, compared to that induced by individual pTFs (Kaneto et al, (2005) Diabetes 54: 1009-1022; Tang et al, (2006) Lab Invest. 86: 829-841; Song et al, (2007) Biochem Biophys Res Commun. 354: 334-339; Wang et al, (2007) Mol Ther 15: 255-263; Gefen-Halevi et al, (2010) ibid), as well as along other lineages. In order to analyze this notion in the experimental system of primary adult human liver cells described herein, the individual and joint contribution of three major pTFs on liver to pancreas transdifferentiation were investigated. PDX-1, Pax4 and MafA, which mediate different stages in pancreas organogenesis, were ectopically co-expressed in primary cultures of adult human liver cells using recombinant adenoviruses. Cultured adult human liver cells were infected with Ad-CMV-Pdx-1 (1000 MOI), Ad-CMV-Pax-4 (100 MOI) and Ad-CMV-MafA (10 MOI) alone or in concert or with control virus (Ad-CMV-β-gal, 1000 MOI), and pancreatic differentiation markers were examined six days later. The multiplicity of infection (MOI) of each factor was titrated to result in maximal reprogramming efficiency associated by minimal adverse effects on infected cell viability. PDX-1 was expressed in 70% of the cells in culture, and the joint co-expression of all 3 pTFs was evident in 46.8% of the PDX-1 positive cells (FIG. 2A). Very few cells stained positive for only Pax-4 or for MafA. Cells that stained positive for all three pTFs are indicated by the arrows (FIG. 2A, right panel). In FIG. 2B, liver cells were co-infected with the combined pTFs and with Ad-RIP-LUC (200 moi), and Luciferase activity of the insulin promoter was measured.

The combined expression of the three pTFs resulted in a substantial increase in insulin promoter activation (FIG. 2B), a three-fold increase in the number of (pro)insulin producing cells (FIG. 2C) and 30-60% increase in glucose regulated (pro)insulin secretion (FIG. 2D), compared to that induced by each of the pTFs alone. Taken together, these results suggest that the combination of the 3 pTFs increase transdifferentiation efficiency and also indicate that each of the factors is limited in its capacity or is insufficient to individually promote maximal transdifferentiation (Kaneto et al, (2005) ibid; Tang et al, (2006) ibid; Zhou et al, (2008) Nature 455: 627-632).

Example 4: Maturation and Segregation into the Different Hormones Producing Cells of Transdifferentiated Cells is Temporally Controlled in an Hierarchical Manner In this example, the impact of temporally controlling the ectopic pTFs expression was investigated to determine whether increased transdifferentiation efficiency by combined ectopic expression of the three pTFs is also temporally controlled as suggested above (FIGS. 2A-2D). In support of temporal control having a role in pancreas transdifferentiation, the three pTFs Pdx-1, Pax4, and MafA display distinct temporal expression and function during pancreas organogenesis.

The three pTFs PDX-1, Pax4, and MafA were introduced sequentially or in concert to primary cultures of adult human liver cells using recombinant adenoviruses. Adenovirus-mediated ectopic gene expression peaks 17 hours post infection (Varda-Bloom et al, (2001) Gene Ther 8: 819-827). Therefore, the pTFs were sequentially administered during three consecutive days (see Viral infection in Example 1), allowing the manifestation of their individual effects. Cells were infected according to the schedule as displayed in Table 1.

TABLE 1

| Treatment order | Day 1 | Day 2 | Day 3 | Day 4 | Day 5 | Day 6 |
|---|---|---|---|---|---|---|
| A | Ad-β-gal (control) | | | | | Harvest |
| B | Ad-Pdx-1 + Ad-Pax4 + Ad-MafA | | | | | Harvest |
| C | Ad-Pdx-1 | Ad-Pax4 | Ad-MafA | | | Harvest |
| D | Ad-MafA | Ad-Pax4 | Ad-Pdx-1 | | | Harvest |
| E | Ad-Pdx1 | Ad-MafA | Ad-Pax4 | | | Harvest |

Cells were sequentially infected with one pTF adenoviral construct per day over three days in three different sequences: a direct hierarchical order (treatment C=Pdx-1→Pax4→MafA), in an opposite order (treatment D=MafA→Pax4→Pdx-1), and in a random order (treatment E=Pdx-1→MafA→Pax4). The effect of the sequential pTFs administration on transdifferentiation efficiency and on the β-cell-like maturation was compared to that of the concerted or simultaneous administration of all three pTFs on the first day (treatment B=Pdx-1+Pax4+MafA) and to similar MOI of control virus (treatment A=β-gal) (Table 1 and FIG. 3A). Specifically, cultured adult human liver cells were infected with Ad-CMV-Pdx-1 (1000 MOI), Ad-CMV-Pax-4 (100 MOI) and Ad-CMV-MafA (10 MOI) together or in a sequential manner as summarized in FIG. 3A and Table 1 (treatments B-E) or with control virus (Ad-CMV-β-gal, 1000 moi, treatment A), and analyzed for their pancreatic differentiation six days later.

Figure 4A:
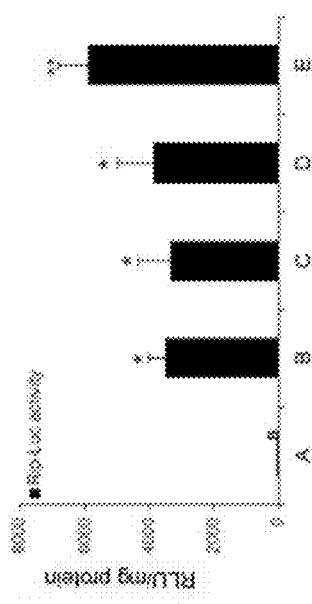
FIGS. 4A-4C show three graphs demonstrating transdifferentiation efficiency, indicating hierarchical sequential order of infection (treatment C) is most efficient.
Figure 4C:
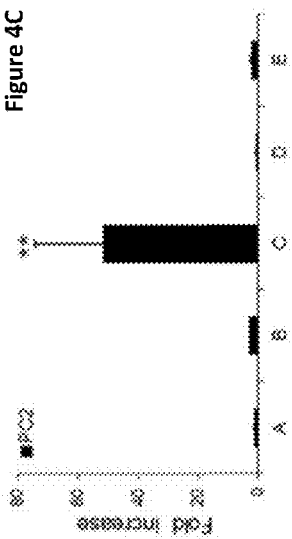
Figure 4B:
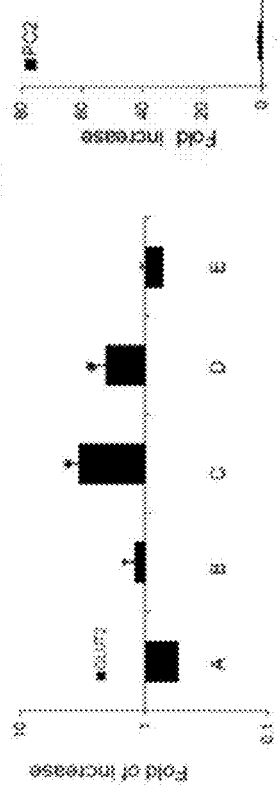

Insulin promoter activity (FIG. 4A), the percent of insulin producing cells (FIG. 3B) and glucose-regulated (pro)insulin secretion (FIG. 3C) were unaffected by the order of the sequentially administered pTFs. Interestingly, the sequential pTF administration in the random order (treatment E=Pdx-1→MafA→Pax4) resulted in increased insulin promoter activity but was associated with loss of glucose regulation of insulin secretion and decreased glucose transporter 2 (GLUT-2) expression (FIGS. 3B, 3C and 4B). Loss of glucose sensing ability upon changing the order of Pax4 and MafA administration suggests a potential effect of the sequence of expressed pTFs on β-cell-like maturation but not on the efficiency of the transdifferentiation process.

Example 5: Hierarchical Administration of Pdx-1, Pax4, and Mafa Promotes the Maturation of Transdifferentiated Cells to β-Like Cells The previous results encouraged further investigation to determine to what extent and under which conditions increased transdifferentiation efficiency is associated with enhanced maturation along the β-cell lineage. The hallmark characteristics of mature β-cells are the capacity to process the proinsulin and secrete it in a glucose-regulated manner (Eberhard et al, (2009) Curr Opin Genet Dev 19: 469-475; Borowiak, (2010) Rev Diabet Stud 7: 93-104). To analyze whether the temporal changes in pTF expression distinctly affect transdifferentiated cell maturation along the β-cell lineage, the effect of the distinct treatments A-E (Table 1 and FIG. 3A) on proinsulin processing and glucose-regulated c-peptide secretion was analyzed.

Figure 5B:
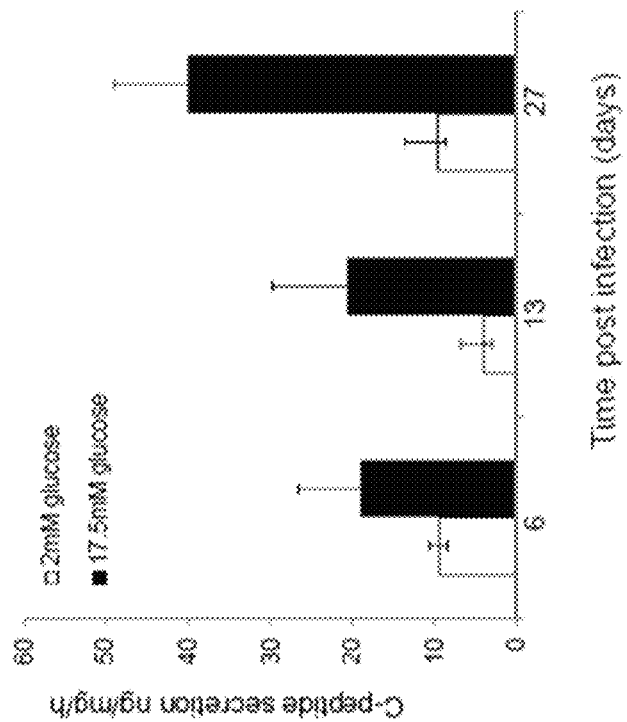
FIGS. 5A-5B show two graphs demonstrating C-peptide secretion after hierarchical sequential order of infection (treatment C).
Figure 5A:
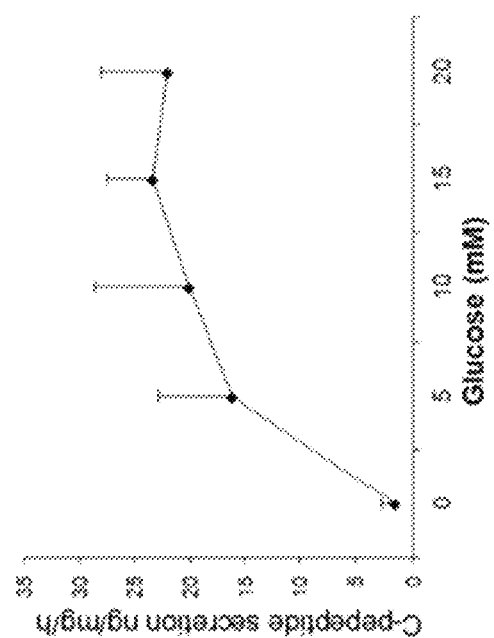

Indeed, only the direct hierarchical administration (treatment C) of the pTFs resulted in pronounced production of processed insulin and its glucose-regulated secretion that displayed physiological glucose dose response characteristics (FIGS. 3C and 5A). The newly acquired phenotype and function were stable, as demonstrated by the ability to secrete c-peptide in a glucose-regulated manner for up to four weeks in vitro (FIGS. 5A and 5B).

The increased prohormone processing only upon the direct hierarchical pTFs administration (treatment C) was associated with pronounced increase in PCSK2 and GLUT2 gene expression, which possess roles in prohormone processing and glucose sensing abilities, respectively (FIGS. 3A-3E and 4A-4C). These data suggest an obligatory role for the sequential and direct hierarchical expression of pTFs in promoting the maturation and function of the transdifferentiated liver cells along the β-cell lineage. Both concerted (treatment B) and sequential TF administration in an indirect hierarchical mode (treatment D and E), failed to generate transdifferentiated cells that display mature β-cell-like characteristics.

To provide a mechanistic explanation for the changes in the β-cell-like state of maturation the repertoire of the endogenously activated pTFs under the distinct temporal treatments (B-E) was analyzed. All the treatments (B-E) resulted in increased expression of numerous endogenous pTFs (FIG. 3E), such as NEUROG3, NEUROD1, NKX6.1 and NKX2.2. However, the most robust difference between the "mature" (treatment C) and "immature" phenotypes (treatments B, E and D) was exhibited at the levels of the endogenous Isl1 gene expression. Thus, the most enhanced maturation along the β-cell lineage induced by direct hierarchical pTFs administration (treatment C) correlates with a dramatic decrease in endogenous Isl1 expression (FIG. 3E, arrow). Taken together these data suggest that the maturation of transdifferentiated cells to β cells may be affected by the relative and temporal expression levels of specific pTFs.

Figure 8G:
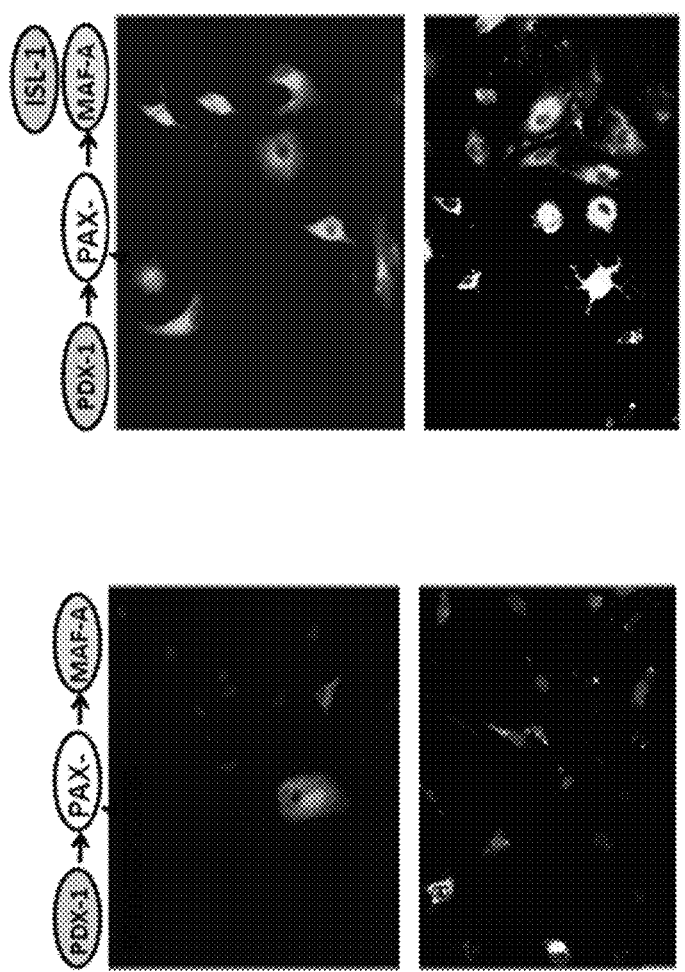

Example 6: Hierarchical Administration of Pdx-1, Pax4, and Mafa Promotes the Segregation of Transdifferentiated Cells Between β-Like and δ-Like Cells Exclusion of MafA from treatment C (Table 1) induced both Isl-1 (FIG. 6D) and somatostatin gene expression (FIG. 8D). To analyze whether Isl-1 increased expression upon MafA exclusion indeed causes increased Somatostatin gene expression, Ad-CMV-Isl-1 was added together with MafA on the $3^{rd}$ day (treatment C, in Table 1). Indeed, Isl-1 increased somatostatin gene expression (FIG. 6E). Ectopic Isl-1 expression (C+Isl-1) caused also increased Somatostatin protein production (FIG. 6F) and its co-production in insulin producing cells (FIG. 9, lower panel), suggesting that high MafA expression associated by low Isl-1 expression is crucial for segregating between insulin and somatostatin producing cells.

Example 7: Analysis of the Individual Contribution of Pdx-1, Pax4, and Mafa to Liver to Pancreas Transdifferentiation The sequential characteristics of the transdifferentiation process were identified by temporal gain of function studies. Further analysis of the separate contribution of each of the transcription factors, Pdx-1, Pax4 and MafA, to the hierarchical developmental process was performed by a relative and temporal "reduced function" approach. Adult human liver cells were treated by the direct temporal and sequential reprogramming protocol (treatment C), from which one of the ectopic pTFs was omitted. The omitted pTF was replaced by a control adenovirus carrying β-gal expression at a similar multiplicity of infection. Specifically, adult human liver cells were treated by the direct "hierarchical" sequential infection order (treatment C, FIG. 3A and Table 1). One single transcription factor (pTF) was omitted at a time and replaced by identical moi of Ad-CMV-β-gal. Pdx-1 omission is indicated as (C-Pdx-1), Pax4 omission is indicated as (C-Pax4), and MafA omission is indicated as (C-MafA).

The functional consequences of separately omitting each of the pTFs' expression were analyzed at the molecular and functional levels (FIGS. 6A-6D). Separate Pdx-1 and MafA omission (C-Pdx-1 and C-MafA, respectively) resulted in decreased insulin promoter activation (FIG. 6A), ablated glucose response of processed insulin secretion (FIG. 6B) and decreased GLUT2 and GK expression (FIG. 6C). Exclusion of MafA associated also with decreased expression of the prohormone convertase, PCSK2 (FIG. 6C). On the other hand, exclusion of Pax4 (C-Pax4) did not significantly affect insulin promoter activation, nor did it affect glucose-regulated C-peptide secretion. Pax-4 omission was associated with decreased GLUT2 and PCSK2 expression (FIG. 6C), possibly suggesting that the expression of GK is sufficient for obtaining glucose control ability of the hormone secretion.

Analysis of the consequences of the temporal and separate pTF exclusion on the repertoire of the endogenously activated pTF expression was performed to explain these developmental alterations. Pdx-1 and Pax4 exclusion caused a marked decline in the expression of most other pTFs (including NeuroG3, NKX2.2, NKX6.2, and Pax6), suggesting that their potential contribution to increasing transdifferentiation efficiency is related to their capacity to activate endogenous pancreatic TFs (FIG. 6D). On the other hand, exclusion of MafA did not contribute to further activation of endogenous pTF expression, possibly reflecting its late and restricted expression only in pancreatic β-cells. On the contrary, MafA contribution to increased insulin promoter activity, prohormone processing and its glucose-regulated secretion was associated only with decreased Isl-1 expression (FIG. 6D). These data may suggest that MafA is not involved in further promoting the efficiency of endogenous pTFs expression and liver to pancreas transdifferentiation, but rather in promoting transdifferentiated cell maturation.

Example 8: Isl-1 Prevents Maturation of Transdifferentiated Cells to β Cell Lineage The effect of MafA on β-cell-like maturation may in part be associated with its capacity to repress Isl1 expression. To test this hypothesis, ectopic Isl1 was introduced by adenoviral infection (Ad-Isl1) in transdifferentiated cells. Briefly, adult human liver cells were treated by the direct "hierarchical" sequential infection order (treatment C) and supplemented by Ad-Isl1 (1 or 100 MOI) at the $3^{rd}$ day (C+Isl1).

Figure 7A:
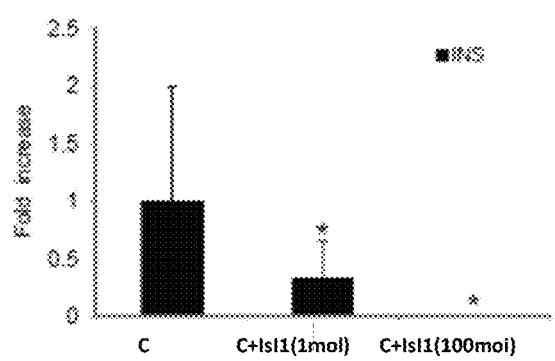
FIGS. 7A-7C shows three graphs showing the effects of Isl1 expression on β-cell maturation of transdifferentiated liver cells after infection by "hierarchical" sequential order (treatment C).
Figure 7B:
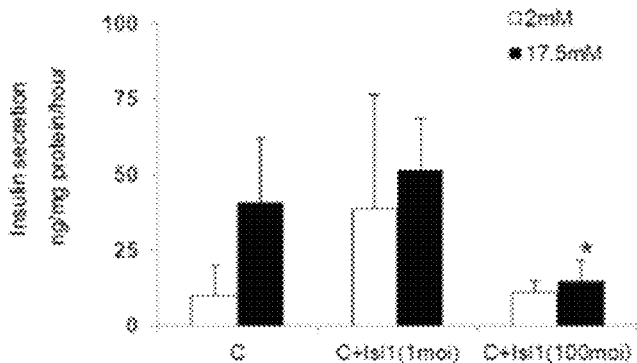
Figure 7C:
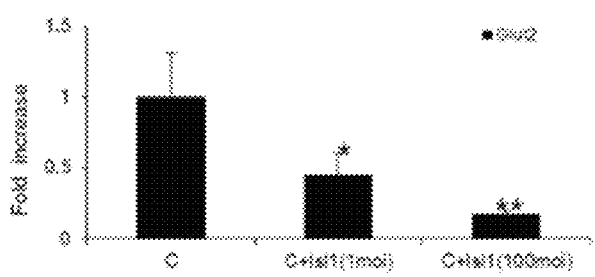

As indicated above, the sequential administration of the three pTFs in a direct hierarchical manner (treatment C) resulted in both increased transdifferentiation efficiency and the maturation of the newly generated cells along the β-cell lineage. Isl1 was jointly administered with MafA on the third day (C+Isl1). Indeed, Isl1 overexpression on the third day, under the control of a heterologous promoter, resulted in substantial decrease of insulin gene expression and ablation of glucose regulated (pro)insulin secretion (FIGS. 7A-7C). The loss of glucose-sensing ability was associated with diminished GLUT2 expression (FIG. 7C). These results suggest that deregulated Isl1 expression at the final stages of the transdifferentiation protocol potentially hampers the maturation along the β cell lineage, and may account in part for the ablated maturation under low MafA expression.

Taken together, these data suggest a crucial obligatory role for direct hierarchical expression of pTFs in promoting transdifferentiated liver cell maturation along the β cell lineage. Moreover, the sequential developmental process is associated with both activation and repression of pTFs that may promote or hamper transdifferentiated cell maturation along the pancreatic β cell lineage.

Example 9: Pdx-1, Pax4 and Mafa Hierarchical Administration Induces Glucagon and Somatostatin Expression Transdifferentiation along the endocrine pancreatic lineage results in the activation of expression of numerous pancreatic hormones. The extent with which these hormone expression levels are affected by the temporal manipulation of the pTFs was also investigated. Gene expression of pancreatic hormones glucagon (GCG) (FIGS. 8A and 8B), somatostatin (SST) (FIGS. 8A, 8D, and 8E) or cells specific transcription factors (FIG. 8C) were determined by quantitative real-time PCR analysis after the indicated treatments.

The transcription of both glucagon (GCG) and somatostatin (SST) genes was induced by each of the individually expressed pTFs, mainly by Pdx-1 and MafA and to a lower extent by Pax4 (FIG. 8A). A further increase in glucagon gene transcription occurred only upon the direct hierarchical administration of pTFs (FIG. 4A, see treatment C). Pdx-1 and MafA exerted their effects on glucagon expression in a process associated with the activation of the α-cell specific transcription factors ARX and BRAIN4 or ARX alone, respectively (FIG. 8C). Somatostatin gene expression that remained unaffected by most treatments (FIGS. 8A and 8D), was increased when the temporal protocol was concluded by ectopic Pax4 expression (E=Pdx-1→MafA→Pax4). This sequential protocol also exhibited a deteriorative effect on glucose-regulated (pro)insulin secretion and was associated by increased Isl1 endogenous expression (FIGS. 3C and 3E). The ablated maturation along the β cell lineage was associated with increased somatostatin gene expression and an increased number of somatostatin positive cells (FIG. 8F). Many of the cells exhibited somatostatin and insulin co-localization (data not shown).

Exclusion of each pTF from the hierarchical administration (treatment C) as discussed in Example 6 was also utilized to further investigate the role of the individual pTFs in glucagon and somatostatin expression (FIGS. 8B and 8D). Pax4 exclusion substantially reduced somatostatin gene expression, suggesting its potential role in inducing the transcription of this gene (FIG. 8D). Interestingly, MafA exclusion at the end of the developmental process also substantially increased somatostatin gene expression, suggesting a potential inhibitory effect of MafA on somatostatin gene expression. This effect could be also attributed to MafA's capacity to repress Isl1 expression. To address this hypothesis, the effect of ectopic Isl1 on somatostatin gene expression was analyzed. Indeed, Ad-Isl1 administration on the third day together with MafA (C+Isl1) increased somatostatin gene expression (FIG. 8E), while decreasing insulin gene expression, hormone production and secretion (FIGS. 8A, 8B and FIG. 7A-7C). Under these experimental conditions, 40% of the insulin producing cells stained positive for somatostatin with very few cells expressing somatostatin alone.

These results suggest that part of the maturation of transdifferentiated cells to β-cells is attributed to MafA expression at the late stages of the transdifferentiation process. At this stage, MafA restricts somatostatin expression in a process associated with its capacity to inhibit Isl1 expression.

Figure 9:
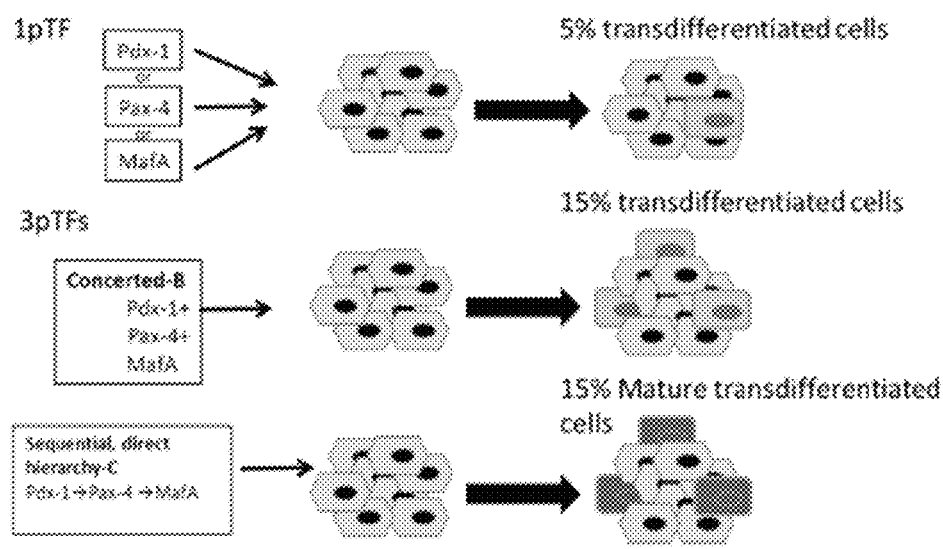
FIG. 9 shows a schematic representation of the proposed mechanism of pancreatic transcription factor-induced transdifferentiation from liver to pancreas. The concerted expression of the three pTFs results in increased number of transdifferentiated liver cells compared to each of the factor's individual effect (Treatment B). The sequential administration of transcription factors in a direct hierarchical manner results in increased maturation of the Transdifferentiated cells along the beta-like-pancreatic lineage (Treatment C).

FIG. 9 shows the proposed mechanism of pancreatic transcription factor induced liver to pancreas transdifferentiation. Each of the pTFs is capable of activating a modest β-cell-like phenotype, in a restricted number of human liver cells. The concerted expression of the pTFs markedly increases liver to endocrine pancreas transdifferentiation. However the newly generated cells are immature and coexpress both insulin and somatostatin. Only sequential administration of the same factors in a direct hierarchical manner both increases transdifferentiation efficiency and also the transdifferentiated cell maturation along the β-cell lineage.

Example 10: Identification of Cell Populations with Transdifferentiation Capacity In Vivo Cell populations with transdifferentiation capacity were identified in vivo in mice. Ectopic expression of the Pdx-1 gene was achieved in mice livers. Despite the uniform expression of the ectopic Pdx-1 gene in about 40-50% of the cells of the liver (FIG. 10A) (Ferber et al., (2000) Nat Med 6: 568-572, and Ber et al., (2003) ibid) insulin-producing cells (IPCs) in Pdx-1-treated mice in vivo were primarily located close to central veins (FIG. 10B), which is characterized by active Wnt signaling and the expression of glutamine synthetase (GS) (FIG. 1C). The co-localization of GS expression and insulin activation by Pdx-1 also indicated that those cells that can activate the GSRE have a predisposition for increased transdifferentiation capacity. Therefore, cell populations predisposed for transdifferentiation can also be identified by GSRE activation or active Wnt-signaling pathway.

Example 11: Using Adenoviruses to Identify Human Liver Cells Predisposed for Transdifferentiation This example demonstrates the use of recombinant adenoviruses to identify human liver cells that are predisposed for transdifferentiation. Human liver cells in culture are heterogeneous with regard to the activation of the intracellular Wnt signaling pathway and expression of GS. As GS is uniquely expressed in pericentral liver cells, therefore the capacity to activate GSRE (GS Regulatory Element) can be used as a selective parameter of isolation of relevant cells.

In addition as the GSRE contains also a STAT3 binding element, the predisposition of the cells to transdifferentiation could be mediated by this element. The STAT3 pathway could also be involved in endowing the cells with reprogramming or transdifferentiation predisposition (FIGS. 10A-10D, 11, 14A-14E and 19).

Figure 11:
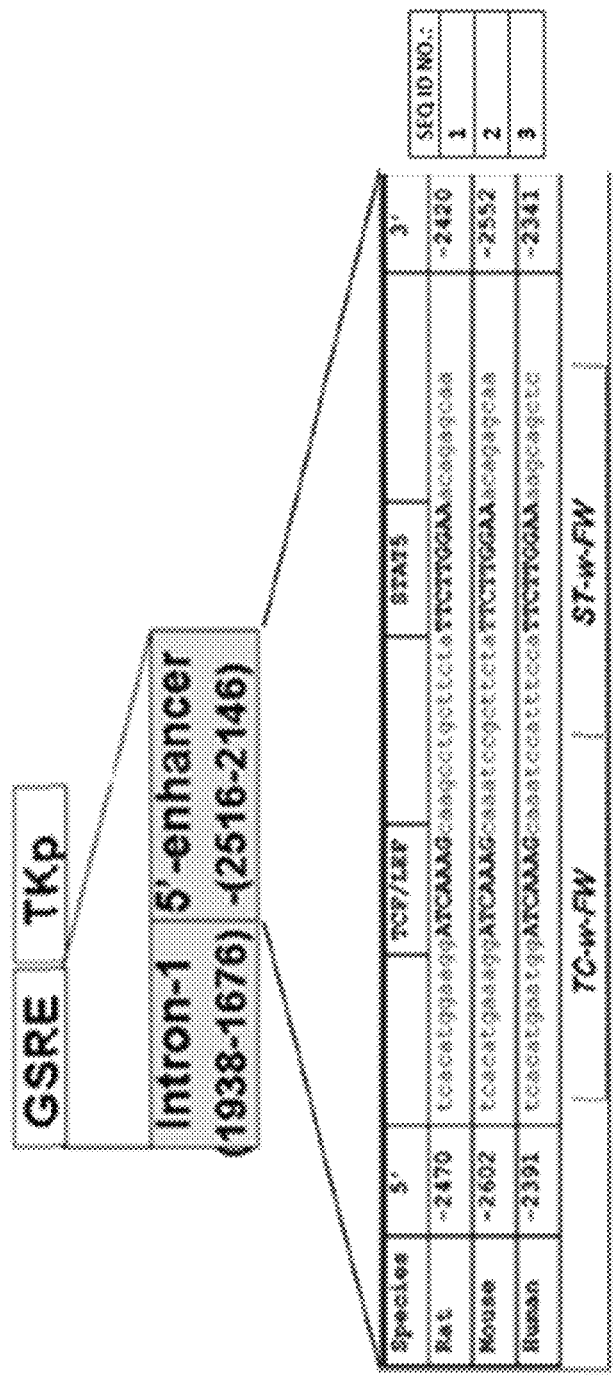
FIG. 11 shows glutamine synthetase response element (GSRE) contains Wnt signaling responding element-TCF-LEF binding site. A schematic presentation of GSRE indicating the presence of TCF-LEF and STAT 5 binding sites.

Example 12: GSRE Repetitively Targets 13-15% of the Human Liver Cells in Culture GSRE includes TCF/LEF and STAT5 binding elements (FIG. 11). Two recombinant adenoviruses that carry the expression of eGFP gene or Pdx-1 genes under the control of GSRE (FIG. 11) operatively linked to a minimal TK promoter have been generated. These adenoviruses drove the expression of either Pdx-1 (FIG. 12A) or eGFP (FIG. 12B). Both proteins were repetitively expressed in about 13-15% of the human liver cells in culture suggesting the targeting of a specific population of liver cells.

Example 13: GSRE Driven PDX-1 is More Efficient than CMV Driven Pdx-1 in Activating Insulin Production in Liver Cells Despite the repetitive expression of GSRE driven PDX-1 only about 13±2% of the cells in culture showed transdifferentiation capacity similar or higher than that induced by Ad-CMV-Pdx-1, which drives Pdx-1 expression in 60-80% of the cells in culture (FIGS. 13A-13C). GSRE-activating cells could account for most of the transdifferentiation capacity of the entire adult human liver cells in culture. Insulin production occurred in 25% of Pdx-1 positive cells upon Ad-GSRE-Pdx-1 treatment compared to 1% of the Ad-CMV-Pdx-1 treated cells.

Example 14: Using Lentiviruses to Permanently Label the GSRE+ Cells by EGFP

Permanent lineage tracing was performed using Lentivirus constructs. In vitro lineage tracing for GSRE activity was performed by a modified dual lentivirus system recently used to trace KRT5 in keratinocytes or albumin expression in liver cells. This lentivirus system (a collaboration with Prof. P. Ravassard from Université Pierre et Marie Curie Paris, France; FIG. 12A) includes the CMV-loxP-DsRed2-loxP-eGFP (R/G) reporter and an additional lentiviral vector carrying the expression of Cre recombinase under the control of GSRE and a minimal TK promoter (generously contributed by Prof Gaunitz, Germany, FIG. 3A). Thus, GSRE-activating cells are irreversibly marked by eGFP (eGFP+), while the rest of the doubly infected cells are marked by DsRed2 (DsRed2+). Ten to fourteen percent of the cells became eGFP+ within less than 10 days (FIG. 14B). The cells were separated by a cell sorter (FIGS. 14A-14E) and separately propagated (FIG. 15A). Cultures of eGFP+ (GRE activators) and DsRed2+ cells were generated from 10 different human donors (ages 3-60).

Figures 16A, 16B, 16C:
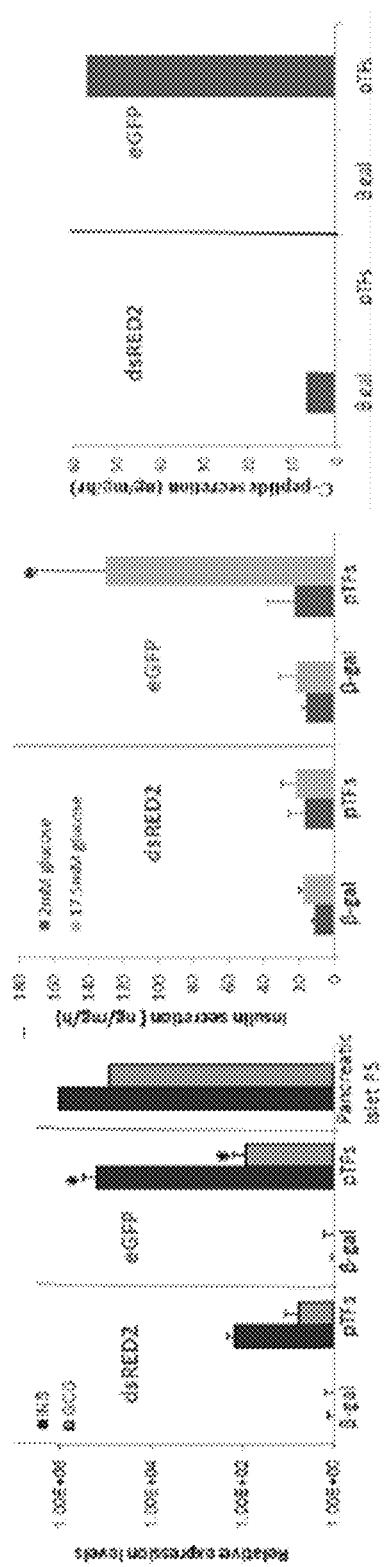
FIGS. 16A-16C shows eGFP+ cells respond more efficiently than DsRed2+ cells to pTFs-induced transdifferentiation. The two groups were similarly treated with soluble factors and pTFs: Ad-Pdx-1+Ad-Pax-4+ad-MafA or a control virus (Ad-β-gal) for 6 days. β-cell-like characteristics and function were compared in the separated groups.

Example 15: EGFP+ Cells Consistently Exhibited Superior Transdifferentiation Capacity Human liver cells separated by lineage tracing according to GSRE activity efficiently propagated (FIG. 15A) and were similarly efficiently infected by recombinant adenoviruses. eGFP+ cells consistently exhibited superior transdifferentiation capacity (FIG. 16A-16C) manifested by insulin and glucagon gene expression that was comparable to that of human pancreatic islets in culture (FIG. 16A), glucose regulated insulin secretion (FIG. 16B) and glucose regulated C-peptide secretion (FIG. 16C). These capacities were consistent and did not diminished upon extensive cell proliferation, (FIG. 17).

Figure 18:
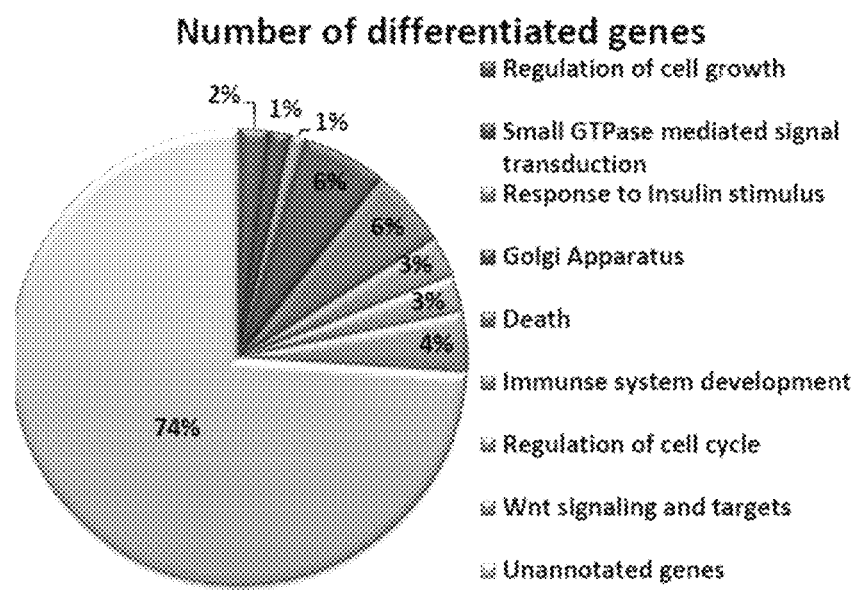
FIG. 18 shows differential gene expression profiles of eGFP+ and DsRed2+ cells performed by microarray analyses and analyzed according to DAVID Bioinformatics Resources 6.7. Four Percent of the differential genes belong to the Wnt signaling pathway.

Example 16: Characterization of Cells with Predisposition for Transdifferentiation To identify the factors that could potentially affect the distinct transdifferentiation efficiencies of the human liver cells, the global gene expression profile of the two separated populations was compared using microarray chip analyses. Human liver cell cultures derived from 3 different donors and separated into eGFP+ and DsRed2+ cells were propagated for 4 passages. The extracted RNA was converted into cDNA and subjected to microarray chip analysis using the General Human Array (GeneChip Human Genome U133A 2.0 Array, Affymetrix). While most of the genes were expressed at comparable levels in the separated groups, the expression of about 800 probes was significantly different (FIG. 18). According to microarray chip analyses, about 100 genes coding for membrane proteins are differentially expressed between the transdifferentiation-prone (eGFP+) and non-responding (DsRed2+) cells. Several of these markers are presented in Table 2A and 2B.

TABLE 2A

Membrane antigens that are differentially expressed in eGFP+ and DsRed2+ cells.

| Antigene | High expression | Fold (Log 2) | p-value | commercial antibody |
|---|---|---|---|---|
| ABCB1 | DsRed2 | −6.363 | 1.52E−02 | BD Biosciences (#557002) |
| ITGA4 | DsRed2 | −1.979 | 2.69E−02 | R&D system (FAB1354G) |
| ABCB4 | DsRed2 | −4.42 | 4.62E−02 | Abcam (ab24108) |
| PRNP | DsRed2 | −1.35 | 4.20E−02 | eBioscience (12-9230-73) |
| HOMER1 | eGFP | 1.41 | 3.25E−04 | Biorbyt (orb37754) |
| LAMP3 | eGFP | 1.285 | 1.81E−02 | BD Biosciences (#558126) |
| BMPR2 | eGFP | 1.236 | 3.50E−02 | R&D system (AF811) |

TABLE 2B

Cell-surface coding transcripts differentially expressed in eGFP+ vs. DsRed2+ cells

| Gene symbol | Gene name | Fold change EGFP+/DsRed2+ cells | ΔCt (gene-actin) eGFP+ cells |
|---|---|---|---|
| ITGA6 | INTEGRIN ALPHA-6 | 2.82759 | 8.6 |
| DCBLD2 | DISCOIDIN, CUB AND LCCL DOMAIN-CONTAINING PROTEIN 2 | 2.4747 | 12.3 |
| THBS1 | THROMBOSPONDIN-1 | 2.29441 | 1.5 |
| VAMP4 | VESICLE-ASSOCIATED MEMBRANE PROTEIN 4 | 1.97484 | 18.3 |

Figure 47:
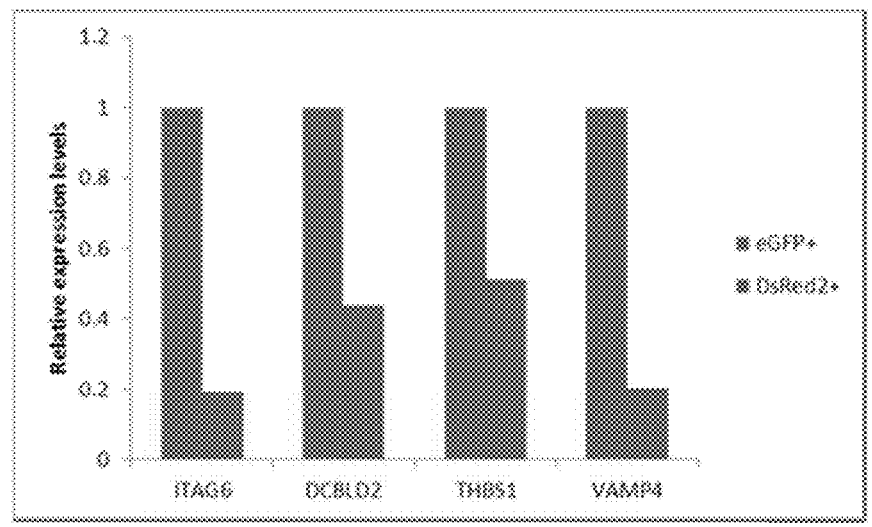
FIG. 47 presents a bar graph of the relative expression levels of cell-surface molecules in eGFP+ and DsRed2+ cells, listed in Table 2B of Example 16.

FIG. 47 shows the relative expression of the cells surface molecules presented in Table 2B. Expression levels of specified molecules were tested by Real Time PCR and normalized to beta-actin expression. Microarray data suggested numerous membrane proteins that are differential expression between the eGFP+ and the DsRed2+ cells (Fold=eGFP+ differential expression compared to the DsRed2+ (log 2). All the presented antigens have commercially available antibodies.

Example 17: Wnt Signaling is Active in Cells Predisposed for Transdifferentiation Liver zonation has been suggested to be controlled by a gradient of activated β-catenin levels; while most cells in the liver contain very low β-catenin activity, the pericentral liver cells express high β-catenin activity associated with active Wnt signaling. Since Wnt signaling is obligatory for competent β cell activity, the pTFs-induced pancreatic lineage activation in the liver is restricted to cells that a priori display active Wnt signaling.

GSRE utilized a TCF regulatory element isolated from the 5' enhancer of GS. If Pdx-1-induced liver to pancreas transdifferentiation is mediated in part by the intracellular Wnt signaling pathway, factors that modulate the Wnt signaling pathway can also affect transdifferentiation efficiency (FIG. 19).

Figure 19:
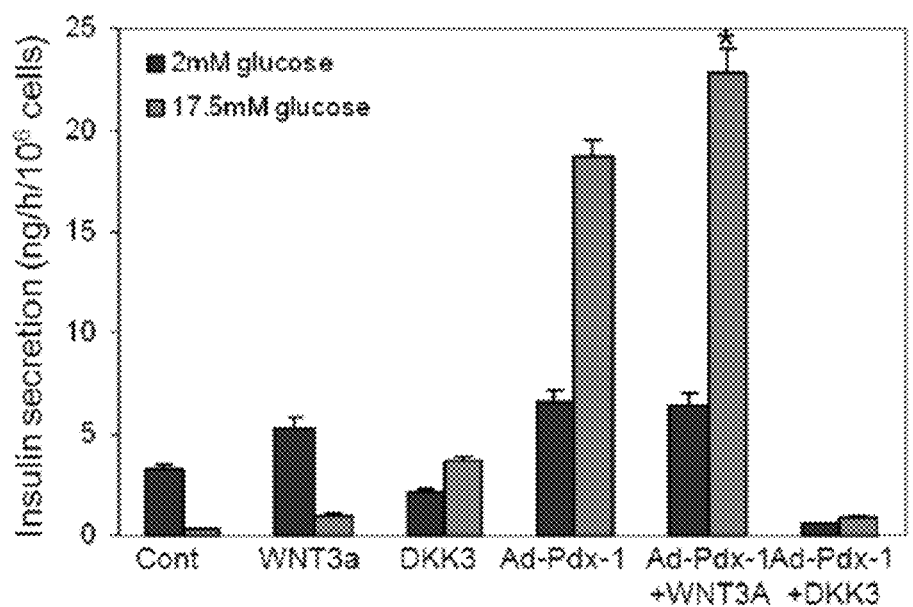
FIG. 19 shows that active Wnt signaling promotes liver to pancreas transdifferentiation. Adult human liver cells were treated with Ad-CMV-Pdx-1 and soluble factors, as previously reported, supplemented with Wnt3A (50 ng/ml R&D) or DKK3 (3 μg/ml R&D). After 5 days, insulin secretion was analyzed by static incubations at low followed by high glucose concentrations (2 mM and 17.5 mM glucose in KRB, respectively). Insulin secretion is measured using the human insulin radioimmunoassay kit (DPC; n≥8 from 3 different experiments) and compared to untreated cells (Cont). *p<0.01 compared to Ad-CMV-Pdx-1 alone, using Student's t-test analysis.
Figure 20:
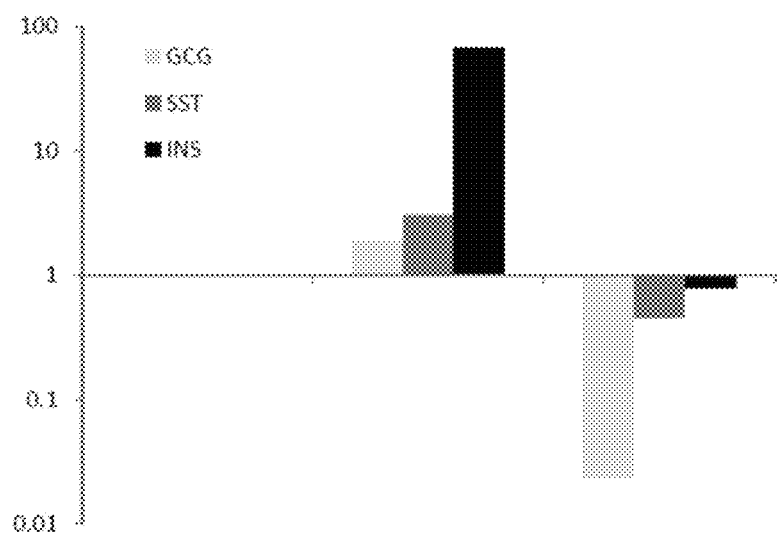
FIG. 20 shows that blocking the Wnt signaling pathway abolishes the transdifferentiation of eGFP+ cells. eGFP cells were Ad-CMV-Pdx-1 or a control virus (Ad-CMV-β-gal) for 5 days supplemented with DKK3 (Dickkopf-related protein 3) (0.5 μg/ml R&D). Pancreatic hormones gene expression was studied by Quantitative real-time RT-PCR compared to the control-treated cells.

This data in adult human liver cells suggest that increasing concentrations of Wnt3a increased Pdx-1-induced glucose-regulated insulin secretion, while DKK3 (an inhibitor of the Wnt signaling pathway) completely abolished the effect of Pdx-1 on the process (FIG. 19). DKK3 also totally abolished the transdifferentiation capacity of the eGFP cells isolated according to their ability to activate GSRE (FIG. 20).

Figures 21A, 21B, 21C:
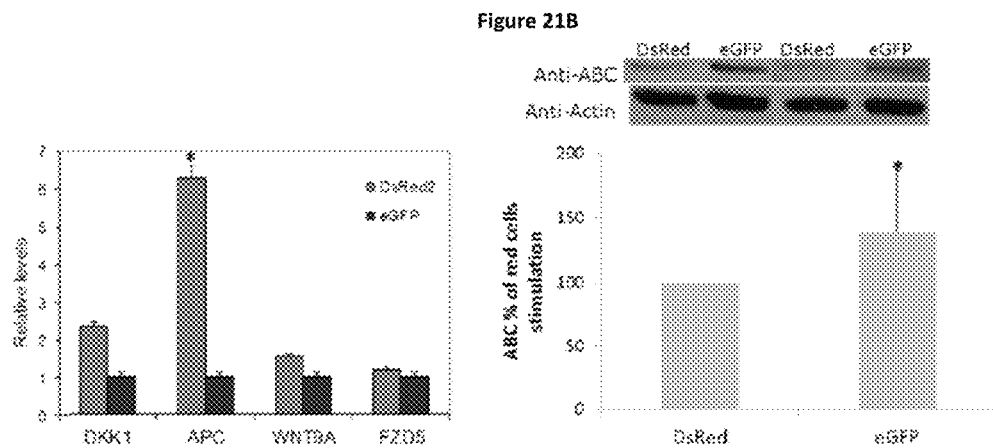
FIGS. 21A-21C show eGFP+ cells express lower levels of APC and higher levels of active β-catenin than DsRed2+ cells.
Figure 22:
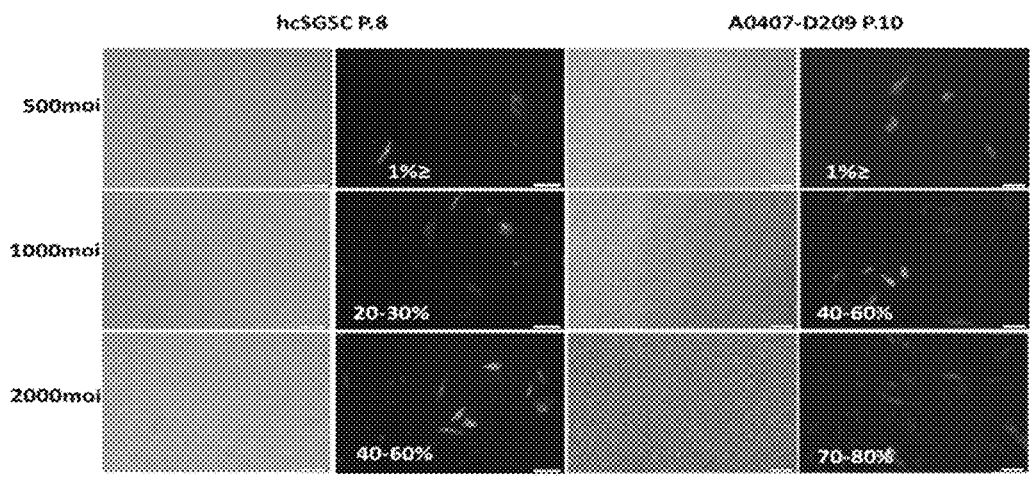
FIG. 22 present micrographs showing mesenchymal stem cells (MSC) are susceptible to adenovirus infection. MSC were infected by increasing moi of Ad-GFP. Five days later, cells were visualized by fluorescent microscopy (magnification ×4) Representative phase contrast morphology (left panel), and green fluorescence (left panel) of MSC infected by Ad-CMV-GFP. Infection of MSC cells with 1000 MOI of Ad-GFP resulted in about 20-60% positive cells (dependent on cell-lines), when liver cells usually present 70-80% positive cells.
Figure 23:
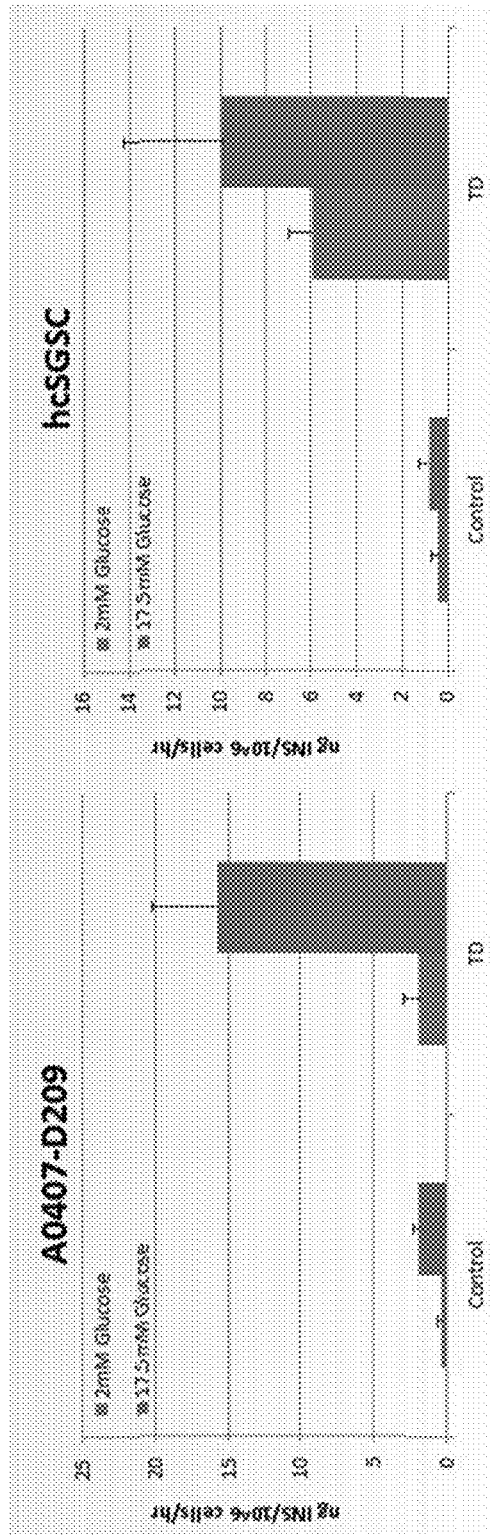
FIG. 23 shows a bar graph showing that MSC secreted insulin in a glucose-regulated manner. Cells were examined for their ability to undergo transdifferentiation. Transdifferentiation was induced on MSC by infecting cells with PDX1, NeuroD1 and MafA. On the sixth day of the experiment, cells underwent secretion experiment and RIA for Insulin detection. Insulin secretion in a glucose-regulated manner was measured by incubation for 15 min with 2 mM or 17.5 mM glucose in KRB.
Figures 25C, 25D:
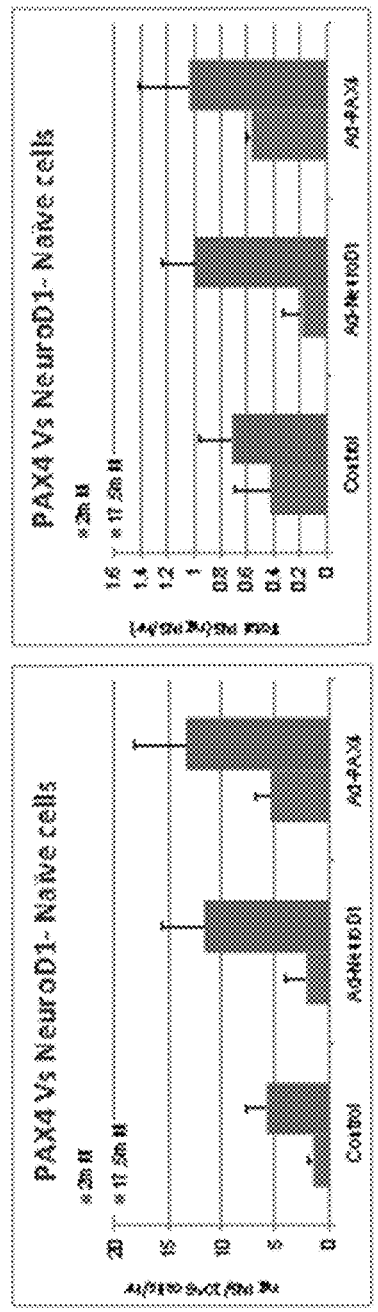

Characterization of Wnt signaling pathway activity in the eGFP+ and DsRed+ cell populations was performed. The APC expression, which participates in θ-catenin destabilization, thus diminishing Wnt signaling, was 700% higher in DsRed2+ cells than in the eGFP+ cells (FIG. 21A, in relative agreement with the zonation displayed in vivo). The eGFP+ population has increased activated θ-catenin levels (40%) compared to the levels analyzed in DsRed2+ cells (FIGS. 21B and 21C). These data demonstrate that Wnt signaling is active in cells that are competent for GSRE activation and have predisposition for transdifferentiation.

Example 18: Comparing the Efficiency of Transdifferentiation Induced by PAX4 and NeuroD1

Aim

The aim of this study was to compare the PAX4 and NeuroD1 adenoviruses (Ad-PAX4 and Ad-NeuroD1) in promoting the transdifferentiation process induced by Ad-PDX-1.

Materials and Methods

The comparison of the transdifferentiation efficiency induced by Ad-PAX4 or Ad-NeuroD1 was performed on three naïve cultures (unsorted primary hepatocyte cells) obtained from human subjects Muhammad, Pedro, and Diego, and four primary hepatocyte cultures following sorting for glutamine synthetase response element (GSRE) activation (GS enriched): Shalosh, Eden, Muhammad and Yam.

Experimental Design

On the first day of the experiment, 300,000 cells were seeded after viral infection on 100 mm Falcon dish according to Table 3. On the third day of the experiment, cells were counted and treated by Ad-MafA and seeded on 3 wells of a 6 wells dish to a final concentration of 100,000 cells/well. On the sixth day of the experiment, cells were analyzed for insulin secretion using a radioimmunoassay. Insulin secretion was measured following incubation of the cells for 15 minutes with either 2 mM glucose (low) or 17.5 mM glucose (high) in KRB.

TABLE 3

Summary of the different combination of adenoviruses used for comparing the role of PAX4 and NeuroD1 in the transdifferentiation process induced by PDX1.

| | Day1 | Day3 |
|---|---|---|
| 1 | Ad-Null 1300 moi | |
| 2 | Ad-PDX1 500 moi + Ad-NeuroD1 250 moi | Ad-MafA 50 moi |
| 3 | Ad-PDX1 500 moi + Ad-PAX4 250 moi | Ad-MafA 50 moi |

Results

The results are summarized in Tables 4 and 5 and FIGS. 24A-24B and 25A-25D.

TABLE 4

Summary of the final calculations of total insulin (INS) secretion per hour (ng INS/hr) comparing the role of PAX4 and NeuroD1 in the transdifferentiation process induced by PDX1.

| | | Total ng/h | | Average ng/h | | SE | |
|---|---|---|---|---|---|---|---|
| | Samples | Low | High | Low | High | SE 2 mM | 17.5 mM |
| Control | Shalosh GS enriched | 0 | 0.380923 | 0.166896 | 0.524835 | 0.101164 | 0.112632 |
| | Eden Green | 0.197364 | 0.758004 | | | | |
| | Muhammad GS enriched | 0 | 0.721483 | | | | |

TABLE 4-continued

Summary of the final calculations of total insulin (INS) secretion per hour (ng INS/hr) comparing the role of PAX4 and NeuroD1 in the transdifferentiation process induced by PDX1.

|  |  | Total ng/h | | Average ng/h | | | SE |
|---|---|---|---|---|---|---|---|
|  | Samples | Low | High | Low | High | SE 2 mM | 17.5 mM |
|  | Yam GS enriched | 0 | 0.39728 | 0.034227 | 0.430182 | 0.032654 | 0.114352 |
|  | Max GS enriched | 0 | 0 | | | | |
|  | Eden GS enriched | 0.008 | 0.3234 | | | | |
|  | Muhammad Naive | 0.245521 | 1.069337 | 0.432233 | 0.714142 | 0.254312 | 0.244889 |
|  | Pedro Naïve | 0.935318 | 0.244501 | | | | |
|  | Diego Naive | 0.115859 | 0.828589 | | | | |
| PDX1 + NeuroD1 | Shalosh GS enriched | 0.102627 | 1.138869 | 0.14397 | 1.601043 | 0.057159 | 0.351225 |
|  | Eden Green | 0 | 1.500592 | | | | |
|  | Muhammad GS enriched | 0.027635 | 1.048397 | | | | |
|  | Yam GS enriched | 0.217733 | 4.162756 | 0.119999 | 1.900602 | 0.060742 | 0.480813 |
|  | Max GS enriched | 0 | 2.177 | | | | |
|  | Eden GS enriched | 0.372 | 1.376 | | | | |
|  | Muhammad Naive | 0 | 1.411349 | 0.191913 | 1.001924 | 0.137961 | 0.23494 |
|  | Pedro Naïve | 0.459557 | 0.996881 | | | | |
|  | Diego Naive | 0.116183 | 0.59754 | | | | |
| PDX1 + PAX4 | Shalosh GS enriched | 0.381611 | 0.491117 | 0.351915 | 1.301016 | 0.087502 | 0.275093 |
|  | Yam GS enriched | 0.056133 | 0.785065 | | | | |
|  | Muhammad GS enriched | 0.302323 | 2.249145 | | | | |
|  | Max GS enriched | 0.057 | 2.744 | 0.223414 | 1.455865 | 0.137343 | 0.393614 |
|  | Eden GS enriched | 0.32 | 1.01 | | | | |
|  | Muhammad Naive | 0.89452 | 1.376825 | 0.566084 | 1.042933 | 0.037142 | 0.370843 |
|  | Pedro Naïve | 0.447356 | 0.4218 | | | | |
|  | Diego Naive | 0.356376 | 1.330176 | | | | |

TABLE 5

Summary of the final calculations of total insulin (INS) secretion per million cells per hour (ng INS/10$^6$ cells/hr) comparing the role of PAX4 and NeuroD1 in the transdifferentiation process induced by PDX1.

|  |  | ng/h/10$^{\char`\^}$6 cells | | Average ng/h/10$^{\char`\^}$6 cells | | SE | |
|---|---|---|---|---|---|---|---|
|  | Samples | 2 mM | 17.5 mM | | | SE 2 mM | 17.5 mM |
| Control | Shalosh GS enriched | 0 | 5.355152 | 0.671145 | 4.501346 | 0.271034 | 0.877392 |
|  | Eden Greeen | 1.265156 | 4.859 | | | | |
|  | Muhammad GS enriched | 0 | 5.900258 | | | | |
|  | Yam GS enriched | 0 | 1.91 | 0.234193 | 3.835735 | 0.207456 | 0.955189 |
|  | Max GS enriched | 0 | 0 | | | | |
|  | Eden GS enriched | 0.14 | 4.99 | | | | |
|  | Muhammad Naive | 2.00425 | 8.190631 | 1.54505 | 5.832567 | 0.305842 | 1.829411 |
|  | Pedro Naïve | 1.665405 | 2.230751 | | | | |
|  | Diego Naive | 0.965494 | 7.07632 | | | | |

TABLE 5-continued

Summary of the final calculations of total insulin (INS) secretion per million cells per hour (ng INS/$10^6$ cells/hr) comparing the role of PAX4 and NeuroD1 in the transdifferentiation process induced by PDX1.

| | | ng/h/10^6 cells | | Average ng/h/10^6 cells | | SE | |
|---|---|---|---|---|---|---|---|
| | Samples | 2 mM | 17.5 mM | | | SE 2 mM | 17.5 mM |
| PDX1 + NeuroD1 | Shalosh GS enriched | 1.345204 | 13.19027 | 2.016969 | 16.19933 | 1.042752 | 2.502689 |
| | Muhammad GS enriched | 0.310173 | 14.16339 | | | | |
| | Eden Green | 0 | 12.82557 | | | | |
| | Yam GS enriched | 1.136 | 21.7188 | 1.926396 | 18.43701 | 1.387931 | 3.003895 |
| | Max GS enriched | 0 | 16.864 | | | | |
| | Eden GS enriched | 8.767 | 31.86 | | | | |
| | Muhammad Naive | 0 | 17.52215 | 2.198114 | 11.72398 | 1.841633 | 3.875939 |
| | Pedro Naïve | 5.856674 | 13.28074 | | | | |
| | Diego Naive | 0.737667 | 4.369039 | | | | |
| PDX1 + PAX4 | Shalosh GS enriched | 5.984453 | 7.723947 | 3.954761 | 14.31825 | 0.917087 | 2.523347 |
| | Yam GS enriched | 0.421 | 5.888 | | | | |
| | Muhammad GS enriched | 2.468333 | 18.063 | | | | |
| | Max GS enriched | 0.52 | 25.753 | 3.050957 | 14.85359 | 1.22808 | 3.634948 |
| | Eden GS enriched | 5.861 | 16.84 | | | | |
| | Muhammad Naive | 8.187757 | 14.31595 | 5.461101 | 13.42601 | 1.410137 | 4.709221 |
| | Pedro Naïve | 4.721848 | 4.860915 | | | | |
| | Diego Naive | 3.473699 | 21.10115 | | | | |

A detailed comparison was made between the two pancreatic transcription factors. The comparison was made on mixed populations of naïve primary hepatocytes and hepatocyte populations enriched by sorting for enhanced GS expression (GS enriched).

FIGS. 24A-24B and 25A-25D present the tabulated data as bar graphs.

Insulin secretion measurements revealed that there is no statistical difference in the transdifferentiation induced using PAX4 or NeuroD1. This conclusion was true for both naïve cells and enriched GS cells. It was not only the averages of the enriched GS populations and naïve cells that showed the same trends, when examining the results of the same culture Muhammad naïve and Muhammad GS enriched, the same results were obtained (demonstrating the ability of the GS enriched population to serve as a model system for the transdifferentiation process).

Previous results showed that GS enriched populations had a clear advantage over the full hepatocyte primary culture with regard to transdifferentiation efficiency. It was therefore, surprising that the GS enriched population and the unsorted population of Muhammad showed similar results (no statistical significance). However, it should be mentioned that there was a difference in the passage number of both populations. The GS enriched population was examined in passage 19 and the naïve population was examined in passage 7. These results should not be addressed as a failure of the GS enriched population to undergo effective transdifferentiation but as the GS enriched population's ability to undergo transdifferentiation in high passages that the naïve cells may not be able to achieve.

There were no significant differences in the cell death of cells incubated with PAX4 compared to cells incubated with NeuroD1. The only difference that was evident was of control group (untreated/Ad-Null) compared to the treated groups (Ad-PAX4/Ad-NeuroD1). This is seen by the same conclusions reached for PAX4 and NeuroD1 whether examining the results for Total Insulin or for ng INS/10^6 cells/hr.

The one difference observed was when calculating the transdifferentiation efficiency (percent of positive transdifferentiation obtained when using the specific adenovirus). For Ad-NeuroD1 the efficiency was 87.5% (7 positive transdifferentiation out of 8 experiments) and for Ad-PAX4 it was 71% (5 positive transdifferentiation out of 7 experiments).

Conclusion

Both Ad-PAX4 and Ad-NeuroD1 support similar transdifferentiation of hepatocytes.

Example 19: Determining the Optimal Protocol for the Transdifferentiation Process Aim The aim of this study was to compare the transdifferentiation efficiency of the full hierarchy (1+1+1 protocol), with the 2+1 protocol, and with simultaneous infection with all three adenoviruses.

The Test System

The different transdifferentiation protocols were examined on three primary cultures of human liver cells, Leon, Muhammad, and Pedro grown in DMEM 1 g/L glucose. After viral infection cells were grown in DMEM 1 g/L glucose media supplemented with 5 nM Exendin-4, 20 ng/ml EGF and 10 mM Nicotinamide.

Experimental Design

The different transdifferentiation (TD) protocols were examined according to the Table 6 below. Briefly, on the first day of the experiment 300,000 cells were seeded after viral infection on 100 mm Falcon dish according to Table 6 below for protocols A (Null), B (2+1) and E (Hierarchy 1+1+1). On the second day of the experiment 100,000 cells were seeded on 6 wells dish for protocol C (3 factors simultaneously) and 70,000 cells were seeded on 6 wells dish for protocol D (3 factors simultaneously). On the third day of the experiment, cells were counted and treated by Ad-MafA (protocols B and E) and seeded on 3 wells of a 6 wells dish to a final concentration of 100,000 cells/well.

TABLE 6

| | Day 1 | Day 2 | Day 3 | Day 6 |
|---|---|---|---|---|
| A | Null (1300 moi) | | | GSIS* |
| B | PDX1 1000 moi + NeuroD1 250 moi | | MafA 50 moi | GSIS |
| C | | PDX1 1000 moi + NeuroD1 250 moi + MafA 50 moi | | GSIS |
| D | | PDX1 1000 moi + NeuroD1 250 moi + MafA 50 moi | | GSIS |
| E | PDX1 (E4) 1000 moi | NeuroD1 250 moi | MafA 50 moi | GSIS |

*GSIS - Glucose stimulated insulin secretion

On the sixth day of the experiment, cells underwent secretion analysis in the presence of 2 mM glucose (low) or 17.5 mM glucose (high) (FIGS. 26A-26C). Insulin secretion was measured following incubation of cells for 15 minutes with 2 mM glucose or 17.5 mM glucose in KRB.

Results and Analysis

The present study sought to determine the optimal protocol for the transdifferentiation process. In the traditional hierarchy protocol (1+1+1), cells are treated sequentially with three transcription factors: PDX1 on day 1, NeuroD1 on day 2 and MafA on day 3. In an effort to develop an efficient and easier protocol, the transdifferentiation efficiency of the traditional protocol, was compared with the 2+1 protocol and simultaneous treatment with all three transcription factors present.

The read out assay for this examination was insulin secretion. According to knowledge in the field, all treatments should have presented similar levels of insulin secretion, as differences in efficiency should be presented only in the maturation of the cells, for example as measured by C-peptide secretion. However, in the present experiments there were unexpected differences in transdifferentiation efficiency as clearly seen by the insulin secretion measurements (FIGS. 26A-26C). The best results were obtained in the 2+1 protocol. These results were statistically significant, as shown in Table 7 below.

TABLE 7 p-value (t-Test) for the comparison of the different transdifferentiation protocols presented in Table 4 above.

| | Hierarchy | 3 factors (70K) | 3 factors (100K) | 2 + 1 |
|---|---|---|---|---|
| 2 + 1 | 0.06691407 | 0.04561124 | 0.017915142 | |
| 3 factors (100K) | 0.223713506 | 0.35910095 | | 0.017915142 |

TABLE 7-continued p-value (t-Test) for the comparison of the different transdifferentiation protocols presented in Table 4 above.

| | Hierarchy | 3 factors (70K) | 3 factors (100K) | 2 + 1 |
|---|---|---|---|---|
| 3 factors (70K) | 0.376772188 | | 0.35910095 | 0.04561124 |
| Hierarchy | | 0.376772188 | 0.223713506 | 0.06691407 |

The p-value of the 2+1 protocol and the hierarchy protocol is significant but relatively high. The simultaneous treatment with all three factors presented the lowest results even though two seeding densities were examined (not significant in comparison to the hierarchy protocol).

Figure 27:
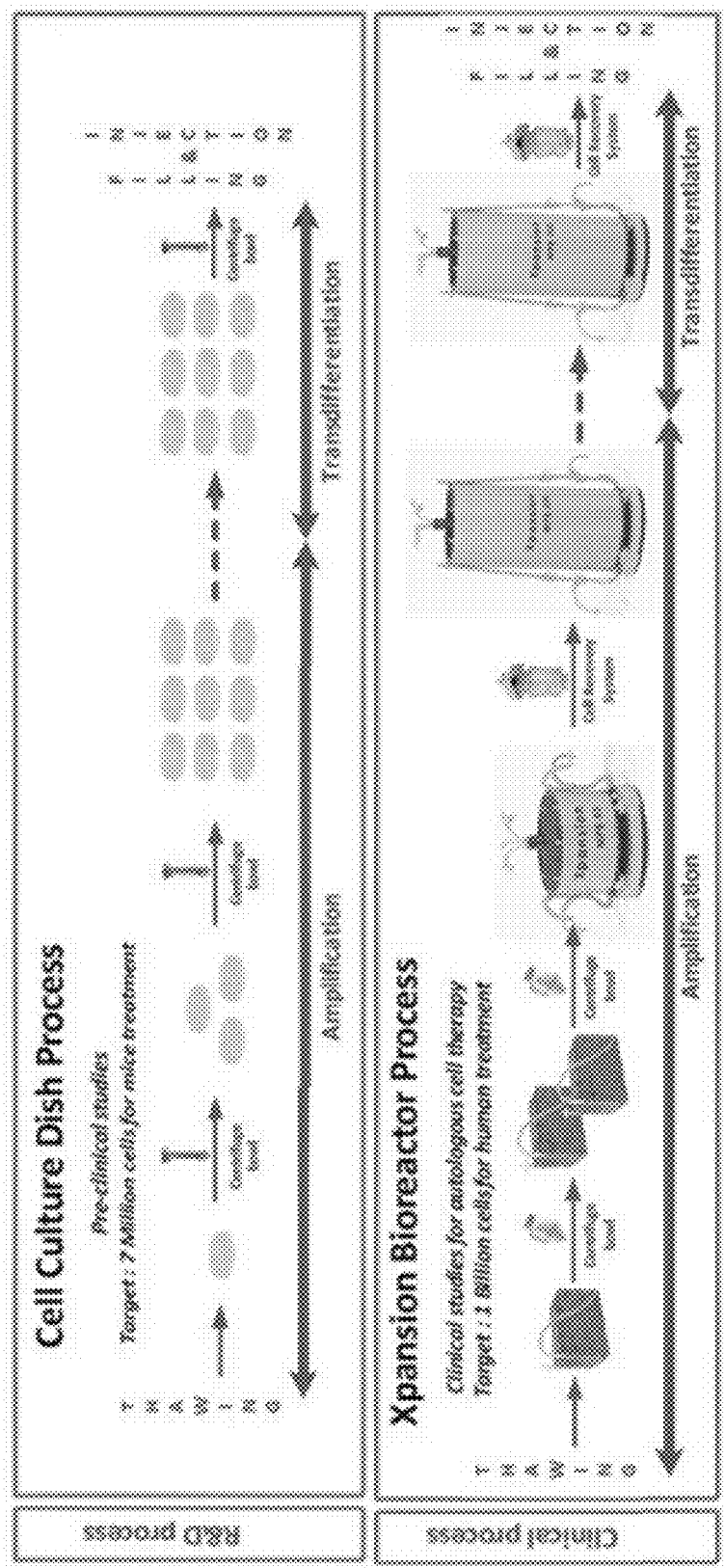
FIG. 27 presents schematics of the human liver-derived cell amplification and transdifferentiation process indicating the preclinical R&D process (Cell Culture Dish Process) and the clinical process (Xpansion Bioreactor Process).

Example 20: Industrialization of Liver Cell Proliferation Process from Petri Dish to the Xpansion Multiplate Bioreactor Aim A bioprocess in cells dishes for preclinical applications was developed that included 2 main steps: liver cell proliferation followed by liver cell transdifferentiation into insulin producing cells. For treatment of patients in human clinical trials, it is anticipated that a dose requirement of about 1 billion cells per patient would be used to ameliorate hyperglycemia in Type 1 diabetes. Such a production scale would require large culture surface area, which the Cell Culture Dish Process (FIG. 27 top) manufacturing strategy does not provide. Thus the goal of this study was to industrialize the cell based Cell Culture Dish Process using the XPANSION platform (bioreactor system; Pall Corporation, USA).

Materials and Methods

The materials used are listed below:
i. Biological materials: Human adult liver-derived cells (primary culture).
ii. Growth medium: Dulbecco's Modified Eagle Medium (DMEM; Life Technologies Cat. 21885-025) supplemented with 10% heat-inactivated fetal bovine serum (FBS; Life Technologies Cat. 10500-064), 1% Penicillin-Streptomycin-Amphotericin B (100λ) (Lonza Cat. 17-745E) and 5 nM Exendin-4 (Sigma-Aldrich Cat. E7144)
iii. Other reagents: Dulbecco's Phosphate Buffered Saline (DPBS; Lonza Cat. 17-512Q) and TrypLE♦ Select (Life Technologies Cat. 12563-029).
iv. Cell culture support: CellBIND♦ CellStack♦ 2-, 5- & 10-chamber (Corning Cat. COS-3310, COS-3311 & COS-3320), Xpansion 50 plates (XP-50) bioreactor (Cat. XPAN050000000) and Xpansion 200 plates (XP-200) bioreactor (Cat. 810155).
v. Cell Recovery Kit for Pall's continuous centrifuge (item 6100043)
vi. Centrifuge control: Cell Recovery System control in 500 mL centrifuge bowl The methods follow the Process Flow Chart presented in FIG. 27. Briefly, pre-cultures were performed as traditional multi-tray cultures. Cells were used in the Xpansion bioreactor(s) at passage 14 & 15. The bioreactor system used is a closed system for reduced risk of contamination. Multi-tray cultures were performed in parallel to the Xpansion culture as a cell growth control with controller set points of pH: 7.3-7.6 and dissolved oxygen (DO): maintained above 50%. The target seeding density was 4,000 cells/cm$^2$ at each passage.

Culture duration was 7-9 days with a medium exchange applied every 2-4 days (XP-50: Days 4, 6 and 8—XP-200: Days 4 and 7) to maintain glucose level above 0.5 g/L throughout the culture.

Results

The results presented here show the successful scale-up of the human liver-derived cell amplification phase from Petri dishes to the Xpansion 200 bioreactor (Pall Corporation, USA).

Cell Growth—

The cell expansion profile presented in FIG. 28 clearly demonstrates that cells are in exponential phase of growth from the first pre-cultures steps to the final bioreactor (XP-200) culture. Within 4 passages, cells were amplified from 2 million to ~1.8 Billion, representing a 1,000-fold biomass increase. Therefore, feasibility of large-scale production of human liver-derived primary cells has been clearly demonstrated, and a target of 1 billion cells/patient, and even nearly 1.8 billion cells/patient per XP-200 was achieved.

Passage 1 was carried out in CellStack10 (CS10), passage 2 was carried out in 2×CS10, passage 3 was carried out in an XP50, and passage 4 was carried out in an XP200.

Figure 30:
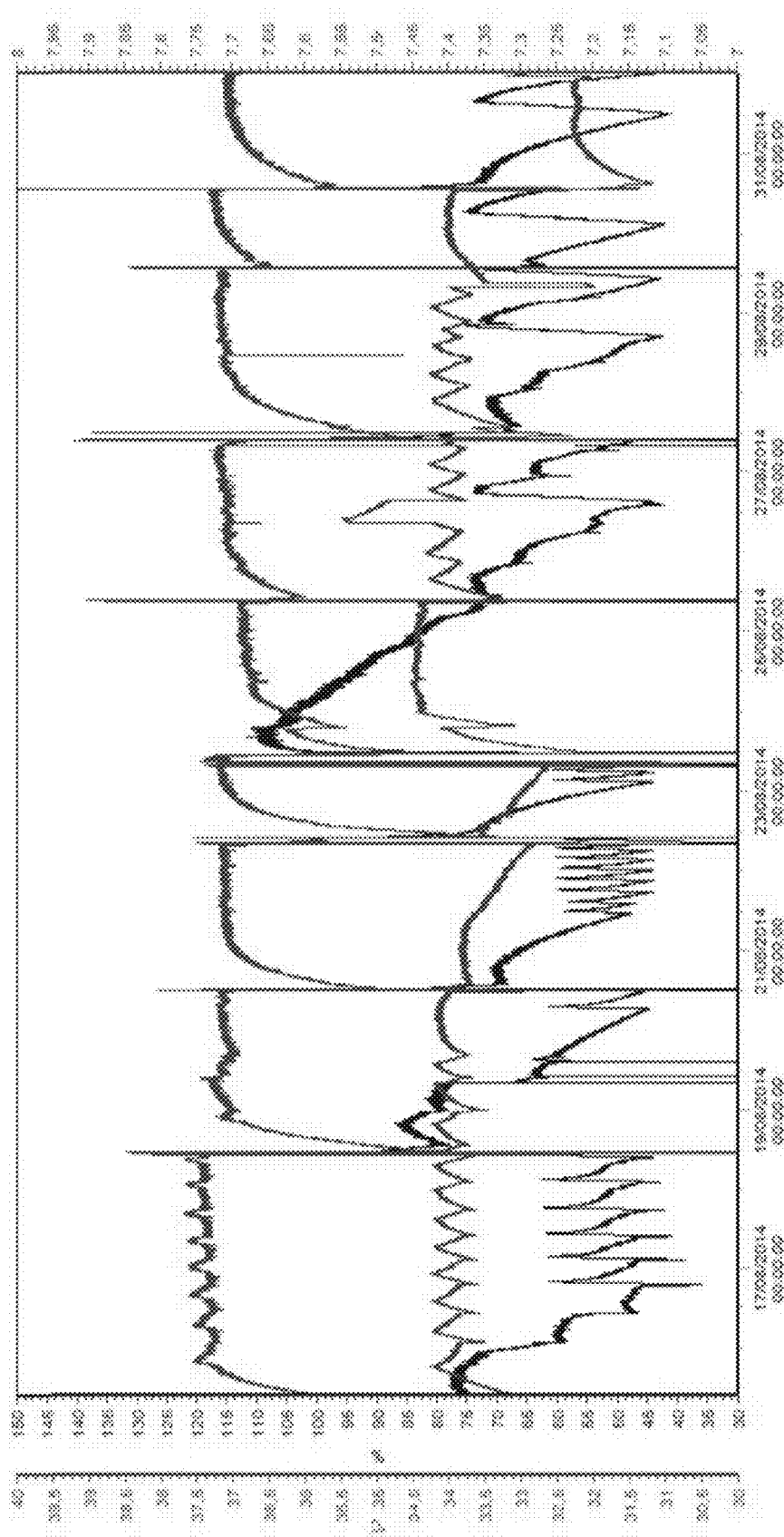
FIG. 30 shows the regulation trend in the bioreactors (XP-50 and XP-200) for pH (green), DO (blue), and temperature (red). Dotted lines represent the set points and peaks were due to bioreactor disconnection for different operations (for example, media exchange).

Population doubling time (PDT) comparison revealed that the human liver-derived primary cells proliferated faster in the Xpansion bioreactor than in the traditional multi-tray system (FIG. 29). Harvested cell densities were around 15,000 cells/cm$^2$ in the Xpansion 50 bioreactor, and 14,000 cells/cm$^2$ in the Xpansion 200 bioreactor, representing ~160% of their respective multitray controls. Better control of the culture environment (pH, DO) is the main hypothesis to explain this result.

pH, Dissolved Oxygen, and Temperature Control Trends in the Xpansion Bioreactor— pH and DO were maintained in their respective expected ranges (FIG. 30). DO was maintained up to 50% of air saturation throughout the whole process, and pH decreased progressively from 7.4 to 7.2 during the last 2 days of each culture due to high cell number at the end of the process. Similar trends were observed during both cultures demonstrating a good reproducibility and scalability.

Microscopic Observation using the Ovizio Holographic Microscope (Ovizio Imaging Systems, Brussels/Belgium)

Cell confluence and morphology are key parameters to monitor in cell therapy processes. To this end, a microscope that allows observation of the top ten plates in the Xpansion bioreactor was used.

Figure 31A:
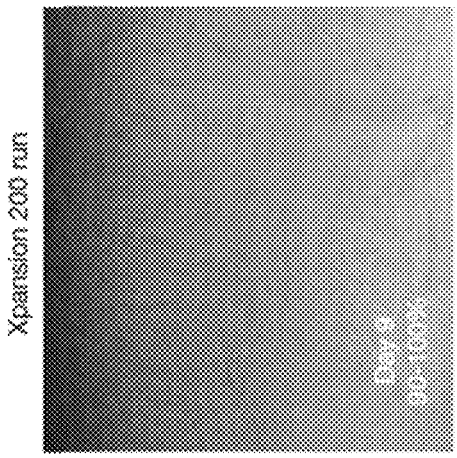
FIGS. 31A-31D present microscopic observations of cells within the Xpansion bioreactor (FIGS. 31A and 31B) and control multi-tray systems (FIGS. 31C and 31D) before harvest on day 9.
Figure 31B:
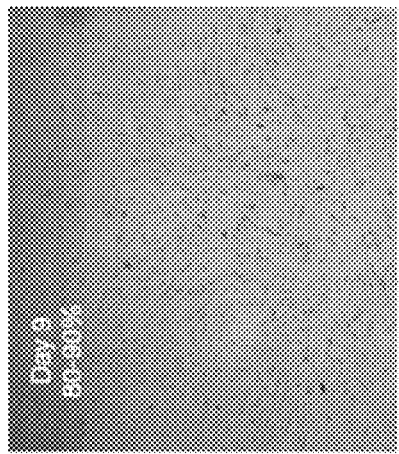
Figure 31C:
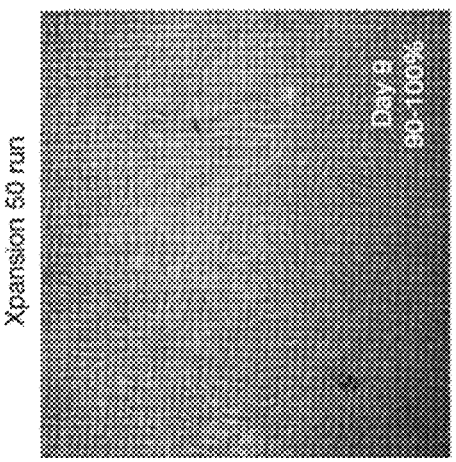
Figure 31D:
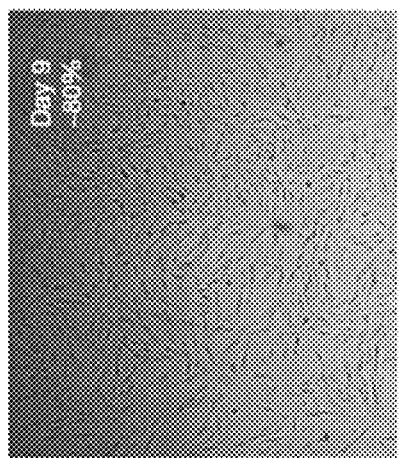

Micrograph images presented in FIGS. 31A-31D confirm the homogeneous distribution of human liver-derived primary cells throughout the Xpansion plates. Cell confluence was determined to be approximately 90% after 9 days of culture, and estimated to be equivalent in both the XP-50 and XP-200 bioreactors (FIGS. 31A and 31B). At both the 50- and 200-plate scale, confluence in the Xpansion system was slightly higher than that from the control multi-tray system. These images also demonstrate that the cell morphology was not affected by successive culture in the Xpansion system, or by continuous centrifugation used for cell recovery. Control cells grown using a multi-tray process are shown in FIGS. 31C and 31D. Data demonstrated that human liver-derived primary cell proliferation using the Xpansion bioreactor did not alter the transdifferentiation properties or the insulin secretion profile of transdifferentiated cells (Data not shown).

Conclusion

Bioreactors were successfully used to scale-up the human adult liver-derived cells proliferation process. The results herein show that by using a process including a bioreactor platform, cells could be reliably amplified from 1 million up to 1.8 billion cells. This level of scale up potentially makes available 1.8 billion cells for administration to patients during a cell-based autologous therapy targeting diabetes. This compares to the only 7 million cells produced using a cells dish process, e.g., petri dishes (data not shown). Importantly, the process using bioreactors preserved cell viability, potential for transdifferentiation, and the cell's insulin secretion profile.

Example 21: Protocol for Producing Autologous Insulin Producing (AIP) Cells for the Treatment of Diabetes Aim The aim of this study was developing an industrial scale protocol for producing autologous insulin producing (AIP) cells from non-β pancreatic cells for the treatment of diabetes. By correcting functionally for malfunctioning pancreatic insulin producing β-cells with new functional tissues generated from the patient's own existing organs, a cell-based autologous therapy could successfully target diabetes in a subject.

The protocol presented herein employs a molecular and cellular approach directed at converting human liver derived cells into functional insulin-producing cells by transcription factors induced transdifferentiation (FIG. 32). This therapeutic approach generates Autologous Insulin Producing (AIP) cells on an industrial scale, overcoming the shortage in tissue availability from donors.

Overview of the Protocol

FIG. 33 provides an overview of the protocol provided here, demonstrating an approximate time from biopsy to finished product of 6-weeks, along with approximate cell numbers at each step. FIG. 34 presents a flowchart of the human insulin producing cell product manufacturing process, which may in one embodiment be autologous or allogeneic insulin producing cells (AIP). Details are provided below.

Obtaining Liver Tissue Step 1 of FIG. 34

Liver tissue was obtained from adult human subjects. All liver tissue obtained were received under approval of the Helsinki Committee of the Medical Facility. Accordingly, all liver tissue donors signed an informed consent and Donor Screening and Donor Testing was performed to ensure that biopsies from donors with clinical or physical evidence of or risk factors for infectious or malignant diseases were excluded from manufacturing of human insulin producing cells.

Liver biopsies were obtained in an operating theatre by qualified and trained surgeons. A biopsy of the size of about 2-4 g of liver tissue was taken from eligible patients and transported at 2-8° C. in University of Wisconsin (UW) solution in a sterile bag to the GMP facility.

In Vitro Culture/Steps 2 and 3 of FIG. 34

At the manufacturing site, liver biopsies were processed as for adherent cells. Briefly, biopsy tissue was cut into thin slices and digested by collagenase type I for 20 min at 37° C. Subsequently, cells were repeatedly digested with trypsin in order to obtain isolated single cells; initial experiments had shown that approx. 0.5×10$^6$ cells can be isolated per gram biopsy.

Cells were then expanded ex vivo in cells medium supplemented with 10% FCS, Exendin-4 and a mix of antibiotics (Penicillin, Streptomycin and Amphotericin B). Cells were passaged at 37° C. in a humidified atmosphere of 5%

CO₂/95% air (up to 20 passages) using pre-treated Fibronectin-coated tissue culture dishes. Medium was changed daily during the first three days post biopsy plating to remove non-adherent cells followed by twice a week, after the first cell passage. At the time of the first cell passage at least one aliquot of cells was cryopreserved (see below; Optional Step of FIG. 34).

Cells were passaged 1:3 using trypsin until the desired number of cells was generated (about 1-3 billion cells, within about 4 to 7 weeks). Expansion of cells included use of Multi-plate systems as described in Example 20 and shown in FIG. 33 at approximately week 4 through weeks 7. (Step 3 of FIG. 34)

Human liver cells that adhered to the tissue culture plates underwent epithelial to mesenchymal transition (EMT) and efficiently proliferated. Close to 100% of these EMT-like cells displayed the known mesenchymal characteristics (CD29, CD105, CD90 and CD73) but also expressed adult hepatic markers such as albumin and AAT. The cells neither express hepatoblast nor "stemness" markers. Table 8 below shows the results of analysis of these EMT-like cultured liver cells for the presence of mesenchymal, hematopoietic, and hepatic markers on the cultured liver cells prior to transdifferentiation (TD).

TABLE 8

| Before Transdifferentiation | Specification |
|---|---|
| Mesenchymal markers | |
| CD105, CD73, CD90, CD44 | >95% |
| Haemapoeitic markers | <2% |
| Hepatic markers | |
| Albumin | >80% |
| AAT | >60% |

The percentages shown in Table 8 are at low passage number.

Cryopreservation of Passage 1 Cells (FIG. 34)

Briefly, Passage 1 cells were cryopreserved in DMEM supplemented with 10% FBS and 10% DMSO in 2 ml cryovials (minimum of 0.5×10⁶ cells). It is recommended to cryopreserve cells at the earliest passage possible. Frozen cells were first stored at −70° C. for 24-48 hours and then transferred to liquid N₂ for long term storage.

Thawing of Cryopreserved Cells (FIG. 34)

Cryopreserved cells were thawed using well-known methods in the art. Briefly, vials were removed from liquid N₂ and allowed to slowly thaw until sides were thawed but center was still frozen. Cells were gently transferred to tissue culture plates. Once cells have attached to the plate, in vitro processing (Steps 2 and 3 of FIG. 34) to expand the cell culture was performed.

Select Predisposed Liver Cells (FIG. 34)

An option at Step 3 of FIG. 34 is to sort the Primary Liver Cells in order to enrich for cells predisposed to transdifferentiation. For example, cells could be sorted for glutamine synthetase response element (GSRE) activation (GS enriched cells), as described herein above in Examples 10-15. Alternatively, cells could be enriched for having an active Wnt signaling pathway, wherein they are predisposed to respond to Wnt signaling, as described herein above in Example 17. In addition, cells could be enriched by monitoring increases or decreases of expression of certain genes, for example decrease in expression of ABCB1, 1TGA4, ABCB4, or PRNP, or any combination thereof, or increases in expression of HOMER1, LAMP3, BMPR2, ITGA6, DCBLD2, THBS1, or VAMP4, or any combination thereof, as described herein above in Example 16. The cell population could be treated with lithium, as described in Example 23, in order to enhance the predisposition of cells to transdifferentiation. Following enrichment for predisposition to transdifferentiation, cells are used at Step 4 of FIG. 34.

Trans-Differentiation (Step 4 of FIG. 34)

For trans-differentiation cells were grown in trans-differentiation medium for an additional 5 days. Trans-differentiation medium is Dulbecco's minimal essential medium (1 g/l of glucose) supplemented with 10% FCS, Exendin-4, Nicotinamide, EGF and a mix of antibiotics (Penicillin, Streptomycin and Amphotericin B).

Two different protocols were used for transdifferentiation of cells. Cells were transdifferentiated using the Hierarchy (1+1+1) sequential protocol or using the 2+1 protocol. Examples of each method are provided below.

Hierarchy (1+1+1) Sequential Protocol

Ex vivo expanded liver cells were then sequentially infected with 3 serotype-5 recombinant replication-deficient adenovirus vectors, each carrying the human gene for one of the pancreatic Transcription Factors (pTFs), PDX-1, Neuro-D or MafA, under the control of the cytomegalovirus (CMV) promoter. The 3 human pTF genes had been inserted into the same backbone of FGAD vectors under the control of the CMV promoter. The CMV promoter is a heterologous promoter that is usually turned off within 3-4 weeks after infection. Nevertheless the short-term expression of the ectopic pTF genes was sufficient to induce the endogenous human homologs.

FGAD vectors were selected as an optimal gene delivery tool for inducing developmental redirection. Examples above demonstrated that introduction of these ectopic genes into primary adult human liver cells acts as short term triggers for an irreversible process of reprogramming of adult cells. On the other hand, the recombinant adenoviruses were relatively safe as they do not integrate into the host genome and therefore do not disrupt the host sequence of genetic information. PDX-1 induces epigenetic alterations in the chromatin structure, thus allowing the activation of otherwise silent genetic information, while turning off the host repertoire of expressed genes (compare the results of Tables 8 and 9).

The transdifferentiation process was performed using a closed automatic Xpansion bioreactor system (Pall Life Sciences), following the flow of steps presented in FIG. 33. The bioreactor system was used for cultivation of cell cultures, under conditions suitable for high cell concentrations. The bioreactor system was constructed of two main systems, a control system and a bioreactor itself (vessel and accessories).

The parameters of the process were monitored and controlled by the control console which included connectors for probes, motor and pumps, control loops for Dissolved Oxygen (DO), pH, a gases control system and place in the incubator for temperature control. The controlled process parameters (such as temperature, pH, DO etc.) could be displayed on the operator interface and monitored by a designated controller.

Cell Culture Growth Procedure in the Bioreactors

250±50×10⁶ cells were seeded in a sterile XP-200 bioreactor. The growth medium in the bioreactor was kept at the following conditions: 37° C., 70% Dissolved Oxygen (DO) and pH 7.3. Filtered gases (Air, CO₂, N₂ and O₂) were supplied as determined by the control system in order to keep the DO value at 70% and the pH value at 7.3. Growth media was changed when the medium glucose concentration decreased below 500 mg/liter. The medium was pumped from the feeding container to the bioreactor using sterile silicone tubing. All tubing connections were performed with a tube welder providing sterile connectors. A sample of the growth medium was taken every 1-2 days for glucose, lactate, glutamine, glutamate and ammonium concentration determination. The glucose consumption rate and the lactate formation rate of the cell culture enabled to measure cell growth rate. These parameters were used to determine the harvest time based on accumulated experimental data.

Harvest of the Cells from the Bioreactor

The cell harvest process started at the end of the growth phase (8-16 days). The culture was harvested in the Class-100 laminar area as follows:

The bioreactor vessel was emptied using gravitation via tubing to a waste container. The bioreactor vessel was then refilled with 22 L pre-warmed PBS (37° C.). The PBS was drained via tubing by pressure or gravity to the waste bottle. The washing procedure was repeated twice.

On day 3, cells were detached from culture dishes using trypsin and resuspended. Resuspended cells were infected with the MafA adenoviral vector using an MOI of 50. Cells were then seeded onto culture dishes are incubated for three days in a humidified 37° C. incubator supplied with 5% $CO_2$.

Cells were then recovered and analyzed for markers and glucose regulated processed insulin secretion. Control cells included those propagated and incubated following the same protocol but without addition of adenovirus.

Materials and Experimental Methods

FACS analysis of membrane markers—cells were stained with monoclonal antibodies as follows: 400,000-600,000 cells were suspended in 0.1 ml flow cytometer buffer in a 5 ml test tube and incubated for 15 minutes at room temperature (RT), in the dark, with each of the following monoclonal antibodies (MAbs):

| Ab | Andibody full name | Company | Cat. No. |
|---|---|---|---|
| PDX1 | BD Pharmingen ™ PE Mouse anti-PDX-1 | BD | 562161 |
| | Human/Mouse PDX-1/IPF1 Phycoerythrin MAb | R&D Systems | IC2419P |
| | Human/Mouse PDX-1/IPF1 Allophycocyanin Mab | R&D Systems | IC2419A |
| NEUROD1 | BD Pharmingen ™ PE Mouse Anti-NeuroD1 | BD | 563001 |
| | BD Pharmingen ™ Alexa Fluor ® 647 Mouse anti-NeuroD1 | BD | 563566 |
| MAFA | Anti-KLRG1 (MAFA-)-PE-Vio770, human (clone; REA261) | Miltenyi Biotec | 130-103-641 |
| | Anti-KLRG1 (MAFA)-APC-Vio770, human (clone: REA261) | Miltenyi Biotec | 130-103-642 |
| Vimentin | BD Pharmingen ™ PE Mouse Anti-Human Vimentin | BD | 562337 |
| | BD Pharmingen ™ Alexa Fluor ® 488 Mouse Anti-Human Vimentin | BD | 562338 |
| E-Cadherin | BD Horizon ™ BV421 Mouse Anti-E-Cadherin | BD | 564186 |
| | BD Pharmingen ™ PE Mouse anti-E-Cadherin | BD | 562526 |
| | BD Pharmingen ™ Alexa Fluor ® 488 Mouse Anti-Human CD324 (E-Cadherin) | BD | 563570 |
| | BD Pharmingen ™ PerCP-Cy ™5.5 Mouse Anti-Human CD324 (E-Cadherin) | BD | 563573 |
| | BD Pharmingen ™ Alexa Fluor ® 647 Mouse Anti-Human CD324 (E-Cadherin) | BD | 563571 |
| | BD Pharmingen ™ PE Mouse Anti-Human CD324 (E-Cadherin) | BD | 562870 |
| | BD Horizon ™ PE-CF594 Mouse Anti-Human CD324 (E-Cadherin) | BD | 563572 |

In order to release the cells from the surface, 22 L pre-warmed to 37° C. of Trypsin-EDTA (Trypsin 0.25%, EDTA 1 mM) was added to the bioreactor vessel. 500 ml FBS was added to the bioreactor vessel and the cell suspension was collected to a sterile container. Cell suspension was centrifuged (600 RPM, 10 min, 4° C.) and re-suspended in culture media.

Hierarchy (1+1+1) Viral Infection Steps

The ectopic transgenes were sequentially administered by recombinant adenoviruses on three successive days. Sequential administration of the ectopic genes has been documented to both increase the trans-differentiation efficiency and to increase the maturation of the cells, specifically along the β cell lineage and function.

The trans-differentiation procedure took approx. 7 days, at the end of which cells are washed to remove the unincorporated recombinant adenoviruses. Briefly:

On day 1, resuspended cells were infected with the PDX-1 adenoviral vector using an MOI of 1,000. Cells were then seeded onto culture dishes are incubated overnight in in a humidified 37° C. incubator supplied with 5% $CO_2$.

On day 2, cells were detached from culture dishes using trypsin and resuspended. Resuspended cells were infected with the NeuroD1 adenoviral vector using an MOI of 250. Cells were then seeded onto culture dishes are incubated overnight in in a humidified 37° C. incubator supplied with 5% $CO_2$.

Harvesting AIP cells (Step 5 of FIG. 34) Cells were then washed twice with flow cytometry buffer, resuspended and analyzed by flow cytometry using an FC-500 flow Cytometer (Beckman Coulter). Negative controls were prepared with relevant isotype fluorescence molecules.

Packaging and Release

At the end of manufacturing, AIP cells will be packed for shipment and released at the manufacturing site. It is planned to ship AIP cells at 2-8° C. to the hospitals.

Results of Hierarchy (1+1+1) Protocol

The adenoviral infection of the cells resulted in transient expression of the transgenes, which triggers permanent induction of endogenous genes, resulting in stable transdifferentiation to AIP cells (data not shown). As a result, there was no modification or insertions of viral DNA in the final product.

Analysis of harvested AIP cells (Step 6 of FIG. 34)

An analysis of the transdifferentiated liver cells (AIP cells) for the presence of mesenchymal, hematopoietic, and hepatic markers is presented in Table 9. Negative markers include hematopoietic markers.

TABLE 9

| % CD105 | % CD73 | % CD90 | % CD44 | % Negative markers |
|---|---|---|---|---|
| 99.32 | 99.85 | 99.55 | 99.77 | 0.93 |
| 98.75 | 99.71 | 99.67 | 99.70 | 0.73 |

TABLE 9-continued

| % CD105 | % CD73 | % CD90 | % CD44 | % Negative markers |
|---|---|---|---|---|
| 97.89 | 98.71 | 99.80 | 99.77 | 0.94 |
| 96.77 | 98.60 | 99.50 | 99.64 | 0.58 |

While variability was noted across different patient samples in Xpansion bioreactors, in all cased cell density of harvested cells was greatly increase as compared with the starting culture (FIG. 35).

The harvested AIP cell product was analyze to identify expression of numerous markers. Identity was by RT-PCR and FACS. The results presented in Tables 10 and 11 below show the fold increase of endogenous expression of β-cell pancreatic marker genes including PDX-1, NeuroD, MafA, Pax4, Nkx6.1 and insulin.

TABLE 10

| RT-PCR | Fold increase (over control) |
|---|---|
| Pdx1 | >$10^5$ |
| NeuroD | >$10^4$ |
| MafA | >$10^3$ |
| Insulin | >$10^1$ |

TABLE 11

| RT-PCR | Fold increase (over control) |
|---|---|
| Glucagon | >$10^2$ |
| Somatostatin | >$10^1$ |
| Nkx6.1 | >$10^1$ |
| Pax4 | >$10^1$ |

Figure 36A:
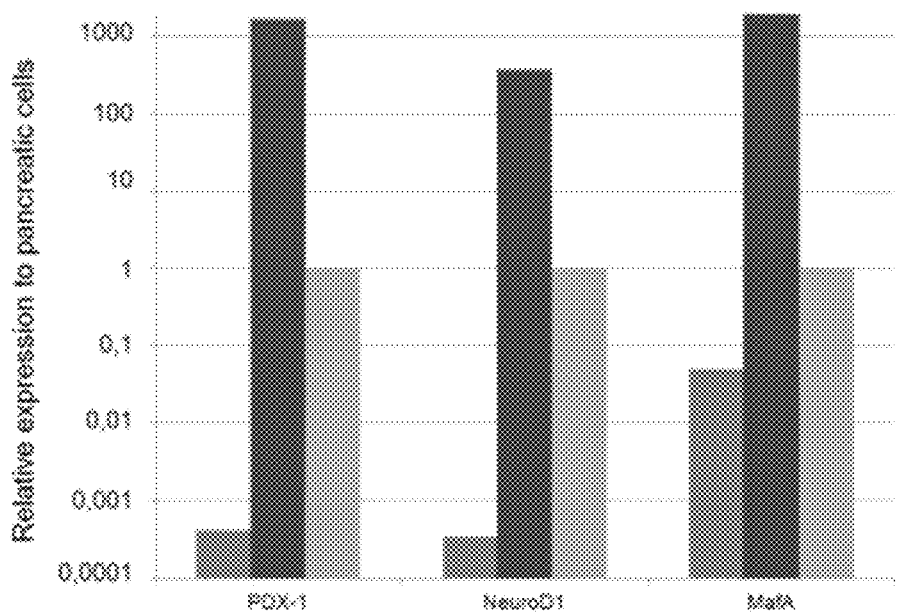
FIGS. 36A and 36B presents bar graphs displaying typical results of endogenous gene expression from populations of transdifferentiated human primary liver cells, the results showing an increase in endogenous of pancreatic cell markers (PDX-1, NeuroD1, MafA, glucagon, and somatostatin) compared with control untreated (non-transdifferentiated) cells.
Figure 36B:
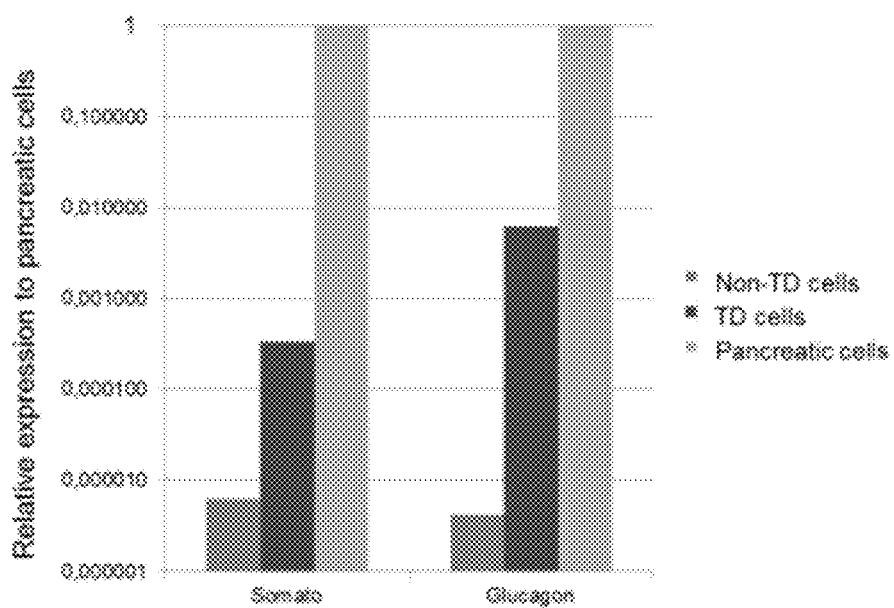

The bar graphs presented in FIGS. 36A and 36B show the typical results obtained following use of the hierarchy protocol. A comparison of transdifferentiated liver cells (AIP cells) with pancreatic cells and the control population of non-transdifferentiated liver cells is presented wherein it can be seen the AIP cells show a significant increase in pancreatic cell markers compared with control.

The result of further characterization of the cells for hepatic versus pancreatic phenotype of function of the AIP cells is presented in Table 12 below. The significant decrease of hepatic markers in PDX-1 cells combined with the increase of pancreatic cell markers indicates successful transformation of liver cells to cells having phenotype and function of pancreatic β-cells.

TABLE 12

| AIP cells product specification, as identified by FACS | |
|---|---|
| After Trans-differentiation | Specifications |
| Hepatic markers in Pdx-1 + positive cells | <1% |
| Each ectopic pTF | >80% |
| Insulin/c-peptide | >10% |
| NKX 6.1 | >10% |
| Glucagon | >10% |

Analysis for dead cells within the population of harvested AIP cells showed that less than 20% of the cells were dead (data not shown).

Figure 37:
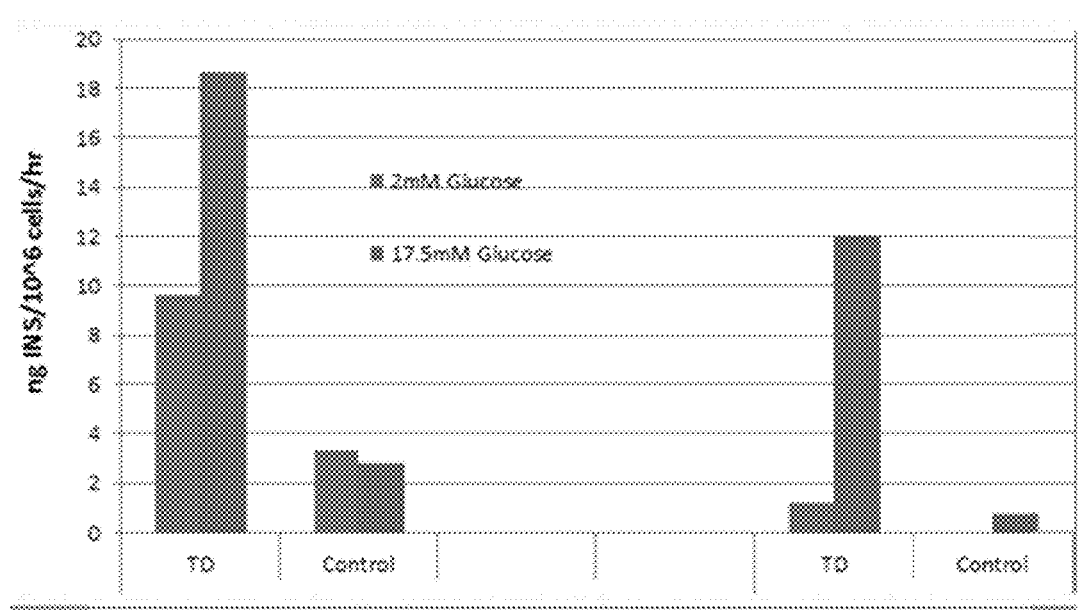
FIG. 37 presents the results of testing for AIP cell product Potency (glucose regulated insulin secretion, assayed by ELISA).

The harvested AIP cell product was also analyze for function secretion of insulin. FIG. 37 shows AIP cell product Potency (glucose regulated secretion of insulin as measured using ELISA). The AIP cell product tested represents a transdifferentiated population of cells that had been expanded in an XP-200 bioreactor. Insulin secretion was measured by GSIS (glucose stimulated insulin secretion at low (2 mM) and high (17.5 mM) glucose concentrations with KRB+0.1% BSA RIA-grade, or recombinant BSA). Results are presented as ng insulin per million cells per hour and show the significant increase of response of AIP cells.

2+1 Transdifferentiation (TD) Protocol

Figure 38:
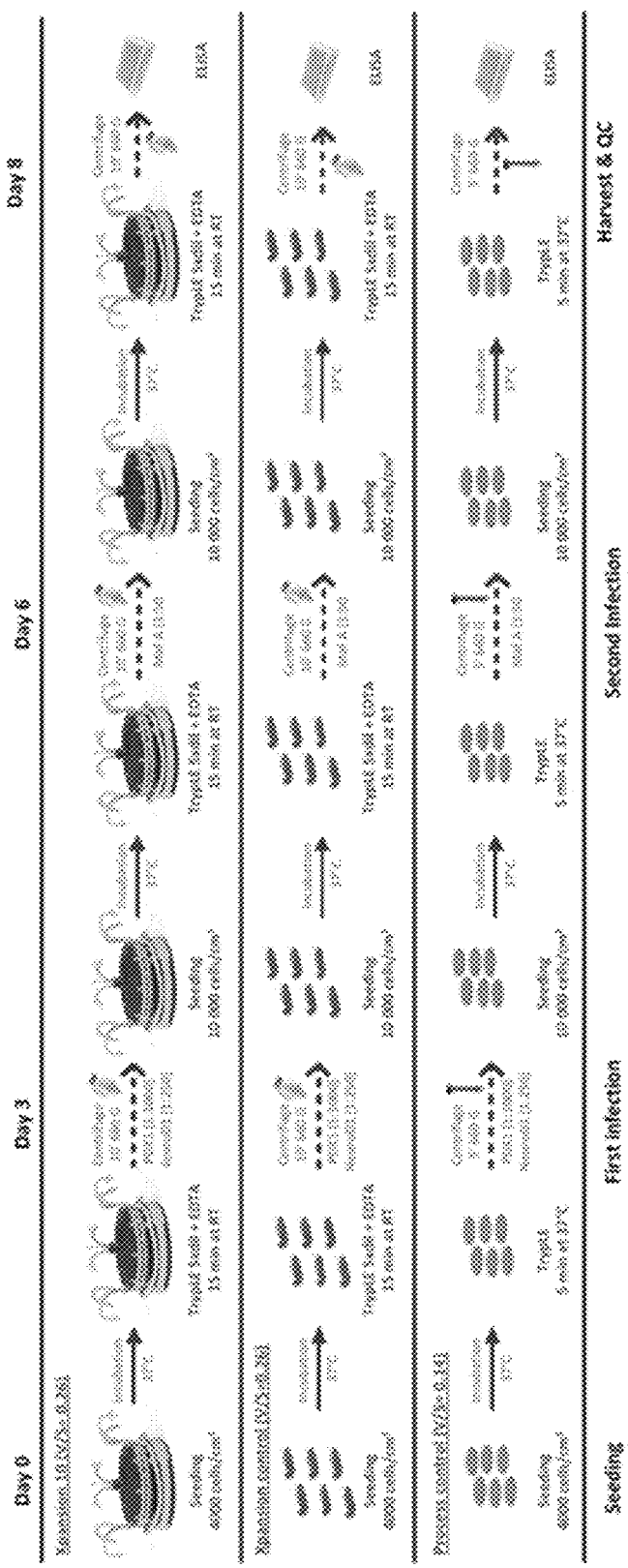
FIG. 38 present a flowchart showing three different "2+1" transdifferentiation protocols, including protocols using multi-system bioreactors, for the production of human insulin producing cells from non-pancreatic cells, as shown here starting from liver cells. The flowchart indicates target cell densities at seeding and plating post infection, as well as the first infection comprising infecting with adeno viral vectors comprising DNA encoding PDX-1 and NeuroD1 polypeptides, and the second infection comprising infecting with an adenoviral vector comprising DNA encoding MafA. In all, seeding to harvest occurs in about 8 days.
Figures 39A, 39B, 39C, 39D:
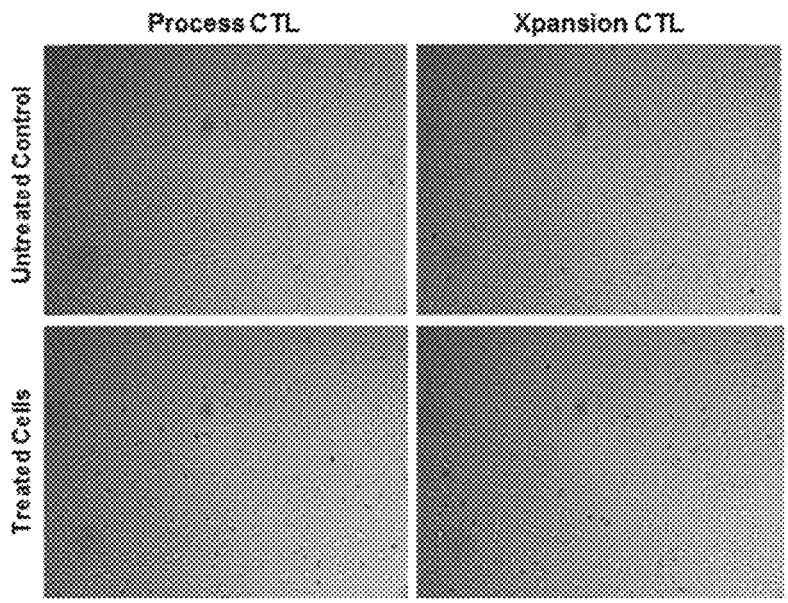
FIGS. 39A-39D present micrographs of cell densities at day 6 at the time of second infection, including an image of untreated control cells.
Figure 40A:
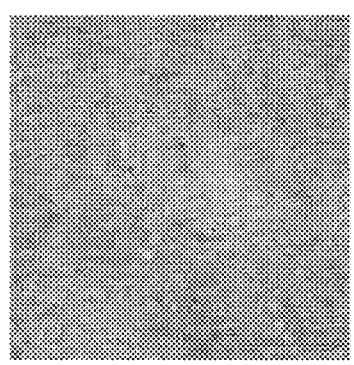
FIGS. 40A-40B present micrographs of cell densities at day 6 at the time of second infection from plates 3 (FIG. 40A) and 5 (FIG. 40B) of the Xpansion-10 multi-system bioreactor.
Figure 40B:
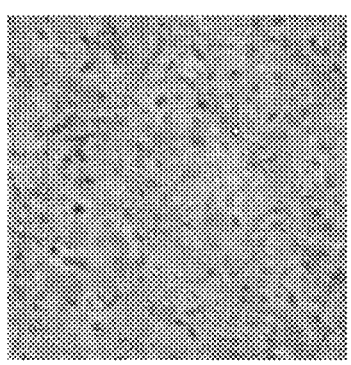
Figure 43:
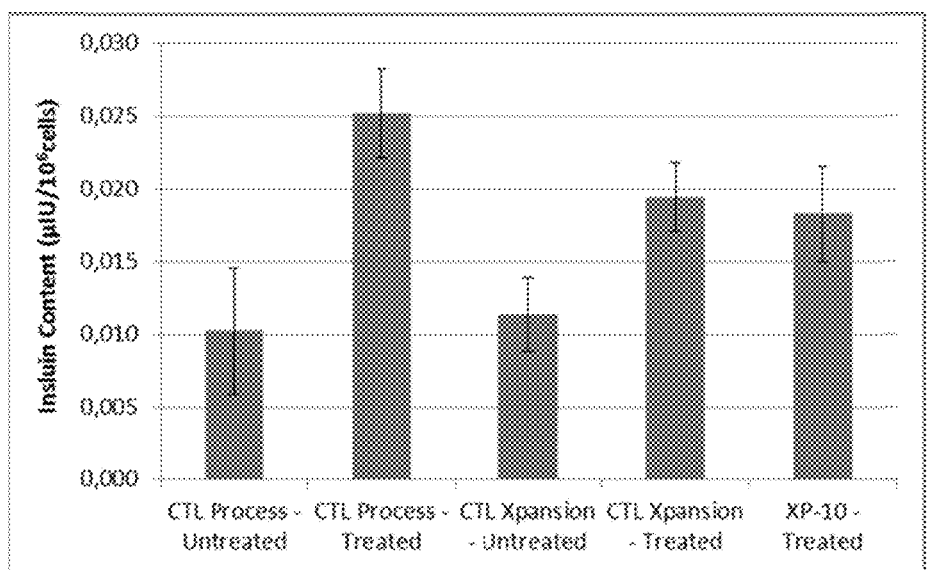
FIG. 43 presents a bar graph showing the results of an insulin content assays for cells produced using the "2+1" protocol (See FIG. 38), showing that transdifferentiation in a bioreactor system is not only feasible, but yields human insulin producing cells wherein the cells have increased insulin content compared with control untreated cells.

FIG. 38 presents "2+1" TD protocols using Xpansion bioreactor systems as well as a process control. The results of using the "2+1" TD protocol in combination with a multi-system bioreactor demonstrated the feasibility of this protocol, which efficiently produced AIP product cells. The first infection was performed at day 3 using either an adenoviral vector comprising a nucleic acid that encoded PDX-1 and NeuroD1 polypeptides or two adenoviral vectors—one comprising a nucleic acid encoding PDX-1 and the other comprising a nucleic acid encoding NeuroD1. The MOI for PDX-1 as 1:1,000 and for NeuroD1 was 1:250. Cells were then incubated for 3 days and a second infection was performed on day 6 using an adenoviral vector comprising a nucleic acid encoding MafA (1:50 MOI). The cells were harvested two days later at day 8 and screened for quality control markers, similar to that described above when the hierarchy (1+1+1) protocol was used.

Observation of cell cultures at the time of the second infection (day 6) showed similar confluences independent of the conditions used (FIGS. 39A-39D and 40A-40B). At the time of final harvest cells processed under CTL (control) conditions presented slightly higher cell confluence than other conditions (FIGS. 41A-41D). Differences in cell densities were due mainly to different seeding densities, and cell recovery yields and mortality on days following infection.

The insulin content of harvested cells was assayed and the results presented in FIG. 42 demonstrates increased insulin content (micro International Units/million cells) for cells transdifferentiated under all three 2+1 protocols tested, as compared with controls that were untreated (not infected with viral vectors comprising nucleic acids encoding PDX-1, NeuroD1, and MafA). The process CTL condition presented expected trend yielding significantly higher insulin content than untreated cells (~2.5× higher). The Xpansion CTL condition also presented expected trend wherein treated cells presented significantly higher insulin content than untreated cells (~1.7× higher). Cells transdifferentiated in the Xpansion 10 system presented similar insulin content than treated cells of the Xpansion CTL condition (~1.7× higher than untreated control)

Use of the "2+1" transdifferentiation protocol was efficient (reduced step number and opportunities for cell lose) in producing AIP cell product with significantly higher insulin content than untreated liver cells.

Purity Assays

Purity assays were developed to ensure that more than 90% of the cells during the expansion and transdifferentiation steps have a mesenchymal stem cell (MSC)-like phenotype (See above in Methods). These purity assays were used independent of the protocol used for transdifferentiation. Cultivated MSCs should stain positive for CD73, CD90, CD105, and CD44. In addition, MSCs should be negative for CD45, CD34, CD14 or CD11b, CD19 or CD79#, and HLA-DR surface molecules. Previous results (FIGS. 44A and 44B) demonstrated that MSC markers were stable over time and during transdifferentiation of liver cells. Results showing the MSC-like phenotype of AIP cells are presented in Tables 8 and 9. Both flow cytometry and immunofluorescence assays were used to examine these parameters.

Example 22: Analysis of Digestion Methods

Objective

The objective of this study was to verify that different digestion methods do not impact the ability of liver cells to be transduced by adenoviruses.

Methods

Briefly, liver cells were infected with Ad.CMV.GFP and the expression of GFP was measured after 96 hours. Liver cells were transduced with 10, 100, and 500 moi of Ad5.CMV.GFP virus or left untreated. After 96 hours, GFP expression was measured by fluorescent microscopy (FIG. 45A, FIG. 46A) and by FACS (FIGS. 45B-45C, FIGS. 46B-46C).

Results

Figure 45A:
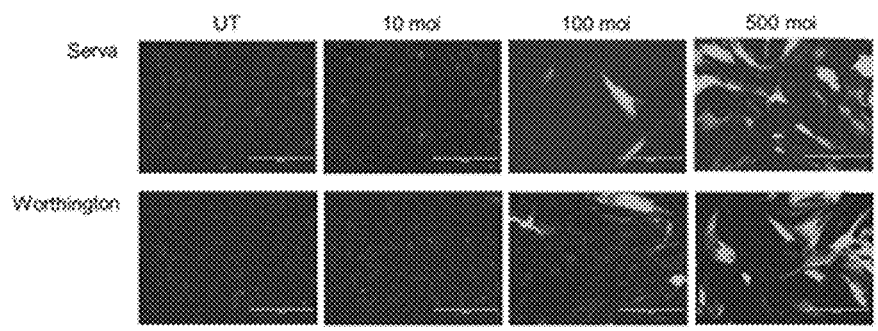
FIGS. 45A-45C transduction efficiency of BP001 liver cells.
Figure 45B:
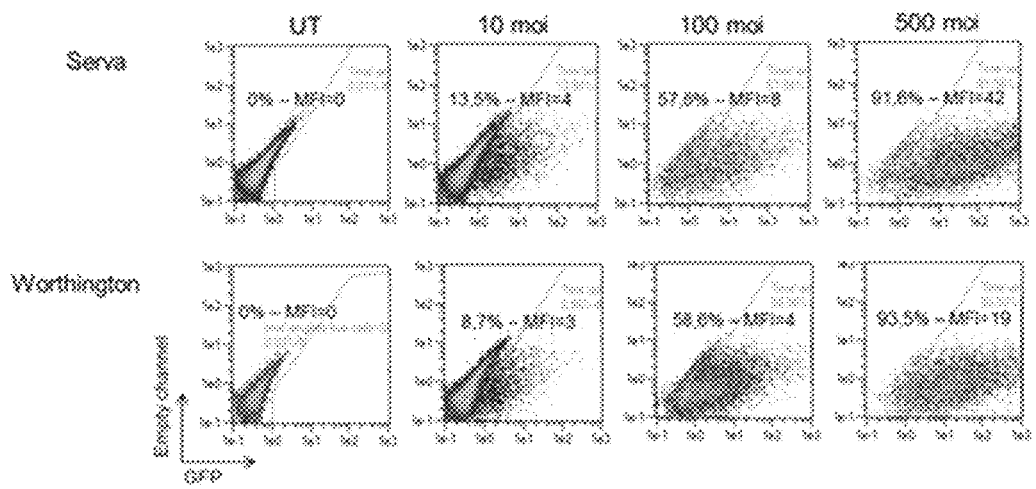
Figure 45C:
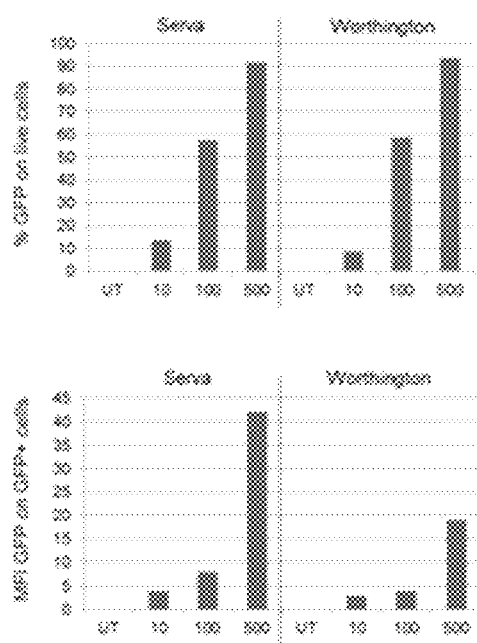
Figure 46A:
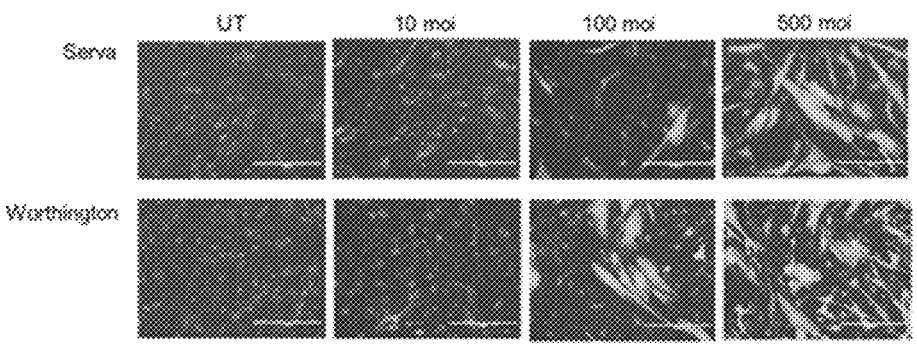
FIGS. 46A-46C show transduction efficiency of TS001 liver cells.
Figure 46B:
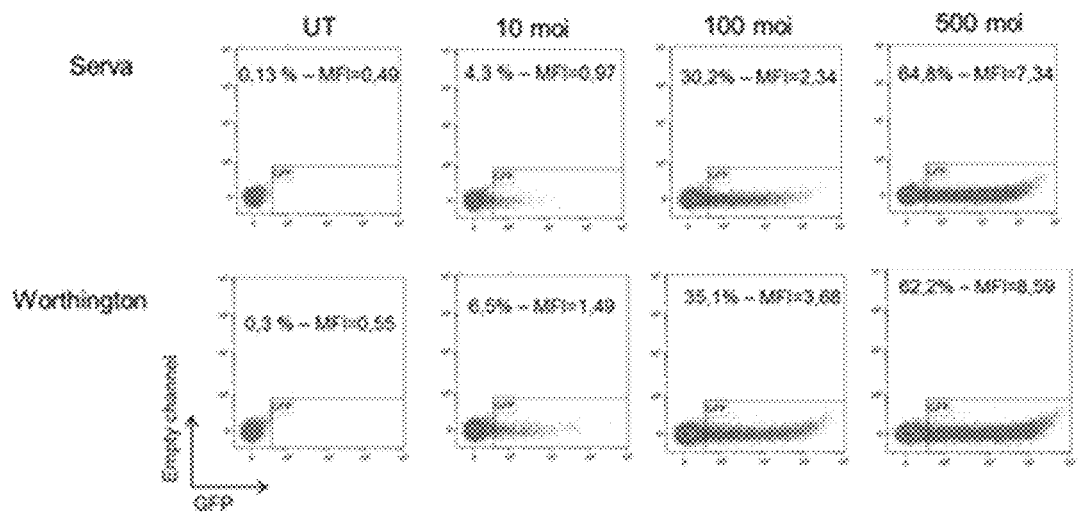
Figure 46C:
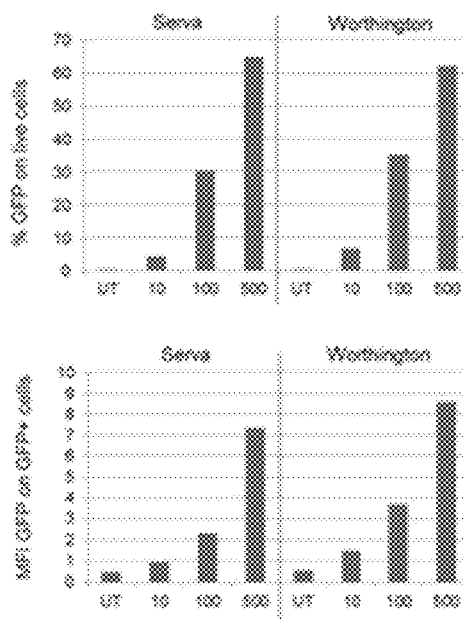

FIGS. 45A-45C shows the efficiency of transduction of BP001 cells, derived from digestion of livers with Serva and Worthington collagenases. Although the percentage of transduced cells was similar, liver digested with Serva collagenase produced more GFP than liver digested with Worthington collagenase, as shown by the GFP fluorescent intensity (FIGS. 45B and 45C). Similarly, transduction efficiency of TS001 cells was not impacted by the use of Serva collagenase (FIGS. 46A-46C).

Example 23: Wnt Treatment Prior to Transdifferentiation Improves Transdifferentiation Competence Objective The objective of this study was improve transdifferentiation competence within a cell population.

As described above at Example 17, active WNT signaling characterized the eGFP+ pre-disposed population. While the experiment described above demonstrated that induction of WNT signaling improved transdifferentiation efficiency when applied together with the transdifferentiation transcription factors, it did not show whether the pre-existing WNT signaling in eGFP+ is associated with their increased competence to redirect their differentiation fate.

Methods

In order to test whether WNT signaling endows the cells with competence for transdifferentiation, eGFP+ cells were treated with 10 mM lithium (Li) for 48 hours prior to the addition of the transdifferentiation factors. The lithium was then removed from the media when the pancreatic transcription factors were added.

Results

Figure 48A:
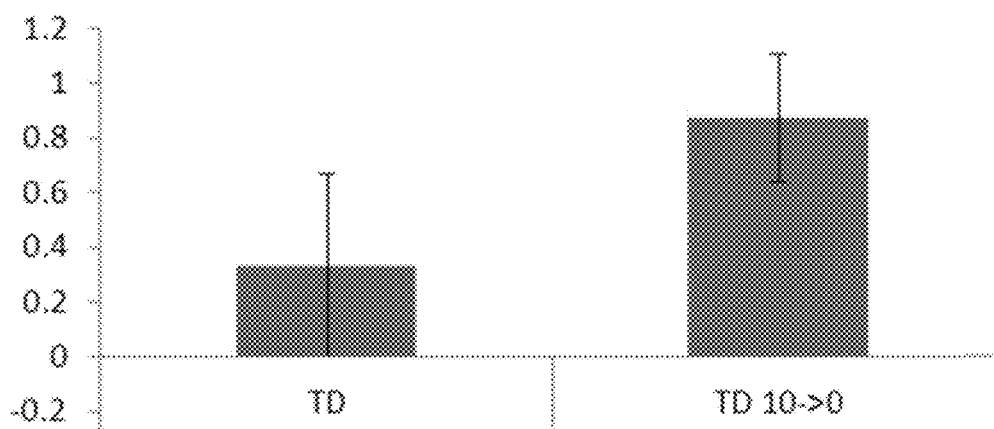
FIGS. 48A-48C shows pre-existing WNT/β-catenin signal disposes cells to efficient transdifferentiation. WNT signaling was induced by Li for 48 hours prior to transdifferentiation, which was then removed (Li day −2) or maintained (Li day −2 onward) throughout the transdifferentiation protocol. Insulin secretion was measured by ELISA, in response to 17.5 mM glucose stimulation.
Figure 48B:
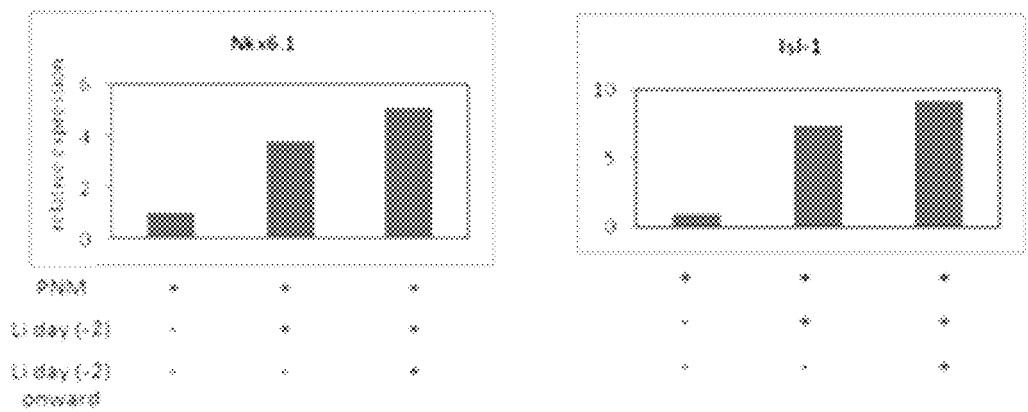
Figure 48C:
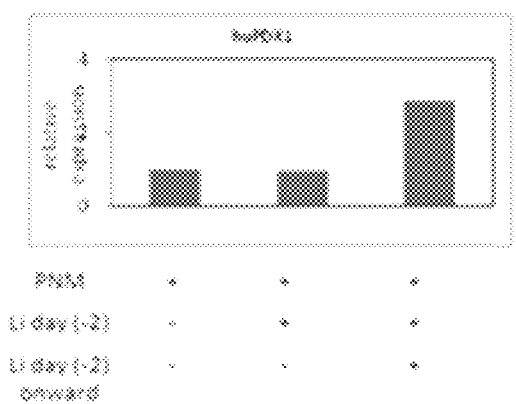

Upon transdifferentiation, cells that were pre-treated with Li demonstrated an increase in insulin secretion (FIG. 48A), as well as expression of pancreatic genes (FIG. 48B) indicating that WNT signaling is a "built-in" signal pathway enabling the cells to undergo efficient transdifferentiation. Interestingly, endogenous PDX-1 expression levels were not upregulated with Li pre-treatment (FIG. 48C), suggesting that late WNT signal is necessary for stable pancreatic repertoire.

While certain features disclosed here have been illustrated and described herein, many modifications, substitutions, changes, and equivalents will now occur to those of ordinary skill in the art. It is, therefore, to be understood that the appended claims are intended to cover all such modifications and changes as fall within the true spirit disclosed here.

---

What is claimed is:

1. A method of manufacturing a population of human insulin producing cells, the method comprising the steps of:
   (a) obtaining adult human liver tissue;
   (b) processing said liver tissue to recover primary adult human liver cells;
   (c) propagating and expanding said primary adult human liver cells to a predetermined number of cells;
   (d) transdifferentiating said expanded cells, wherein said transdifferentiating comprises:
      (1) infecting said expanded cells with at least one expression vector, said infecting occurring at a first time period,
         (i) wherein said at least one expression vector comprises an adenoviral vector comprising a nucleic acid encoding a PDX-1 polypeptide and an expression vector comprising an adenoviral vector comprising a nucleic acid encoding a second pancreatic transcription factor polypeptide selected from NeuroD1 and Pax4, wherein said infecting with said adenoviral vectors occurs at the same time,
         or
         (ii) wherein said at least one expression vector comprises an adenoviral vector comprising a nucleic acid encoding a PDX-1 polypeptide and a second pancreatic transcription factor polypeptide selected from NeuroD1 and Pax4;
         and
      (2) infecting said expanded infected cells of (1) with an adenoviral vector comprising a nucleic acid encoding a MafA polypeptide, said infecting occurring at a second time period, wherein said second time period is after said first time period;
   and
   (e) harvesting said transdifferentiated expanded cells;
   thereby manufacturing said population of human insulin producing cells having an increased insulin content, or increased glucose regulated insulin secretion, or increased glucose regulated C-peptide secretion, or any combination thereof, compared with control non-transdifferentiated liver cells.

2. The method of claim 1, wherein said population of human insulin producing cells expresses increased endogenous Nkx6.1 compared with control non-transdifferentiated liver cells.

3. The method of claim 1, wherein said adult human liver cells express cell surface markers comprising CD73, CD90, CD105, or CD44 or any combination thereof.

4. The method of claim 1, wherein at step (a) said liver tissue is obtained from a subject suffering from pancreatitis or from insulin dependent diabetes.

5. The method of claim 1, wherein at step (c) said propagating and expanding said liver cells comprises expansion through a series of sub-cultivation steps up to a production bioreactor system, or at step (d) said transdifferentiating of said expanded cells comprises transdifferentiation ocurring in a series of bioreactor systems, or a combination thereof.

6. The method of claim 5, wherein said bioreactor system comprises a single bioreactor or multiple bioreactors.

7. The method of claim 5, wherein said bioreactor comprises a single use bioreactor, a multiple use bioreactor, a closed system bioreactor, or an open system bioreactor, or any combination thereof.

8. The method of claim 1, further comprising a step of enriching said primary adult human liver cells for cells predisposed to transdifferentiation, wherein said enriching step is prior to said transdifferentiating step (d).

9. The method of claim 8, wherein said predisposed cells comprise pericentral liver cells.

10. The method of claim 8, said method further comprising incubating said primary adult human liver cells with lithium.

11. The method of claim 10, wherein said incubating is prior to transdifferentiation or at the same time as transdifferentiation.

12. The method of claim 8, wherein said predisposed cells comprise cells comprising:
   (a) an active Wnt-signaling pathway;
   (b) a capability of activating the glutamine synthetase response element (GSRE);
   (c) increased expression of HOMER1, LAMP3, BMPR2, ITGA6, DCBLD2, THBS1, or VAMP4, or any combination thereof;
   (d) decreased expression of ABCB1, ITGA4, ABCB4, or PRNP, or any combination thereof; or
   any combination thereof.

13. The method of claim 1, wherein said pre-determined number of cells comprises at least 1 billion cells.

14. A population of human insulin producing cells manufactured by a method comprising the steps of:
(a) obtaining adult human liver tissue;
(b) processing said liver tissue to recover primary adult human liver cells;
(c) propagating and expanding said primary adult human liver cells to a predetermined number of cells;
(d) transdifferentiating said expanded cells, wherein said transdifferentiating comprises:
  (1) infecting said expanded cells with at least one expression vector, said infecting occurring at a first time period,
    (i) wherein said at least one expression vector comprises an adenoviral vector comprising a nucleic acid encoding a PDX-1 polypeptide and an expression vector comprising an adenoviral vector comprising a nucleic acid encoding a second pancreatic transcription factor polypeptide selected from NeuroD1 and Pax4, wherein said infecting with said adenoviral vectors occurs at the same time,
    or
    (ii) wherein said at least one expression vector comprises an adenoviral vector comprising a nucleic acid encoding a PDX-1 polypeptide and a second pancreatic transcription factor polypeptide selected from NeuroD1 and Pax4;
  and
  (2) infecting said expanded infected cells of (1) with an adenoviral vector comprising a nucleic acid encoding a MafA polypeptide, said infecting occurring at a second time period, wherein said second time period is after said first time period; and
(e) harvesting said transdifferentiated expanded culture;
wherein said population of human insulin producing cells have an increased insulin content or increased glucose stimulated insulin secretion, or increased glucose regulated C-peptide secretion, or any combination thereof, compared with control non-transdifferentiated liver cells.

15. The population of human insulin producing cells of claim 14, wherein said population of human insulin producing cells expresses increased Nkx6.1 compared with control non-transdifferentiated liver cells.

16. The population of human insulin producing cells of claim 14, wherein said adult human primary liver cells express cell surface markers comprising CD73, CD90, CD105, or CD44, or any combination thereof.

17. The population of human insulin producing cells of claim 14, for use in a cell-based therapy for a patient suffering from pancreatitis or from insulin dependent diabetes.

18. The population of human insulin producing cells of claim 17, wherein said cells are autologous or allogeneic with said patient.

19. A composition comprising the population of human insulin producing cells of claim 14, and a pharmaceutically acceptable carrier.

20. The population of human insulin producing cells of claim 14, further comprising a step enriching said primary adult human liver cells for cells predisposed to transdifferentiation, wherein said enriching step is prior to said transdifferentiating step (d).

21. The population of human insulin producing cells of claim 20, wherein said predisposed cells comprise pericentral liver cells.

22. The population of human insulin producing cells of claim 20, said method further comprising incubating said primary adult human liver cells with lithium.

23. The population of human insulin producing cells of claim 20, wherein said predisposed cells comprise cells comprising:
(a) an active Wnt-signaling pathway;
(b) a capability of activating the glutamine synthetase response element (GSRE);
(c) increased expression of HOMER1, LAMP3, BMPR2, ITGA6, DCBLD2, THBS1, or VAMP4, or any combination thereof;
(d) decreased expression of ABCB1, ITGA4, ABCB4, or PRNP, or any combination thereof; or
any combination thereof.

24. The population of human insulin producing cells of claim 20, wherein at step (c) said propagating and expanding said liver cells comprises expansion through a series of sub-cultivation steps up to a production bioreactor system, or at step (d) said transdifferentiating of said expanded cells comprises transdifferentiation occuring in a series of bioreactor systems, or a combination thereof.

25. The population of human insulin producing cells of claim 24, wherein said bioreactor system comprises a single bioreactor or multiple bioreactors.

26. The population of human insulin producing cells of claim 24, wherein said bioreactor comprises a single use bioreactor, a multiple use bioreactor, a closed system bioreactor, or an open system bioreactor, or any combination thereof.

* * * * *